(12) United States Patent
Degnan et al.

(10) Patent No.: US 9,688,669 B2
(45) Date of Patent: Jun. 27, 2017

(54) OXAZOLIDINONES AS MODULATORS OF MGLUR5

(71) Applicant: BRISTOL-MYERS SQUIBB COMPANY, Princeton, NJ (US)

(72) Inventors: Andrew P. Degnan, Rocky Hill, CT (US); Darrell Maxwell, Washington, DC (US); Matthew D. Hill, Wallingford, CT (US); Haiquan Fang, Madison, CT (US); Michael F. Parker, Higganum, CT (US); Fukang Yang, Madison, CT (US); Joanne J. Bronson, Durham, CT (US); John E. Macor, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/026,759

(22) PCT Filed: Oct. 6, 2014

(86) PCT No.: PCT/US2014/059248
§ 371 (c)(1),
(2) Date: Apr. 1, 2016

(87) PCT Pub. No.: WO2015/054103
PCT Pub. Date: Apr. 16, 2015

(65) Prior Publication Data
US 2016/0237072 A1    Aug. 18, 2016

Related U.S. Application Data

(60) Provisional application No. 61/887,580, filed on Oct. 7, 2013.

(51) Int. Cl.
| C07D 413/14 | (2006.01) |
| C07D 413/04 | (2006.01) |
| C07D 263/24 | (2006.01) |

(52) U.S. Cl.
CPC ......... *C07D 413/04* (2013.01); *C07D 263/24* (2013.01); *C07D 413/14* (2013.01); *C07B 2200/07* (2013.01)

(58) Field of Classification Search
USPC .............................. 514/249, 252.05, 255.05
See application file for complete search history.

(56) References Cited

U.S. PATENT DOCUMENTS

| 8,691,821 B2 * | 4/2014 | Degnan ................ C07D 263/18 514/249 |
| 2012/0283264 A1 * | 11/2012 | Degnan ................ C07D 263/18 514/249 |

* cited by examiner

*Primary Examiner* — Pancham Bakshi
(74) *Attorney, Agent, or Firm* — James Epperson

(57) ABSTRACT

The disclosure generally relates to compounds of formula I, including their salts, as well as compositions and methods of using the compounds. The compounds are ligands, agonists and partial agonists for the mGluR5 receptor and may be useful for the treatment of various disorders of the central nervous system.

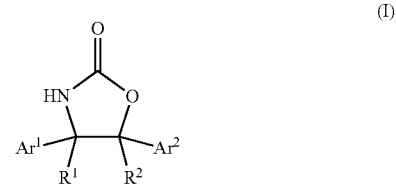

(I)

12 Claims, No Drawings

OXAZOLIDINONES AS MODULATORS OF MGLUR5

CROSS-REFERENCE TO RELATED APPLICATIONS

This application claims priority to Provisional Patent Application U.S. Ser. No. 61/887,580 filed Oct. 7, 2013, hereby incorporated by reference in its entirety.

BACKGROUND OF THE INVENTION

The disclosure generally relates to compounds of formula I, including their salts, as well as compositions and methods of using the compounds. The compounds are ligands, agonists and partial agonists for the mGluR5 receptor and may be useful for the treatment of various disorders of the central nervous system.

Glutamate is the major excitatory neurotransmitter in the mammalian brain, playing an important physiological role in a wide variety of processes. Glutamatergic neurotransmission is predominantly mediated through activation of cell surface receptors including ligand-gated ion channels (ionotropic receptors) and metabotropic glutamate G protein coupled receptors (mGluRs). The metabotropic glutamate receptor family is comprised of 8 family members that are part of the family 3 GPCR superfamily. These receptors are further subdivided into Group I (mGluR 1, 5), Group II (mGluR 2, 3) and Group III (mGluR 4, 6, 7, 8) based upon sequence homology, receptor signaling, and pharmacology.

The Group I receptor mGluR5 has emerged as a target of potential therapeutic utility in a number of disease states (see: Rodriguez, A. L., et al. Current Opinion in Drug Discovery & Development (2007), 10(6), 715-722. and Chen, Y., et al. Drugs of the Future (2008), 33(4), 355-360. and Lindsley, C. W., et al. Current Opinion in Drug Discovery & Development (2009), 12(4), 446-457). The receptor is expressed broadly throughout the CNS with predominant post-synaptic localization, although pre-synaptic expression is also present. mGluR5 is a Gαq-coupled receptor activating phospholipase C and elevating intracellular calcium levels, leading to activation of downstream signaling molecules. Many studies have demonstrated a role for the receptor in regulating NMDA receptor activity as well as synaptic plasticity, suggesting this receptor plays a key role in glutamatergic signal transduction.

Based on the expression pattern and functional role of mGluR5, this receptor has emerged as an important target for drug discovery in a number of therapeutic indications. Evaluation of genetically modified mice lacking mGluR5 as well as compounds that modulate receptor function suggest ligands that modulate mGluR5 receptor function have therapeutic utility in CNS and peripheral disease states including, but not limited to, schizophrenia (see: Conn, P. J., et al. Trends in Pharmacological Sciences (2009), 30(1), 25-31; and Kanuma, K., et al. Recent Patents on CNS Drug Discovery (2010), 5(1), 23-34), cognitive impairment (see: Simonyi, A., et al. European Journal of Pharmacology (2010), 639(1-3), 17-25), Alzheimer's disease, Parkinson's disease (see: Johnson, K. A., et al. CNS & Neurological Disorders: Drug Targets (2009), 8(6), 475-491), Parkinson's disease levodopa-induced dyskinesia (see: Rylander, D., et al. Neurobiology of Disease (2010), 39(3), 352-361), addiction (see: Olive, M. F. Current Drug Abuse Reviews (2009), 2(1), 83-98), anxiety (see: Jacob, W., et al. Neuropharmacology (2009), 57(2), 97-108), depression (see: Witkin, J. M., et al. CNS & Neurological Disorders: Drug Targets (2007), 6(2), 87-100), psychosis, epilepsy, Fragile X (see: Dolen, G., et al. Journal of Physiology (Oxford, United Kingdom) (2008), 586(6), 1503-1508), gastroesophageal reflux disease (see: Boeckxstaens, G. E. Expert Opinion on Emerging Drugs (2009), 14(3), 481-491), migraine (see: Marin, J., et al. Expert Opinion on Investigational Drugs (2010), 19(4), 555-561), pain, and others.

The invention provides technical advantages, for example, the compounds are novel and are ligands for the mGluR5 receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders related to glutamatergic dysfunction.

One aspect of the invention is a compound of formula I

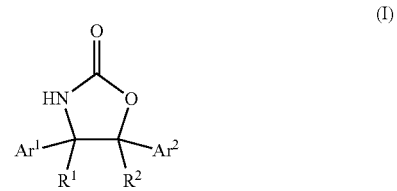

where:
$R^1$ is hydrogen or alkyl;
$R^2$ is hydrogen or alkyl;
$R^3$ is

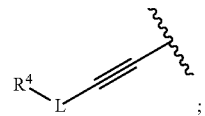

$R^4$ is cyano, alkyl, haloalkyl, cycloalkyl, hydroxy, alkoxy, haloalkoxy, or thioalkyl, where alkyl, haloalkyl, and cycloalkyl are substituted with 0-3 substituents selected from halo, alkyl, haloalkyl, hydroxy, and alkoxy;
or $R^4$ is a bridged [1-4.1-4.0-3]bicycloalkyl;
or $R^4$ is alkylcarbonylamino, haloalkylcarbonylamino, cycloalkanonyl, valerolactamyl, oxetanyl, tetrahydrofuranyl, tetrahydropyranyl, tetrahydropyranyloxy, phenyl, or phenoxy;
or $R^4$ is amino, alkylamino, dialkylamino, azetidinyl, pyrrolidinyl, piperidinyl, piperazinyl, morpholinyl, homopiperidinyl, homopiperazinyl, or homomorpholinyl;
or $R^4$ is pyrazolyl, isoxazolyl, isothiazolyl, imidazolyl, oxazolyl, thiazolyl, triazolyl, oxadiazolyl, thiadiazolyl, or indazolyl, and is substituted with 0-2 substituents selected from halo and alkyl;
L is a bond, alkylene, or hydroxyalkylene;
$Ar^1$ is phenyl, pyridinyl, pyrazinyl, pyrimidinyl, or pyridazinyl, and is substituted with 1 $R^3$ substituent and with 0-3 substituents selected from cyano, halo, alkyl, haloalkyl, alkoxy, and haloalkoxy; and $Ar^2$ is phenyl, pyridinyl, pyrazinyl, pyrimidinyl, pyridazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, tetrazolyl, or benzimidazolyl, and is substituted with 0-3 substituents selected from cyano, halo, alkyl, haloalkyl, hydroxy, alkoxy, haloalkoxy, and phenyl;

or a pharmaceutically acceptable salt thereof.

Another aspect of the invention is a compound of formula I where $R^1$ is hydrogen;
$R^2$ is hydrogen;
$R^3$ is

$R^4$ is cyano, alkyl, haloalkyl, cycloalkyl, hydroxy, alkoxy, haloalkoxy, or thioalkyl, where alkyl, haloalkyl, and cycloalkyl are substituted with 0-3 substituents selected from halo, alkyl, haloalkyl, hydroxy, and alkoxy;

or $R^4$ is a bridged [1-4.1-4.0-3]bicycloalkyl;

or $R^4$ is alkylcarbonylamino, haloalkylcarbonylamino, cycloalkanonyl, valerolactamyl, oxetanyl, tetrahydropyranyl, tetrahydropyranyl, tetrahydropyranyloxy, phenyl, or phenoxy;

or $R^4$ is amino, alkylamino, dialkylamino, azetidinyl, pyrrolidinyl, piperidinyl, piperazinyl, morpholinyl, homopiperidinyl, homopiperazinyl, or homomorpholinyl;

or $R^4$ is pyrazolyl, isoxazolyl, isothiazolyl, imidazolyl, oxazolyl, thiazolyl, triazolyl, oxadiazolyl, thiadiazolyl, or indazolyl, and is substituted with 0-2 substituents selected from halo and alkyl;

L is a bond, alkylene, or hydroxyalkylene;

$A^1$ is phenyl, pyridinyl, pyrazinyl, pyrimidinyl, or pyridazinyl, and is substituted with 1 $R^3$ substituent and with 0-3 substituents selected from cyano, halo, alkyl, haloalkyl, alkoxy, and haloalkoxy; and $Ar^2$ is phenyl, pyridinyl, pyrazinyl, pyrimidinyl, pyridazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, tetrazolyl, or benzimidazolyl, and is substituted with 0-3 substituents selected from cyano, halo, alkyl, haloalkyl, hydroxy, alkoxy, haloalkoxy, and phenyl;

or a pharmaceutically acceptable salt thereof.

Another aspect of the invention is a compound of formula I where $R^1$ is hydrogen; $R^2$ is hydrogen; $R^3$ is

$R^4$ is cyano, alkyl, haloalkyl, cycloalkyl, hydroxy, alkoxy, haloalkoxy, or thioalkyl, where alkyl, haloalkyl, and cycloalkyl are substituted with 0-3 substituents selected from halo, alkyl, haloalkyl, hydroxy, and alkoxy; or $R^4$ is a bridged [1-4.1-4.0-3]bicycloalkyl; or $R^4$ is alkylcarbonylamino, haloalkylcarbonylamino, cycloalkanonyl, valerolactamyl, oxetanyl, tetrahydrofuranyl, tetrahydropyranyl, tetrahydropyranyloxy, phenyl, or phenoxy; or $R^4$ is amino, alkylamino, dialkylamino, azetidinyl, pyrrolidinyl, piperidinyl, piperazinyl, morpholinyl, homopiperidinyl, homopiperazinyl, or homomorpholinyl; or $R^4$ is pyrazolyl, isoxazolyl, isothiazolyl, imidazolyl, oxazolyl, thiazolyl, triazolyl, oxadiazolyl, thiadiazolyl, or indazolyl, and is substituted with 0-2 substituents selected from halo and alkyl; L is a bond, alkylene, or hydroxyalkylene; $Ar^1$ is pyridinyl substituted with 1 $R^3$ substituent and with 0-3 substituents selected from cyano, halo, alkyl, haloalkyl, alkoxy, and haloalkoxy; and $Ar^2$ is phenyl substituted with 0-3 substituents selected from cyano, halo, alkyl, haloalkyl, hydroxy, alkoxy, haloalkoxy, and phenyl; or a pharmaceutically acceptable salt thereof.

Another aspect of the invention is a compound of formula I where $R^1$ and $R^2$ is hydrogen.

Another aspect of the invention is a compound of formula I where $R^4$ is cyano, alkyl, haloalkyl, cycloalkyl, hydroxy, alkoxy, haloalkoxy, or thioalkyl, where alkyl, haloalkyl, and cycloalkyl are substituted with 0-3 substituents selected from halo, alkyl, haloalkyl, hydroxy, and alkoxy.

Another aspect of the invention is a compound of formula I where $R^4$ is amino, alkylamino, dialkylamino, azetidinyl, pyrrolidinyl, piperidinyl, piperazinyl, morpholinyl, homopiperidinyl, homopiperazinyl, or homomorpholinyl.

Another aspect of the invention is a compound of formula I where $R^4$ is pyrazolyl, isoxazolyl, isothiazolyl, imidazolyl, oxazolyl, thiazolyl, triazolyl, oxadiazolyl, thiadiazolyl, or indazolyl, and is substituted with 0-2 substituents selected from halo and alkyl.

Another aspect of the invention is a compound of formula I where L is a bond.

Another aspect of the invention is a compound of formula I where L is alkylene.

Another aspect of the invention is a compound of formula I where L is hydroxyalkylene.

Another aspect of the invention is a compound of formula I where L is a bond, methylene, or hydroxymethylene.

Another aspect of the invention is a compound of formula I where $Ar^1$ is pyridinyl substituted with 1 $R^3$ substituent and with 0-3 substituents selected from cyano, halo, alkyl, haloalkyl, alkoxy, and haloalkoxy.

Another aspect of the invention is a compound of formula I where $Ar^2$ is phenyl substituted with 0-3 substituents selected from cyano, halo, alkyl, haloalkyl, hydroxy, alkoxy, haloalkoxy, and phenyl.

Another aspect of the invention is a compound of formula I with the indicated stereochemistry

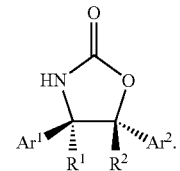

For a compound of formula I, the scope of any instance of a variable substituent, including $R^1$, $R^2$, $R^3$, $R^4$, L, $Ar^1$, and $Ar^2$ can be used independently with the scope of any other instance of a variable substituent. As such, the invention includes combinations of the different aspects.

Unless specified otherwise, these terms have the following meanings "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art. The relative and absolute stereochemistry of formula I compounds depicted in the specific embodiments section (and the intermediates used to prepare them) represent the most likely stereoisomer based on the data collected for each compound.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

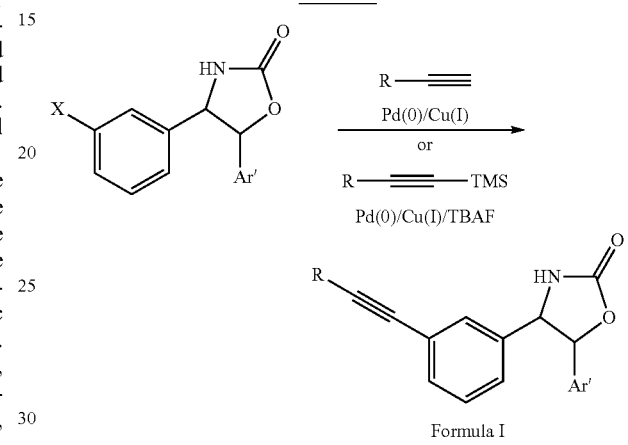

Scheme 1.

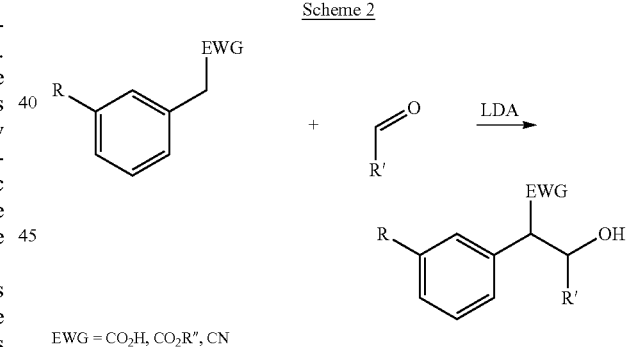

Scheme 2

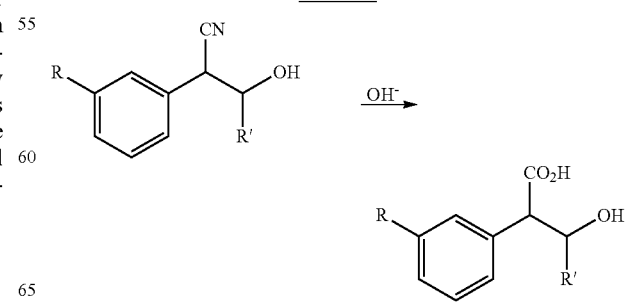

Scheme 3.

Scheme 4.
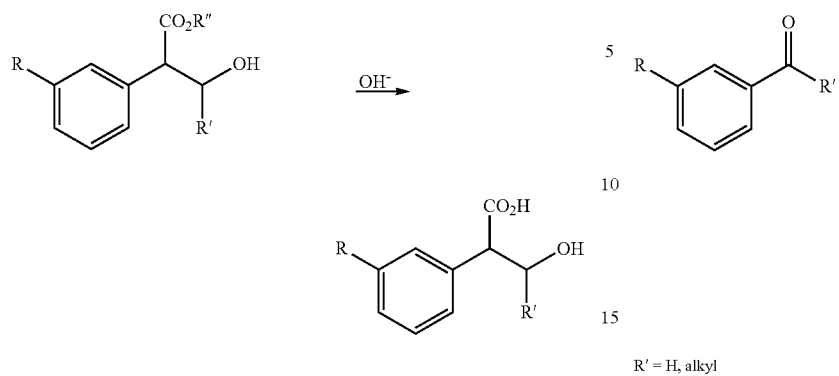
Scheme 6.
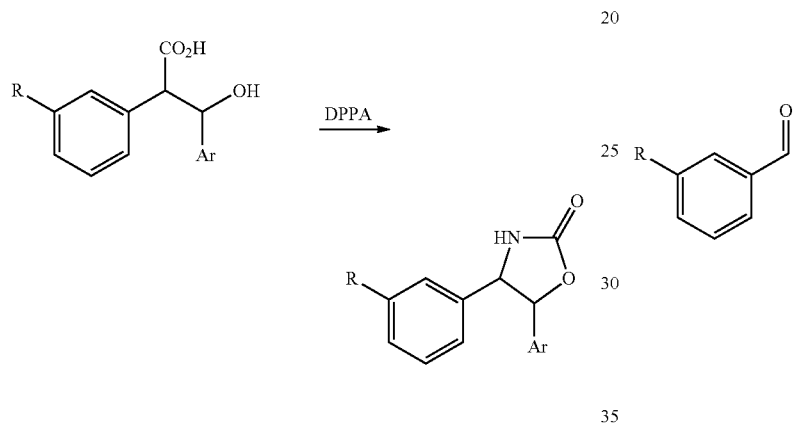
R' = H, alkyl
Scheme 7.
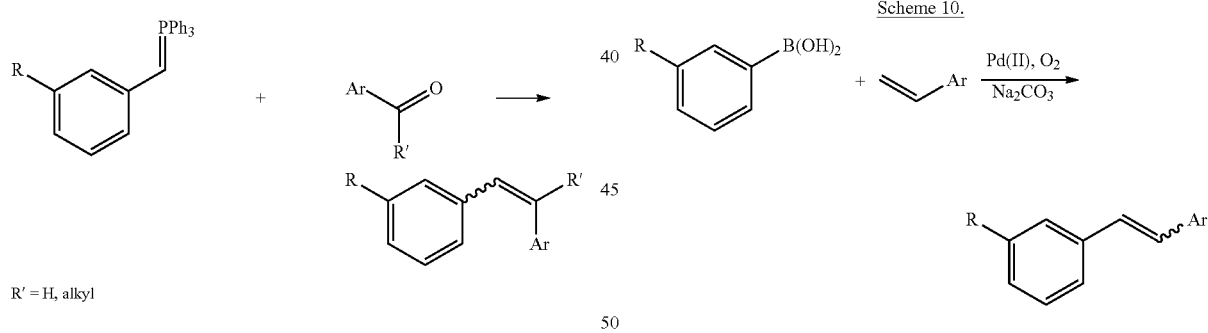
Scheme 8.
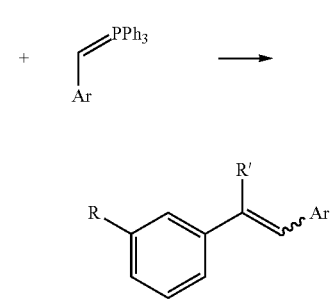
Scheme 9.
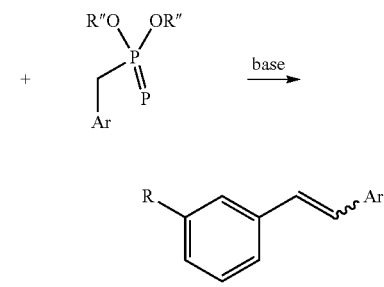
Scheme 10.
Scheme 11.
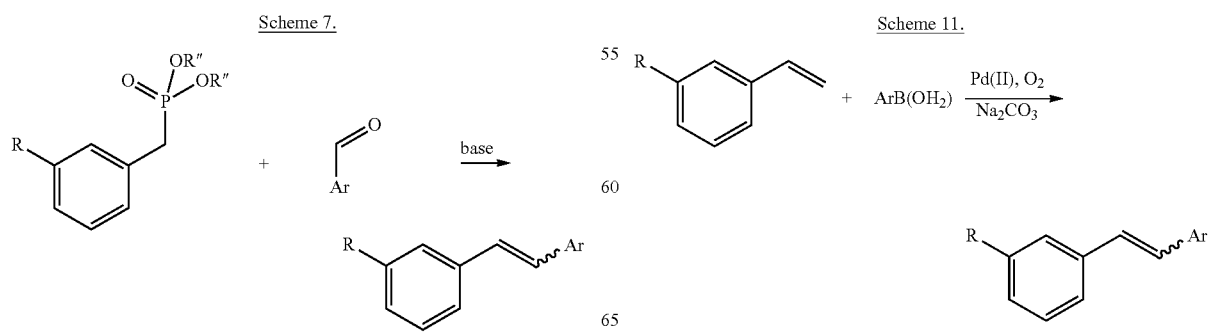

Scheme 12.
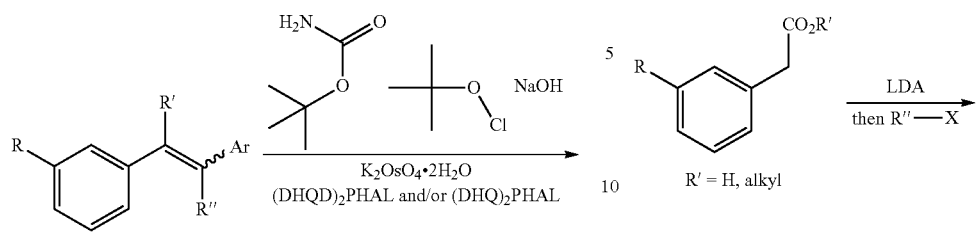
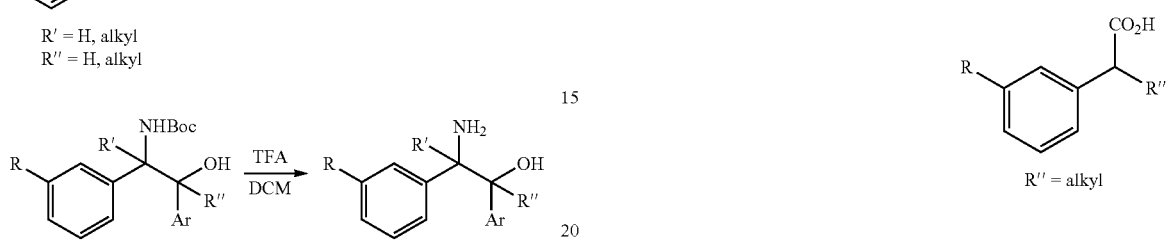
Scheme 13.
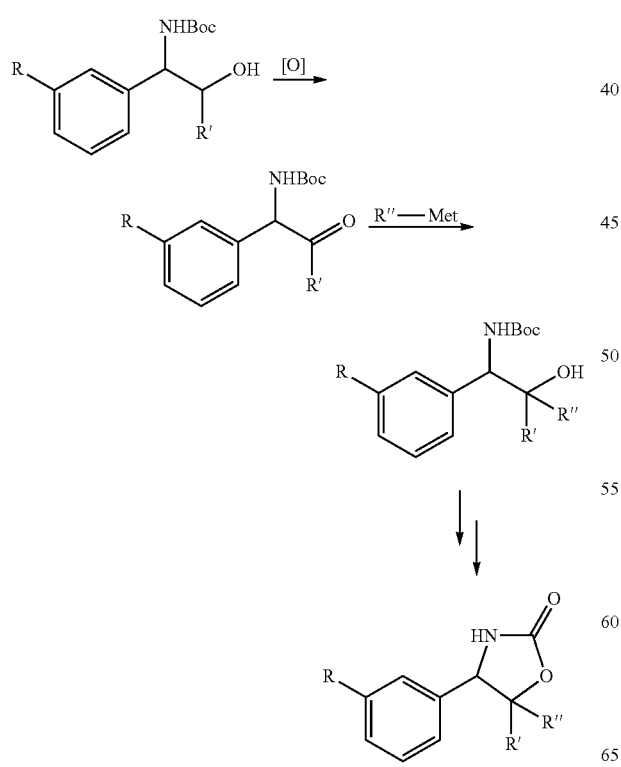
Scheme 14.
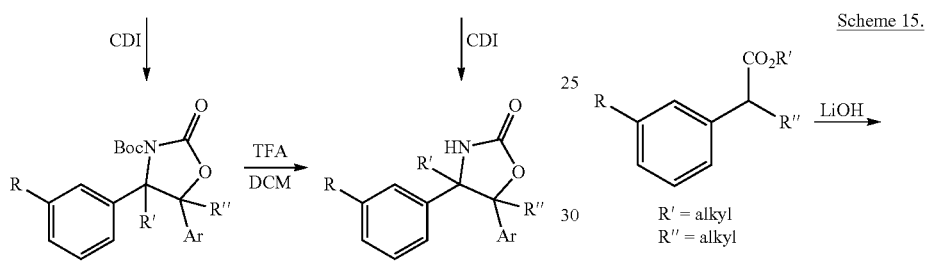
Scheme 15.
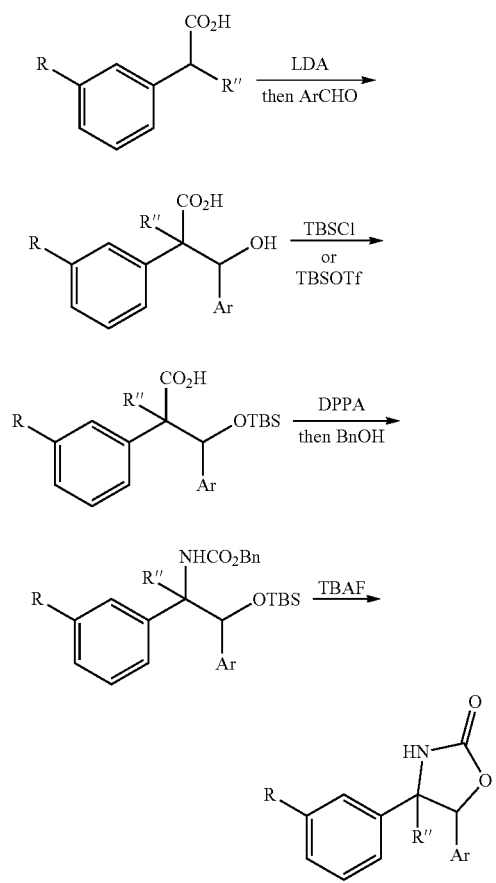

Scheme 16.
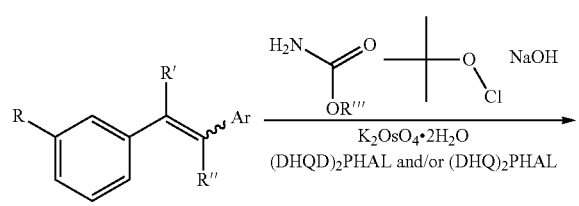
R' = H, alkyl
R'' = H, alkyl
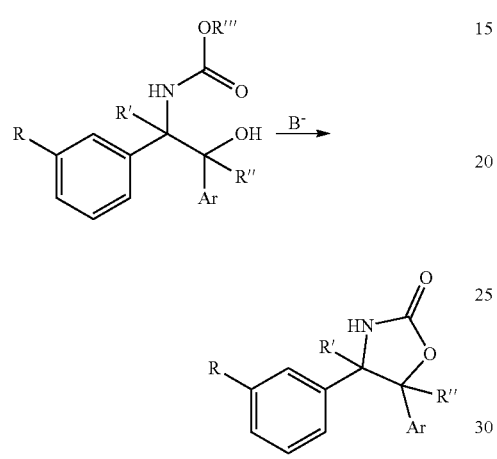
Scheme 17.
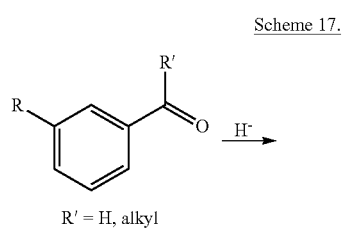
R' = H, alkyl
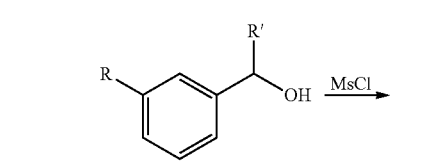
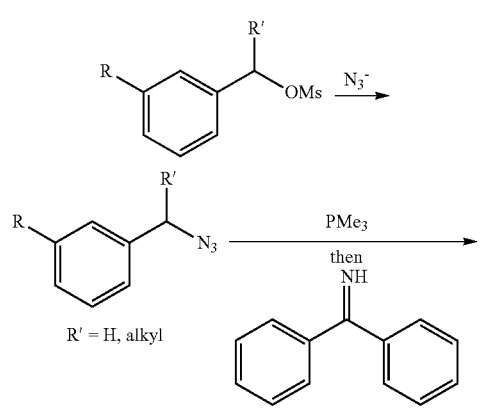
R' = H, alkyl
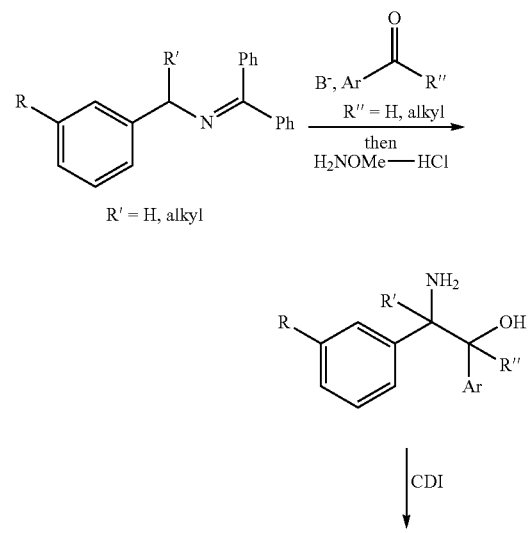
R'' = H, alkyl
Scheme 18.
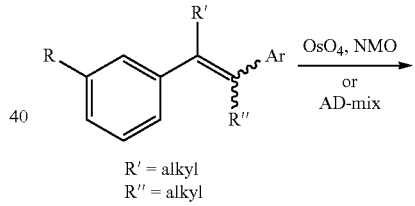
R' = alkyl
R'' = alkyl
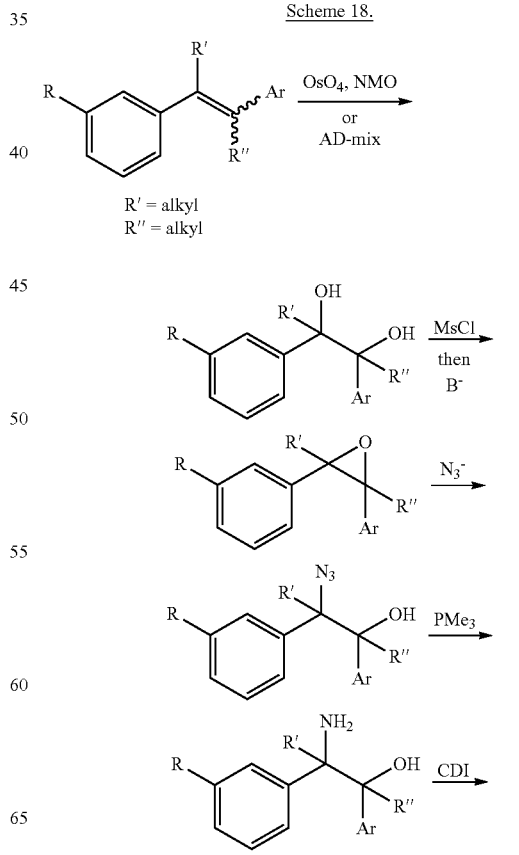

-continued
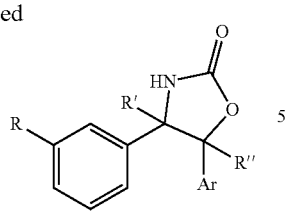
Scheme 19.
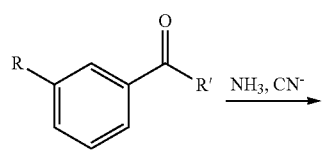
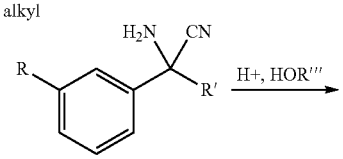
-continued
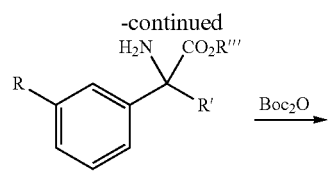
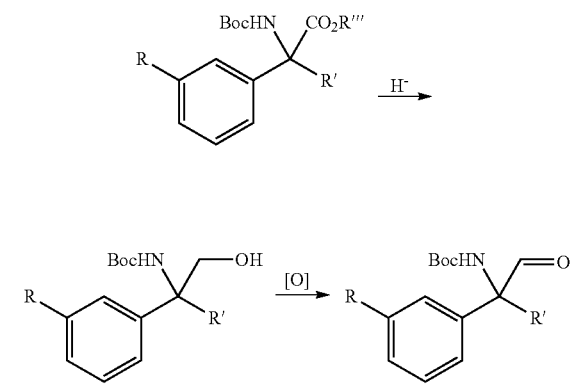
Scheme 20.
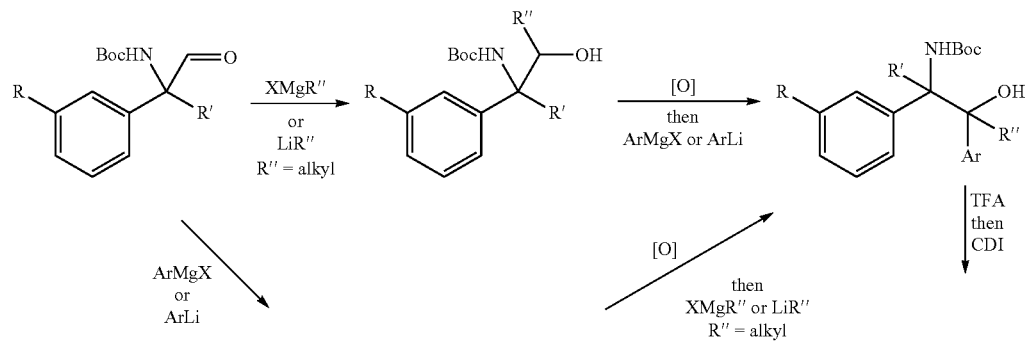
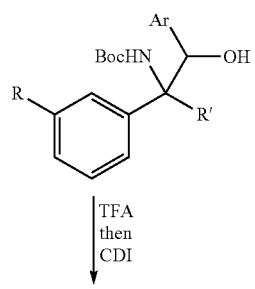
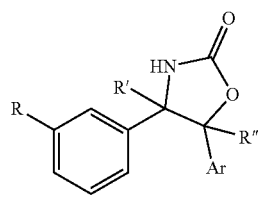
TFA
then
CDI
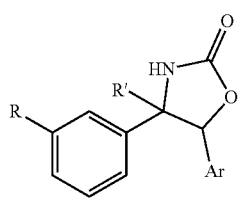

Scheme 21.

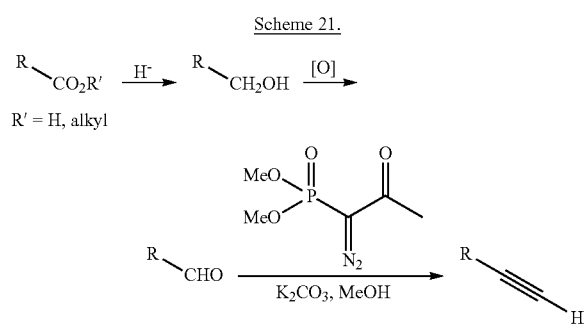

Scheme 22.

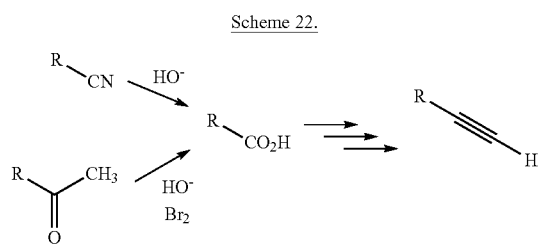

Scheme 23.

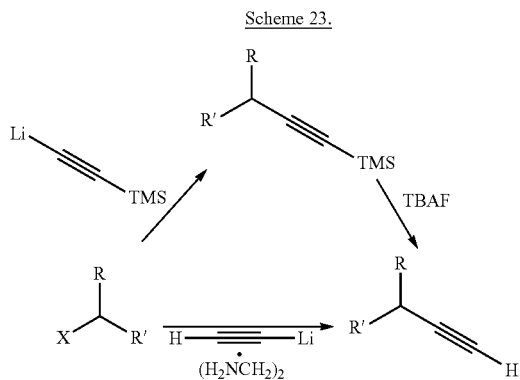

R,R' = H, alkyl, cycloalkyl,
aryl, substited alkyl
X = halogen, leaving group

Scheme 24.

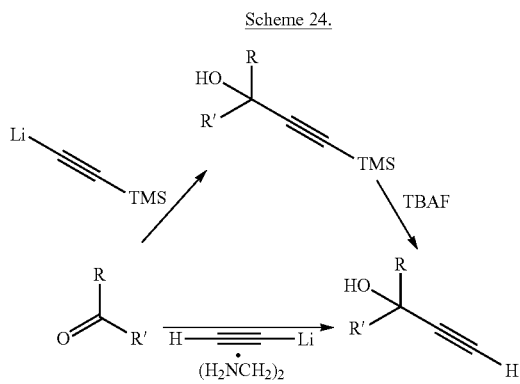

R,R' = H, alkyl, cycloalkyl,
aryl, substituted alkyl

Biological Methods mGluR5 FLIPR Assay.

HEK293 (ZF) cells stably transfected with human mGluR5A (pIRES neo) and the rat glutamate-aspartate transporter (GLAST; pIRES puro) are grown in a monolayer culture at 37° C. in 5% $CO_2$ and fed with Minimum Essential Medium (MEM) supplemented with 10% dialysed fetal bovine serum. 24 hours prior to assay, cells are enzymatically dissociated from the culture flask (Trypsin, 0.25%), spun down (1000 rpm, 3 min), resuspended, and plated on Greiner black clear bottomed PDL-coated 384-well plates at a density of 30 thousand cells/well. On the day of the experiment, media is removed from the cell plates and replaced with Molecular Devices Calcium 4 microfluorometric $Ca^{++}$ sensitive dye in assay buffer (HBSS; Gibco #14025+20 mM HEPES and 250 uM probenacid). Plates are incubated in dye at 37° C. in 5% $CO_2$ for 60 minutes prior to delivery of test compounds in assay buffer. Test compounds are incubated with cells in the presence of dye for 10 minutes prior to being read on the FLIPR platform (Molecular Devices). A $Ca^{++}$ signal is induced in the assay plates via the delivery of an ~$EC_{10}$ concentration of the endogenous agonist 1-glutamate; images are acquired at 1 Hz for 100 seconds post-delivery of agonist stimulus. Positive modulator activity (i.e. the ability of test compounds to increase the $Ca^{++}$ response to a sub-maximal concentration of agonist) is normalized to a saturating concentration of a known mGluR5 PAM run in each assay plate. An $EC_{50}$ concentration of test compounds is derived from 4-parameter logistic curve fits of transformed fluoresence data via proprietary software suite.

| Example | mGluR5 $EC_{50}$ (nM) |
|---|---|
| 1 | 1.7 |
| 2 | 2.0 |
| 3 | 2.2 |
| 4 | 3.6 |
| 5 | 4.7 |
| 6 | 5.2 |
| 7 | 5.9 |
| 8 | 12.3 |
| 9 | 11.4 |
| 10 | 12.6 |
| 11 | 13.6 |
| 12 | 15.4 |
| 13 | 16.4 |
| 14 | 16.6 |
| 15 | 20.4 |
| 16 | >3226 |
| 17 | 23.2 |
| 18 | 26.0 |
| 19 | 27.6 |
| 20 | 60.8 |
| 21 | 29.5 |
| 22 | 32.3 |
| 23 | 43.6 |
| 24 | 43.9 |
| 25 | 45.2 |
| 26 | 46.2 |
| 27 | 48.2 |
| 28 | 76.9 |
| 29 | 77.5 |
| 30 | 85.1 |
| 31 | 108 |
| 32 | 116 |
| 33 | 134 |
| 34 | 244 |
| 35 | 255 |
| 36 | 291 |
| 37 | 383 |
| 38 | 498 |

| Example | mGluR5 EC$_{50}$ (nM) |
|---|---|
| 39 | 510 |
| 40 | 513 |
| 41 | 730 |
| 42 | >1613 |
| 43 | >1613 |
| 44 | >1613 |
| 45 | >1613 |
| 46 | >1613 |
| 47 | >1613 |
| 48 | >1613 |
| 49 | >1613 |
| 50 | >3226 |
| 51 | 8.1 |
| 52 | 9.3 |
| 53 | 16.2 |
| 54 | 107 |
| 55 | 27.8 |
| 56 | 67.0 |
| 57 | 77.3 |
| 58 | 204 |
| 59 | 226 |
| 60 | 458 |
| 61 | >3226 |
| 62 | 10.9 |
| 63 | 12.4 |
| 64 | 20.0 |
| 65 | 14.7 |
| 66 | 15.2 |
| 67 | 88.6 |
| 68 | 932 |
| 69 | >1613 |
| 70 | 29.6 |
| 71 | >3226 |
| 72 | 16.6 |
| 73 | 27.9 |
| 74 | 27.4 |
| 75 | 129 |
| 76 | 334 |
| 77 | >1613 |
| 78 | >1613 |
| 79 | 463 |
| 80 | >3000 |
| 81 | 351 |
| 82 | 1308 |
| 83 | 48.7 |
| 84 | 3667 |
| 85 | 1055 |
| 86 | 25.3 |
| 87 | >10750 |
| 88 | 90.2 |
| 89 | 8.3 |
| 90 | 377 |
| 91 | 96.2 |
| 92 | 50.9 |
| 93 | 77.0 |
| 94 | >3226 |
| 95 | 237 |
| 96 | >3226 |
| 97 | 30.5 |
| 98 | >3226 |
| 99 | 13.2 |
| 100 | 282 |
| 101 | >1613 |
| 102 | >3226 |
| 103 | 251 |
| 104 | >1613 |
| 105 | 326 |
| 106 | 295 |
| 107 | 280 |
| 108 | 65.9 |
| 109 | >3226 |
| 110 | >3226 |
| 111 | 104 |
| 112 | >3226 |
| 113 | >3226 |
| 114 | >3226 |
| 115 | 35.1 |
| 116 | >1613 |
| 117 | >3226 |
| 118 | 80.5 |
| 119 | 21.6 |
| 120 | 69.2 |
| 121 | 18.4 |
| 122 | 58.6 |
| 123 | 60.4 |
| 124 | 130.4 |
| 125 | 179.2 |

Pharmaceutical Compositions and Methods of Treatment

Compounds of formula I bind to mGluR5 and can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment of schizophrenia, cognitive impairment, Alzheimer's disease, Parkinson's disease, Parkinson's disease levodopa-induced dyskinesia, addiction, anxiety, depression, psychosis, epilepsy, Fragile X, gastroesophageal reflux disease, migraine, pain, borderline personality disorder, bipolar disorder, or other neurological and/or psychiatric disorder associated with glutamate dysfunction, which comprises administering to a patient a therapeutically affective amount of a compound of formula I.

Another aspect of the invention is a method for the treatment of schizophrenia which comprises administering to a patient a therapeutically affective amount of a compound of formula I.

Another aspect of the invention is a method for the treatment of Alzheimer's disease which comprises administering to a patient a therapeutically affective amount of a compound of formula I.

Another aspect of the invention is the use of a compound of formula I in the manufacture of a medicament for the treatment of neurological or psychiatric disorders.

Another aspect of the invention is the use of a compound of formula I in the manufacture of a medicament for the treatment of schizophrenia, cognitive impairment, Alzheimer's disease, Parkinson's disease, Parkinson's disease levodopa-induced dyskinesia, addiction, anxiety, depression, psychosis, epilepsy, Fragile X, gastroesophageal reflux disease, migraine, pain, borderline personality disorder, bipolar disorder, or other neurological and/or psychiatric disorder associated with glutamate dysfunction.

Another aspect of the invention is the use of a compound of formula I in the manufacture of a medicament for the treatment of Alzheimer's disease.

Another aspect of the invention is the use of a compound of formula I in the manufacture of a medicament for the treatment of schizophrenia.

"Patient" means a person suitable for therapy as understood by practitioners in the field of affective disorders and neurodegenerative disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS

The following experimental procedures describe the synthesis of some Formula I compounds. Standard chemistry conventions are used in the text unless otherwise noted. The experimental encompass reasonable variations known in the art. The following HPLC conditions may be used where indicated.

Analytical HPLC Method 1: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 min, then a 0.5 min hold at 100% B; Flow: 1 mL/min.

Analytical HPLC Method 2: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 min, then a 05 min hold at 100% B; Flow: 0.5 mL/min.

Preparative HPLC Method 1: Column: Waters XBridge C18, 19×200 mm, 5-μm particles; Guard Column: Waters XBridge C18, 19×10 mm, 5-μm particles; Mobile Phase A: water; Mobile Phase B: methanol; Buffer: 20-mM ammonium acetate; Gradient: 20-95% B over 19.5 min, then a 14.0 min hold at 95% B; Flow: 20 mL/min.

Preparative HPLC Method 2: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-100% B over 18 min, then a 4 min hold at 100% B; Flow: 20 mL/min.

Preparative HPLC Method 3: Column: Waters XBridge C18, 19×200 mm, 5-μm particles; Guard Column: Waters XBridge C18, 19×10 mm, 5-m particles; Mobile Phase A: water with 20-mM ammonium acetate; Mobile Phase B: 95:5 methanol:water with 20-mM ammonium acetate; Gradient: 40-80% B over 40 min, then a 5 min hold at 100% B; Flow: 20 mL/min.

Preparative HPLC Method 4: Column: Sunfire C18, 19×100 mm, 5-μm particles; Mobile Phase A: 90:10 water:methanol+0.1% TFA; Mobile Phase B: 90:10 methanol:water+0.1% TFA; Gradient: 20-60% B over 15 min, then a 10 min hold at 60% B; Flow: 30 mL/min.

Preparative HPLC Method 5: Column: Sunfire C18, 19×100 mm, 5-μm particles; Mobile Phase A: 90:10 water:methanol+0.1% TFA; Mobile Phase B: 90:10 methanol:water+0.1% TFA; Gradient: 15-100% B over 15 min, then a 5 min hold at 100% B; Flow: 30 mL/min.

Preparative HPLC Method 6: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-100% B over 20 min, then a 5 min hold at 100% B; Flow: 20 mL/min.

Preparative HPLC Method 7: Column: Sunfire C18, 19×100 mm, 5-μm particles; Mobile Phase A: 90:10 water:methanol+0.1% TFA; Mobile Phase B: 90:10 methanol:water+0.1% TFA; Gradient: 20-100% B over 15 min, then a 10 min hold at 100% B; Flow: 30 mL/min.

Preparative HPLC Method 8: Column: Sunfire C18, 19×100 mm, 5-μm particles; Mobile Phase A: 90:10 water:methanol+0.1% TFA; Mobile Phase B: 90:10 methanol:water+0.1% TFA; Gradient: 0-100% B over 15 min, then a 3 min hold at 100% B; Flow: 30 mL/min.

Preparative HPLC Method 9: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 20-100% B over 20 min, then a 5 min hold at 100% B; Flow: 20 mL/min.

Abbreviations used in the schemes generally follow conventions used in the art. Chemical abbreviations used in the specification and examples are defined as follows: "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "ACN" for acetonitrile; "DIEA" for diisopropylethylamine; "(DHQD)$_2$PHAL" for hydroquinidine 1,4-phthalazinediyldiether.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Intermediate 1

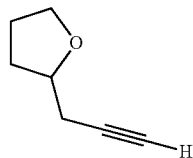

(±)-2-(Prop-2-yn-1-yl)tetrahydrofuran (±)-2-(Bromomethyl)tetrahydrofuran (138 μL, 1.21 mmol) was added drop wise to a stirred suspension of lithium acetylide ethylenediamine complex (149 mg, 1.45 mmol) in dimethylsulfoxide (1.2 mL) at ambient temperature. The reaction was stirred for 2 h, quenched with saturated ammonium chloride (5 mL), and diluted with diethyl ether (15 mL). The layers were separated, and the organic layer washed with water (10 mL). The layers were separated, and the organic layer dried over sodium sulfate. The solids were removed by filtration. The volatiles were distilled to provide a solution of the title compound in diethyl ether which was used without additional purification.

Intermediate 2

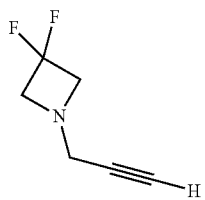

3,3-Difluoro-1-(prop-2-yn-1-yl)azetidine

Potassium carbonate (133 mg, 0.961 mmol) and propargyl bromide (71.4 μL, 0.641 mmol) were added to a stirred solution of 3,3-difluoroazetidine hydrochloride (83.0 mg, 0.641 mmol) in methanol (854 μL) at ambient temperature under nitrogen. The reaction was stirred for 16 h and diluted with water (10 mL) and pentane (20 mL). The layers were separated, and the organic layer dried over sodium sulfate. The solids were removed by filtration and the volatiles carefully removed at 0° C. to afford the title compound which was used without additional purification.

Intermediate 3

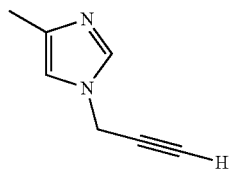

4-Methyl-1-(prop-2-yn-1-yl)-1H-imidazole

Sodium hydride (43.8 mg, 1.10 mmol) was added to a stirred solution of 4-methyl-1H-imidazole (75.0 mg, 0.913 mmol) in dimethylformamide (913 μL) at ambient temperature under nitrogen. After 5 min, propargyl bromide (153 μL, 1.37 mmol) was added, and the reaction stirred for 3 h. The solids were removed using a syringe filter. The filtrate was diluted with water (5 mL) and ethyl acetate (5 mL). The layers were separated, and the aqueous layer was extracted with a second portion of ethyl acetate (5 mL). The combined organic layers were washed with brine (5 mL), the layers were separated, and the organics dried over sodium sulfate. The solids were removed by filtration. The volatiles were carefully removed under reduced pressure to afford the title compound which was used without additional purification.

Intermediate 4

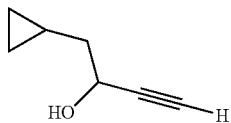

(±)-1-Cyclopropylbut-3-yn-2-ol

To a colorless solution of ethynyltriisopropylsilane (7.92 mL, 35.6 mmol) in anhydrous tetrahydrofuran (50 mL) was drop wise added n-BuLi (14.3 mL, 35.8 mmol) at −78° C. under nitrogen over 5 min. The resulting colorless mixture was stirred for 30 min, followed by addition of crude 2-cyclopropylacetaldehyde (1.68 g, 20.0 mmol) in tetrahydrofuran (3 mL) over 2 min at −78° C. The resulting tan mixture was stirred for 2 h at −78° C., and the reaction quenched with saturated ammonium chloride (10 mL) and partitioned between water (20 mL) and diethyl ether (50 mL). After separation, the organic phase was washed with brine (20 mL) and dried over magnesium sulfate. The solids were removed by filtration, and the volatiles concentrated under reduced pressure to afford crude 1-cyclopropyl-4-(triisopropylsilyl)but-3-yn-2-ol. The crude material was subsequently deprotected by adding tetrabutylammonium fluoride (1 M in THF, 36.0 mL, 36.0 mmol) over 5 min at 0° C. The reaction mixture was stirred at that temperature for 1 h. The reaction mixture was then removed from the ice-water bath and was allowed to warm to ambient temperature over 2 h. The reaction mixture was partitioned between saturated ammonium chloride (10 mL) and diethyl ether (10 mL). The layers were separated, and the organics washed with brine (10 mL), dried over magnesium sulfate, and the volatiles carefully removed under reduced pressure to afford the title compound which was used without additional purification.

Intermediate 5

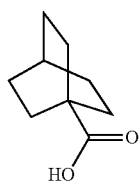 [SMILES: O=C(O)C12CCC(CC1)CC2]

Bicyclo[2.2.2]octane-1-carboxylic acid

A flask was charged with 4-(methoxycarbonyl)bicyclo [2.2.2]octane-1-carboxylic acid (1 g, 4.71 mmol), 2,2'-disulfanediylbis(pyridine 1-oxide) (1.427 g, 5.65 mmol), and dichloromethane (50 mL). The flask was masked with foil to reduce ambient light. The resulting suspension was cooled to 0° C. and treated with tributylphosphine (1.453 mL, 5.89 mmol) drop wise. The ice bath was removed and stirring continued for 2 h. The reaction was cooled to 0° C. and treated with 2-methylpropane-2-thiol (4.7 mL, 41.7 mmol). The reaction was irradiated with a 300 W Tungsten lamp for 1.25 h. The reaction was quenched by addition of a suspension of 10 g calcium hypochlorite in water (100 mL). The mixture was diluted with ether and stirred at 0° C. for 5 min, followed by room temperature for 20 min. Celite was added to aid in separation of the layers, and the resulting mixture filtered. The eluent was poured into a separatory funnel and the layers separated. The organics were washed with brine, dried over magnesium sulfate, and concentrated. The resulting residue was treated with a solution of 5 g potassium hydroxide in 100 mL methanol/water (1:1). The resulting mixture was stirred at room temperature over the weekend. The reaction was concentrated to remove most of the methanol and extracted with ether (2×) to remove byproducts (discarded). The aqueous was made acidic by addition of concentrated HCl upon which a white precipitate was formed. The precipitate was collected by filtration to afford 530 mg (66%). $^1$H NMR (CDCl$_3$) δ: 11.13 (br. s., 1H), 1.73-1.84 (m, 6H), 1.64-1.68 (m, 1H), 1.53-1.64 (m, 6H).

Intermediate 6

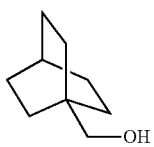

Bicyclo[2.2.2]octan-1-ylmethanol

A flask was charged with bicyclo[2.2.2]octane-1-carboxylic acid (0.375 g, 2.432 mmol) and tetrahydrofuran (3 mL). To this was added borane-tetrahydrofuran complex (1M in THF, 2.4 mL, 2.4 mmol) while cooling with a cool bath (~10° C.). The reaction was allowed to warm to room temperature overnight. The reaction was quenched by addition of 1N sodium hydroxide at 0° C. and diluted with ether. The layers were separated and the ethereal washed with brine, dried over magnesium sulfate, and concentrated to give 346 mg (quant.). Material was used without purification. $^1$H NMR (CDCl$_3$) δ: 3.24 (s, 2H), 1.55-1.61 (m, 7H), 1.34-1.44 (m, 6H), 1.23 (t, J=7.0 Hz, 1H).

Intermediate 7

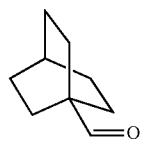

Bicyclo[2.2.2]octane-1-carbaldehyde

To a solution of bicyclo[2.2.2]octan-1-ylmethanol (0.346 g, 2.47 mmol) in dichloromethane (15 mL) at room temperature was added Dess-Martin Periodinane (1.57 g, 3.70 mmol) in two portions over 5 min. After 10 min, the reaction was diluted with several volumes of ether and treated with sodiumthiosulfate (2 g) in water (10 mL). After stirring at room temperature for 10 min, the layers were separated. The ethereal was washed with saturated sodium bicarbonate, then brine, dried over magnesium sulfate, and concentrated on the rotovap (without heat, and only till most of the ether had been removed, for fear of volatility). The residue was dissolved in a minimum of ether, transferred to a 20 mL scintillation vial, and blown down to dryness under a stream of nitrogen to give 300 mg of a viscous, near-colorless oil. The material was used without purification. $^1$H NMR (CDCl$_3$) δ: 9.42 (s, 1H), 1.62 (s, 13H).

Intermediate 8

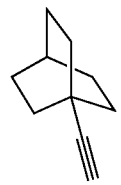

1-Ethynylbicyclo[2.2.2]octane

To a solution of bicyclo[2.2.2]octane-1-carbaldehyde (300 mg, 2.17 mmol) in methanol (5 mL) at 0° C. was added Ohira Bestmann reagent (0.424 mL, 2.82 mmol) followed by potassium carbonate (690 mg, 4.99 mmol). After 1 h, the ice bath was removed and stirring continued at room temperature for 1 h. The reaction was re-cooled to 0° C. and treated with an additional portion of potassium carbonate (500 mg) followed by an additional portion of the Ohira Bestmann reagent (0.3 mL, drop wise). After 15 min, the ice bath was removed and the reaction warmed to room temperature. The reaction was poured into ether (75 mL). The mixture was washed with water (2×), then brine, dried over magnesium sulfate, and concentrated (in a room temperature bath, only until most ether had been removed) to give 215 mg (74%) as a colorless oil. The material was used without purification. $^1$H NMR (CDCl$_3$) δ: 2.08 (s, 1H), 1.70-1.79 (m, 6H), 1.54-1.65 (m, 7H).

Intermediate 9

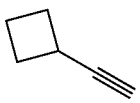

Ethynylcyclobutane

To a solution of cyclobutanecarbaldehyde (100 mg, 1.189 mmol) in methanol (2.6 mL) at 0° C. was added Ohira Bestmann reagent (232 µL, 1.545 mmol) followed by potassium carbonate (378 mg, 2.73 mmol). The ice bath was removed and stirring continued at room temperature for 1 h. The reaction was poured into ether (7 mL). The mixture was washed with water (2×), then brine, dried over magnesium sulfate, and concentrated (in a room temperature bath, only until most ether had been removed) to give the crude ethynylcyclobutane (98 mg, 1.223 mmol, 103% yield) as a colorless oil. The material was used without purification.

Intermediate 10

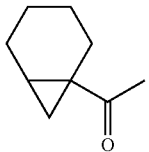

(±)-1-(Bicyclo[4.1.0]heptan-1-yl)ethanone

A dry flask was charged with sodium hydride (1.29 g, 19.3 mmol) and trimethylsulfoxonium iodide (4.25 g, 19.3 mmol). Dimethylsulfoxide (30 ml) was added drop wise over 30 min while in an ice bath. The reaction mixture was allowed to warm to room temperature and stirred for 30 min. 1-(Cyclohex-1-en-1-yl)ethanone (2 g, 16.11 mmol) in 5 mL dimethylsulfoxide was added to the reaction. The reaction was left to stir for 2 h then 1 h at 50° C. The reaction mixture was poured into ice/water and extracted with ether. The organics were dried over magnesium sulfate, filtered, and concentrated. Column chromatography (0→30% EtOAc/Hex) gave 800 mg (36%). $^1$H NMR (CDCl$_3$) δ: 2.45-2.58 (m, 1H), 2.06 (s, 3H), 1.85-1.99 (m, 1H), 1.57-1.79 (m, 4H), 1.17-1.40 (m, 4H), 0.74 (dd, J=6.8, 4.3 Hz, 1H).

Intermediate 11

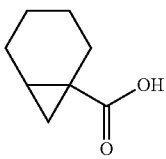

(±)-Bicyclo[4.1.0]heptane-1-carboxylic acid

A solution of sodium hydroxide (1852 mg, 46.3 mmol) and bromine (1.193 mL, 23.15 mmol) in water (15 mL) was cooled to 0° C. (±)-1-(Bicyclo[4.1.0]heptan-1-yl)ethanone (800 mg, 5.79 mmol) in dioxane (3 mL) was slowly added. Upon complete addition, the reaction was stirred at 0° C. for 1 h and then at room temperature overnight. Sodium bisulfite (151 mg, 1.447 mmol) was added and the mixture extracted with chloroform (3×) which were discarded. The aqueous was acidified with concentrated hydrochloric acid and extracted with ether. The organics were concentrated under a stream of nitrogen to afford 740 mg (91%). $^1$H NMR (CDCl$_3$) δ: 2.42-2.59 (m, 1H), 1.84-2.00 (m, 1H), 1.57-1.79 (m, 3H), 1.45 (dd, J=9.5, 4.0 Hz, 1H), 1.10-1.38 (m, 4H), 0.74 (dd, J=7.0, 4.0 Hz, 1H).

Intermediate 12

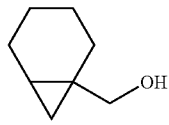

(±)-Bicyclo[4.1.0]heptan-1-ylmethanol

A flask was charged with (±)-bicyclo[4.1.0]heptane-1-carboxylic acid (740 mg, 5.28 mmol) and tetrahydrofuran (5.3 mL). To this was added borane-tetrahydrofuran complex (1 M in THF, 5.3 mL, 5.3 mmol) while cooling with a cool bath (~10° C.). The reaction was allowed to warm to room temperature overnight. The reaction was quenched by addition of 1N sodium hydroxide at 0° C. and diluted with ether. The layers were separated and the ethereal washed with brine, dried over magnesium sulfate, and concentrated to give 220 mg (33%) which was used without purification.

Intermediate 13

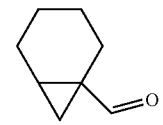

(±)-Bicyclo[4.1.0]heptane-1-carbaldehyde

To a solution of (±)-bicyclo[4.1.0]heptan-1-ylmethanol (220 mg, 1.743 mmol) in dichloromethane (10 mL) at room temperature was added Dess-Martin Periodinane (887 mg, 2.09 mmol) in two portions over 5 min. The reaction was diluted with several volumes of ether and treated with sodiumthiosulfate (2 g) in water (10 mL). After stirring at room temperature for 10 min, the layers were separated. The ethereal was washed with saturated sodium bicarbonate, then brine, dried over magnesium sulfate, and concentrated on the rotovap (without heat and only till most of the ether had been removed for fear of volatility) to give 240 mg (quant.) as an oil. The material was used without purification.

Intermediate 14

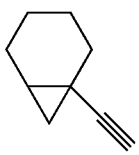

(±)-1-Ethynylbicyclo[4.1.0]heptane

To a solution of (±)-bicyclo[4.1.0]heptane-1-carbaldehyde (230 mg, 1.85 mmol) in methanol (4.1 mL) at 0° C. was added Ohira Bestmann reagent (361 μl, 2.41 mmol) followed by potassium carbonate (589 mg, 4.26 mmol). The reaction was stirred at 0° C. for 1 h, then at room temperature for 1 h. The reaction was poured into ether (7 mL). The mixture was washed with water (2×), then brine, dried over magnesium sulfate, and concentrated (in a room temperature bath, only until most ether had been removed) to give 9 mg (4%). The material was used without purification.

Intermediate 15

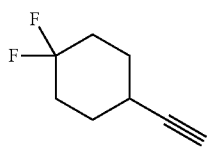

4-Ethynyl-1,1-difluorocyclohexane

Prepared according to the same procedure as (±)-1-ethynylbicyclo[4.1.0]heptane, starting with 4,4-difluorocyclohexanecarbaldehyde. Material was used without purification.

Intermediate 16

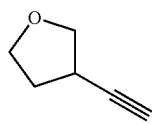

(±)-3-Ethynyltetrahydrofuran

Prepared according to the same procedure as (±)-1-ethynylbicyclo[4.1.0]heptane, starting with (±)-tetrahydrofuran-3-carbaldehyde (50% in water). Material was used without purification.

Intermediate 17

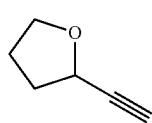

(±)-2-Ethynyltetrahydrofuran

Prepared according to the same procedure as (±)-1-ethynylbicyclo[4.1.0]heptane, starting with (±)-tetrahydrofuran-2-carbaldehyde (50% in water). Material was used without purification.

Intermediate 18

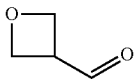

Oxetane-3-carbaldehyde

To a solution of oxetan-3-ylmethanol (215 mg, 2.440 mmol) in dichloromethane (8.1 mL) at room temperature was added Dess-Martin Periodinane (1242 mg, 2.93 mmol) in two portions over 5 min. After 10 min, the flask was fitted with a shortpath distillation head. The product distilled at ca. 110° C. to give 114 mg (54%). $^1$H NMR (CDCl$_3$) δ: 9.98 (d, J=2.3 Hz, 1H), 4.83-4.94 (m, 4H), 3.83 (ttd, J=8.3, 6.1, 2.3 Hz, 1H).

Intermediate 19

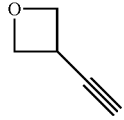

3-Ethynyloxetane

Prepared according to the same procedure as (±)-1-ethynylbicyclo[4.1.0]heptane, starting with oxetane-3-carbaldehyde. Material was used without purification.

Intermediate 20

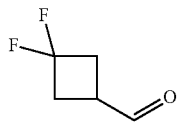

3,3-Difluorocyclobutanecarbaldehyde

To a solution of (3,3-difluorocyclobutyl)methanol (4 g, 328 mmol) in dichloromethane (109 ml) at room temperature was added Dess-Martin Periodinane (16.67 g, 39.3 mmol). After 1 h, the reaction was a faint white suspension. A small aliquot was removed, blown down under a stream of nitrogen, and analyzed by HNMR in CDCl$_3$. HNMR showed a 2.3:1.0 ratio of product to starting material. The NMR sample was returned to the larger reaction mixture. After stirring a total of 1.75 h, HNMR shows complete consumption of SM. The reaction was diluted with two volumes of ether and treated with sodiumthiosulfate (32 g) in water (160 mL). After stirring at room temperature for 10 min, the layers were separated. The ethereal was washed with saturated sodium bicarbonate (2×), dried over magnesium sulfate, and filtered. The resulting solution was concentrated via distillation of the solvent through a short path distillation apparatus. The distillation was discontinued when 6.56 g remained in the boiling flask. Integration of the $^1$H NMR showed product as 28.4 wt % (1.86 g, 47% yield). The material was directly used without further concentration. $^1$H NMR (CDCl$_3$) δ: 9.81 (t, J=1.7 Hz, 1H), 3.00-3.13 (m, 1H), 2.71-2.99 (m, 4H).

Intermediate 21

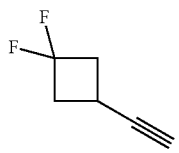

3-Ethynyl-1,1-difluorocyclobutane

To a solution of 3,3-Difluorocyclobutanecarbaldehyde (1.86 g, 15.5 mmol, in ~6 mL ether) and Ohira Bestmann Reagent (3.02 mL, 20.1 mmol) in methanol (21 mL) at 0° C. was added potassium carbonate (8.56 g, 61.9 mmol). After 2 h at 0° C., the ice bath was removed and stirring continued for 1 h. The reaction was poured into water (=60 mL) and diluted with ~150 mL pentane. The layers were separated. The organics were washed with water 2×, dried over magnesium sulfate, and filtered. The resulting colorless solution was distilled using a short path distillation head, fitted with a 12 cm vigreux column. The bulk of the material distilled at 36° C. Toward the end of the distillation, the temperature began to drop, and heating was discontinued. 2.025 g remained in the boiling flask (title compound+pentane). HNMR shows purity to be 43.5 wt % (881 mg, 49% yield).

Intermediate 22

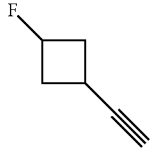

1-Ethynyl-3-fluorocyclobutane

Prepared according to the same procedure as (±)-1-ethynylbicyclo[4.1.0]heptane, starting with 3-fluorocyclobutanecarboxylic acid. Material was used without purification.

Intermediate 23

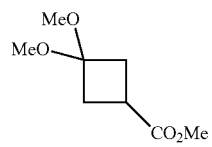

Methyl 3,3-dimethoxycyclobutanecarboxylate

To a solution of 3-oxocyclobutanecarboxylic acid (1.3 g, 11.39 mmol) in methanol (15 mL) was added trimethylorthoformate (7.5 mL, 67.8 mmol). To this was added p-toluenesulfonic acid monohydrate (2.17 g, 11.4 mmol). The reaction was warmed to reflux and held there for 2 h. The reaction was cooled to room temperature, concentrated to remove most of the methanol, diluted with ether, washed with saturated sodium bicarbonate, dried over sodium sulfate, filtered, and concentrated on the rotovap (no heat, allowing flask to get quite cold, to minimize loss due to potential volatility) to afford 0.65 g (33%). Material was used without purification.

Intermediate 24

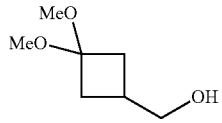

(3,3-Dimethoxycyclobutyl)methanol

To a solution of methyl 3,3-dimethoxycyclobutanecarboxylate (0.65 g, 3.73 mmol) in tetrahydrofuran (4 mL) at 0° C. was added lithium aluminum hydride (1M in THF, 4.66 mL, 4.66 mmol). After 30 min, the ice bath was removed and stirring continued for 2 h. The reaction was recooled to 0° C., quenched by the cautious addition of water (0.17 mL), then 20% potassium hydroxide (0.17 mL). The ice bath was removed, and the solids rinsed down into the resulting suspension with ether 6 mL). To this was added water (0.5 mL) and the resulting suspension stirred for 5 min. The solids were removed by filtration through celite. The resulting organics were washed with brine, dried over magnesium sulfate, filtered, and concentrated to give 580 mg (quant))$^1$H NMR (CDCl$_3$) δ: 3.72-3.83 (m, 2H), 3.68 (br. s., 1H), 3.18 (s, 3H), 3.16 (s, 3H), 2.26-2.36 (m, 2H), 1.90-1.96 (m, 1H), 1.84-1.90 (m, 2H).

Intermediate 25

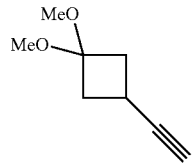

3-Ethynyl-1,1-dimethoxycyclobutane

Prepared according to the same procedure as (±)-1-ethynylbicyclo[4.1.0]heptane, starting with (3,3-dimethoxycyclobutyl)methanol. Material was used without purification. $^1$H NMR (CDCl$_3$) δ: 3.18 (s, 3H), 3.17 (s, 3H), 2.82 (td, J=8.8, 2.4 Hz, 1H), 2.52-2.60 (m, 2H), 2.22-2.29 (m, 2H), 2.16 (d, J=2.4 Hz, 1H).

Intermediate 26

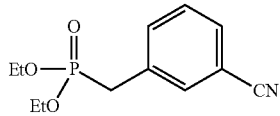 [SMILES: CCOP(=O)(Cc1cccc(C#N)c1)OCC]

Diethyl 3-cyanobenzylphosphonate

A flask was charged with 3-(bromomethyl)benzonitrile (2.0 g, 10.2 mmol) and treated with triethyl phosphite (2.68 ml, 15.3 mmol) drop wise with stirring. Upon completion of the addition, the reaction was fitted with a reflux condenser and slowly warmed to 150° C. After 2 h at 150° C., the reaction was cooled to room temperature and concentrated under high vacuum to remove most of the excess triethylphosphite. Material was used without further purification. Mass spec.: 254.04 (MH)$^+$.

Intermediate 27

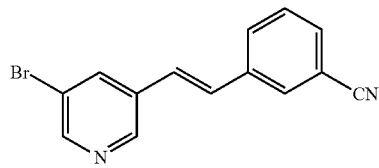 [SMILES: N#Cc1cccc(/C=C/c2cncc(Br)c2)c1]

(E)-3-(2-(5-Bromopyridin-3-yl)vinyl)benzonitrile

A solution of diethyl 3-cyanobenzylphosphonate (2.58 g, 10.2 mmol) and 5-bromonicotinaldehyde (1.897 g, 10.20 mmol) in tetrahydrofuran (40 mL) was cooled to 0° C. To this was added potassium tert-butoxide (1M in THF, 12.75 ml, 12.75 mmol) drop wise. After stirring for 30 min, the reaction was quenched by addition of saturated ammonium chloride, diluted with ether, washed with water, brine, dried over magnesium sulfate, filtered, and concentrated. The resulting solid was triturated with hexane, filtered, and pumped under high vacuum to give the title compound (2.91 g, 100%) as white solid. Mass spec.: 285.0 (MH)$^+$.

Intermediate 28

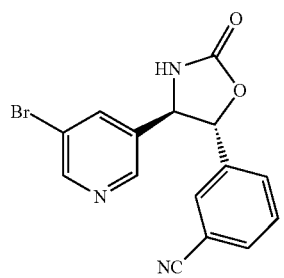 [SMILES: N#Cc1cccc([C@H]2OC(=O)N[C@@H]2c2cncc(Br)c2)c1]

3-((4R,5R)-4-(5-Bromopyridin-3-yl)-2-oxooxazolidin-5-yl)benzonitrile

To tert-butyl carbamate (1.274 g, 10.87 mmol) in 6.8 ml propanol was added a solution of sodium hydroxide (0.428 g, 10.70 mmol) in water (12.3 ml) followed by tert-butyl hypochlorite (1.21 ml, 10.7 mmol). After 5 min, the solution was cooled to 0° C., and treated with a suspension of (DHQD)$_2$PHAL (0.164 g, 0.210 mmol) and (E)-3-(2-(5-bromopyridin-3-yl)vinyl)benzonitrile (1.0 g, 3.5 mmol) in propanol (21 mL) followed by potassium osmate dihydrate (0.052 g, 0.140 mmol) as a solid in one portion. The reaction was allowed to gradually warm in the bath overnight. The reaction was quenched by addition of sodiumthiosulfate (1.4 g) in water (12 mL) and stirred for 30 min. The reaction was diluted with ether/ethyl acetate and the layers separated. The organics were washed with water (3×), then brine, dried over magnesium sulfate, and concentrated. The residue was purified by flash chromatography (50% EtOAc/Hex) to give 1.0 g as a mixture of regioisomers as a white foam solid. A portion of this material (0.50 g) was dissolved in tetrahydrofuran (12 mL), cooled to 0° C., and treated with potassium tert-butoxide (1 M in THF, 1.55 mL, 1.55 mmol) drop wise. After 5 min, the ice bath was removed and stirring continued overnight. The reaction was cooled to 0° C., quenched by addition of saturated ammonium chloride, and concentrated. The residue was dissolved in dichloromethane, washed with water, dried over magnesium sulfate, and concentrated. Column chromatography (50% EtOAc/Hex) gave 110 mg of the title compound as white solid. Mass spec.: 343.75 (MH)$^+$.

Intermediate 29

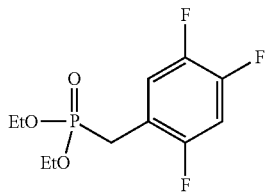 [SMILES: CCOP(=O)(Cc1cc(F)c(F)cc1F)OCC]

Diethyl 2,4,5-trifluorobenzylphosphonate

A flask was charged with 1-(bromomethyl)-2,4,5-trifluorobenzene (1.0 g, 4.44 mmol) and triethyl phosphite (1.477 g, 8.89 mmol). The flask was fitted with a reflux condenser Intermediate 30

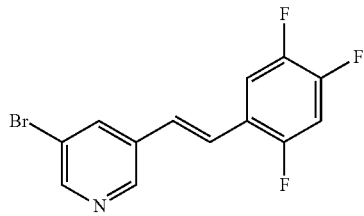 [SMILES: Fc1cc(F)c(/C=C/c2cncc(Br)c2)cc1F]

(E)-3-Bromo-5-(2,4,5-triuorostyryl)pyridine

To a solution 5-bromonicotinaldehyde (0.858 g, 4.61 mmol) and diethyl 2,4,5-trifluorobenzylphosphonate (1.24 g, 4.39 mmol) in tetrahydrofuran (21 mL) at −10° C. was added potassium tert-butoxide (1M in THF, 5.05 mL, 5.05 mmol) drop wise. After 30 min, the reaction was concentrated on the rotovap (bath temp=20° C.). The resulting residue was suspended in water and then dissolved in ethyl acetate. The layers were separated. The organics were washed with water, then brine, dried over magnesium sulfate, filtered and concentrated to give the crude product. The product was transferred to a small beaker and agitated under n-hexane (4 mL) and the organics decanted. The solid was again agitated under n-hexane (4 mL). The solid was collected in a buchner funnel, rinsed with n-hexane (2 mL), and air dried to give 1.025 g (67%) as a tan solid. $^1$H NMR (CDCl$_3$) δ: 8.63 (d, J=1.8 Hz, 1H), 8.60 (d, J=2.3 Hz, 1H), 8.00 (t, J=1.9 Hz, 1H), 7.42 (ddd, J=10.8, 8.7, 6.9 Hz, 1H), 7.21 (d, J=16.6 Hz, 1H), 6.95-7.06 (m, 2H).

Intermediate 31

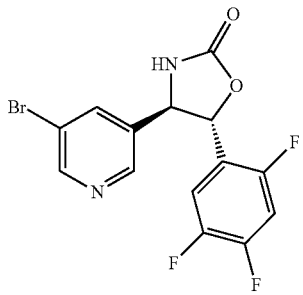 [SMILES: O=C1N[C@H](c2cncc(Br)c2)[C@@H](c2cc(F)c(F)cc2F)O1]

(4R,5R)-4-(5-Bromopyridin-3-yl)-5-(2,4,5-trifluorophenyl)oxazolidin-2-one

To a solution of tert-butyl carbamate (1.135 g, 9.68 mmol) in 1-propanol (10.65 ml) was added sodium hydroxide (0.5 M in water, 19.4 ml, 9.68 mmol), followed by tert-butyl hypochlorite (1.1 ml, 9.68 mmol). After stirring for 10 min, a solution of (DHQD)$_2$PHAL (0.075 g, 0.097 mmol) in 1-propanol (10.65 ml) was added followed by (E)-3-bromo-5-(2,4,5-trifluorostyryl)pyridine (1.014 g, 3.23 mmol) as a solid, rinsing the flask with an additional portion of 1-propanol (10.65 ml). The white mixture was cooled 0° C. To this was added potassium osmate dihydrate (0.036 g, 0.097 mmol). The reaction was allowed to gradually warm to room temperature over 3 days. The reaction was cooled to 0° C. and treated with a solution of sodium thiosulfate pentahydrate (3 g) in water (15 mL). The ice bath was removed and stirring continued for 30 min. The reaction was diluted with ethyl acetate, and the layers were separated. The organics were washed with water, then brine, dried over magnesium sulfate, filtered and concentrated. Column chromatography (25% EtOAc/Hex, 250 mL silica gel) gave partial separation of the two closely eluting spots (regioisomers). Fractions which contained primarily the first eluting regioisomer were combined to give 524 mg. This material was dissolved in tetrahydrofuran (3.4 mL), cooled to 0° C., and treated with potassium tert-butoxide (1 M in THF, 2.46 mL, 2.46 mmol). After 24 h, the reaction was treated with an additional portion of potassium tert-butoxide (1M in THF, 0.71 mL, 0.71 mmol) and stirred 5 hours longer. The reaction was concentrated on the rotovap, quenched by addition of water, and extracted with ethyl acetate (2×). The organics were washed with water, dried over magnesium sulfate, filtered, and concentrated. The resulting solid was triturated with methanol (3 very small volumes) to afford 46 mg of the title compound. $^1$H NMR (CDCl$_3$) δ: 8.75 (d, J=2.0 Hz, 1H), 8.49 (d, J=1.8 Hz, 1H), 7.94 (t, J=2.0 Hz, 1H), 7.34-7.44 (m, 1H), 7.05 (td, J=9.7, 6.3 Hz, 1H), 5.76 (s, 1H), 5.51 (d, J=5.5 Hz, 1H), 4.79 (d, J=5.5 Hz, 1H).

Intermediate 32

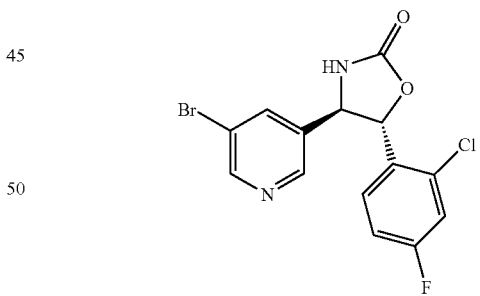

(4R,5R)-4-(5-Bromopyridin-3-yl)-5-(2-chloro-4-fluorophenyl)oxazolidin-2-one

Prepared according to the same procedure as (4R,5R)-4-(5-bromopyridin-3-yl)-5-(2,4,5-trifluorophenyl)oxazolidin-2-one, starting with 1-(bromomethyl)-2-chloro-4-fluorobenzene. $^1$H NMR (CDCl$_3$) δ: 8.74 (d, J=2.0 Hz, 1H), 8.53 (d, J=1.8 Hz, 1H), 7.97 (t, J=2.0 Hz, 1H), 7.55 (dd, J=8.7, 5.9 Hz, 1H), 7.21 (dd, J=8.3, 2.5 Hz, 1H), 7.14 (td, J=8.3, 2.5 Hz, 1H), 5.87 (s, 1H), 5.69 (d, J=4.8 Hz, 1H), 4.72 (d, J=4.8 Hz, 1H).

Example 1

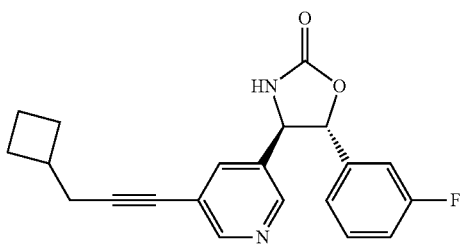 [SMILES: O=C1N[C@H](c2cncc(C#CCC3CCC3)c2)[C@@H](c2cccc(F)c2)O1]

(4R,5R)-4-(5-(3-Cyclobutylprop-1-yn-1-yl)pyridin-3-yl)-5-(3-fluorophenyl)oxazolidin-2-one A reaction vessel containing (4R,5R)-4-(5-bromopyridin-3-yl)-5-(3-fluorophenyl)oxazolidin-2-one (WO2012064603, 40.0 mg, 0.119 mmol), prop-2-yn-1-ylcyclobutane (19.0 mg, 0.202 mmol), triphenylphosphine (12.5 mg, 0.0470 mmol), and triethylamine (1.2 mL) was purged with nitrogen for 10 min before copper(I) iodide (1.81 mg, 9.49 μmol) and bis(triphenylphosphine)palladium(II) chloride (7.49 mg, 10.7 μmol) were added. The reaction vessel was then purged with nitrogen for an additional 5 min before it was placed into a preheated oil bath and stirred at 80° C. for 16 h. The volatiles were removed, and the crude material was purified using Preparative HPLC Method 9. Fractions containing the desired product were combined and dried via centrifugal evaporation to afford the title compound (13.6 mg, 33% yield). $^1$H NMR (500 MHz, DMSO-$d_6$) δ 8.59 (br. s., 1H), 8.46-8.39 (m, 2H), 7.82 (s, 1H), 7.54-7.40 (m, 1H), 7.36-7.11 (m, 3H), 5.50 (d, J=6.7 Hz, 1H), 4.93 (d, J=6.7 Hz, 1H), 2.58-2.53 (m, 3H), 2.15-2.00 (m, 2H), 1.93-1.71 (m, 4H). MS [MH]$^+$=350.9.

The compounds in Table 1 were synthesized according to the method used to prepare (4R,5R)-4-(5-(3-cyclobutylprop-1-yn-1-yl)pyridin-3-yl)-5-(3-fluorophenyl)oxazolidin-2-one using the appropriate known terminal alkyne.

TABLE 1

| Example Number | R$^1$ | LCMS Ion [MH]$^+$ | Analytical Data |
|---|---|---|---|
| 2 | ethylthiomethyl | 357.2 | $^1$H NMR (500 MHz, DMSO-$d_6$) δ 8.62 (br. s., 1H), 8.51-8.40 (m, 2H), 7.85 (s, 1H), 7.55-7.42 (m, 1H), 7.31-7.18 (m, 3H), 5.49 (d, J = 6.1 Hz, 1H), 4.94 (d, J = 6.4 Hz, 1H), 3.68 (s, 2H), 2.76-2.65 (m, 2H), 1.31-1.13 (m, 3H) |
| 3 | n-butyl | 339.4 | $^1$H NMR (500 MHz, DMSO-$d_6$) δ 8.60-8.56 (m, 1H), 8.46-8.39 (m, 2H), 7.83-7.78 (m, 1H), 7.50 (d, J = 6.4 Hz, 1H), 7.35-7.17 (m, 3H), 5.49 (d, J = 6.7 Hz, 1H), 4.93 (d, J = 7.0 Hz, 1H), 2.48 (t, J = 7.0 Hz, 2H), 1.59-1.51 (m, 2H), 1.44 (sxt, J = 7.3 Hz, 2H), 0.92 (t, J = 7.3 Hz, 3H) |
| 4 | cyclopropylmethyl | 337.1 | $^1$H NMR (500 MHz, DMSO-$d_6$) δ 8.59 (s, 1H), 8.48-8.37 (m, 2H), 7.83 (s, 1H), 7.53-7.41 (m, 1H), 7.34-7.12 (m, 3H), 5.49 (d, J = 7.0 Hz, 1H), 4.93 (d, J = 6.7 Hz, 1H), 2.55-2.51 (m, 2H), 1.08-0.89 (m, 1H), 0.55-0.46 (m, 2H), 0.32-0.17 (m, 2H) |
| 5 | isopentyl | 353.4 | $^1$H NMR (500 MHz, DMSO-$d_6$) δ 8.60 (br. s., 1H), 8.45 (m, 2H), 7.80 (s, 1H), 7.50 (d, J = 5.8 Hz, 1H), 7.33-7.19 (m, 3H), 5.49 (d, J = 7.0 Hz, 1H), 4.93 (d, J = 7.0 Hz, 1H), 2.50-2.45 (m, 2H), 1.72 (dt, J = 13.3, 6.8 Hz, 1H), 1.47 (q, J = 7.0 Hz, 2H), 0.91 (d, J = 6.7 Hz, 6H) |

TABLE 1-continued

| Example Number | R¹ | LCMS Ion [MH]⁺ | Analytical Data |
|---|---|---|---|
| 6 | (n-propyl) | 325.3 | ¹H NMR (500 MHz, DMSO-d₆) δ 8.61-8.55 (m, 1H), 8.44 (d, J = 2.1 Hz, 2H), 7.82 (s, 1H), 7.50 (d, J = 6.1 Hz, 1H), 7.36-7.19 (m, 3H), 5.49 (d, J = 7.0 Hz, 1H), 4.93 (d, J = 7.0 Hz, 1H), 2.46 (t, J = 7.0 Hz, 2H), 1.59 (sxt, J = 7.2 Hz, 2H), 1.01 (t, J = 7.3 Hz, 3H) |
| 7 | HO-CH(CH₃)-CH₂-CH₂- | 355.2ᵃ | ¹H NMR (500 MHz, DMSO-d₆) δ 8.58 (d, J = 1.5 Hz, 1H), 8.47-8.40 (m, 2H), 7.82 (s, 1H), 7.55-7.46 (m, 1H), 7.32-7.23 (m, 2H), 7.22 (d, J = 7.6 Hz, 1H), 5.49 (d, J = 6.7 Hz, 1H), 4.93 (d, J = 6.7 Hz, 1H), 4.56 (d, J = 4.9 Hz, 1H), 3.77-3.68 (m, 1H), 1.65-1.54 (m, 2H), 1.10 (d, J = 6.4 Hz, 3H)ᵇ |
| 8 | HO-CH(CH₃)-CH₂-CH₂- | 355.2ᶜ | ¹H NMR (500 MHz, DMSO-d₆) δ 8.58 (br. s., 1H), 8.48-8.34 (m, 2H), 7.81 (br. s., 1H), 7.57-7.42 (m, 1H), 7.34-7.15 (m, 3H), 5.49 (d, J = 6.4 Hz, 1H), 4.93 (d, J = 6.4 Hz, 1H), 4.56 (br. s., 1H), 3.78-3.67 (m, 1H), 1.75-1.48 (m, 2H), 1.10 (d, J = 5.8 Hz, 3H)ᵇ |
| 9 | isobutyl | 339.3 | ¹H NMR (500 MHz, DMSO-d₆) δ 8.58 (s, 1H), 8.45 (s, 1H), 8.42 (s, 1H), 7.81 (s, 1H), 7.53-7.43 (m, 1H), 7.30-7.23 (m, 2H), 7.21 (d, J = 7.3 Hz, 1H), 5.48 (d, J = 7.0 Hz, 1H), 4.92 (d, J = 6.7 Hz, 1H), 2.37 (d, J = 6.4 Hz, 2H), 1.87 (dquin, J = 13.2, 6.5 Hz, 1H), 1.00 (d, J = 6.4 Hz, 6H) |
| 10 | HO-CH(CH₃)-CH₂-CH₂- | 355.2ᵃ | ¹H NMR (500 MHz, DMSO-d₆) δ 8.57 (s, 1H), 8.44 (d, J = 7.9 Hz, 2H), 7.81 (br. s., 1H), 7.54-7.45 (m, 1H), 7.31-7.16 (m, 3H), 5.49 (d, J = 6.4 Hz, 1H), 4.92 (d, J = 6.7 Hz, 1H), 4.59 (br. s., 1H), 3.73 (d, J = 5.2 Hz, 1H), 1.65-1.53 (m, 2H), 1.13-1.06 (m, 3H)ᵇ |
| 11 | (tetrahydropyran-4-yl)methyl | 381.2 | ¹H NMR (500 MHz, DMSO-d₆) δ 8.59 (s, 1H), 8.48-8.37 (m, 2H), 7.83 (s, 1H), 7.56-7.40 (m, 1H), 7.34-7.15 (m, 3H), 5.49 (d, J = 7.0 Hz, 1H), 4.93 (d, J = 7.0 Hz, 1H), 3.92-3.77 (m, 2H), 3.34-3.22 (m, 2H), 2.48-2.40 (m, 2H), 1.84-1.63 (m, 3H), 1.40-1.26 (m, 2H) |
| 12 | CH₃-CH₂-CH(OH)-CH₂- | 355.3ᶜ | ¹H NMR (500 MHz, DMSO-d₆) δ 8.59 (s, 1H), 8.46 (s, 2H), 7.83 (s, 1H), 7.55-7.42 (m, 1H), 7.32-7.18 (m, 3H), 5.60 (br. s., 1H), 5.48 (d, J = 7.0 Hz, 1H), 4.94 (d, J = 7.0 Hz, 1H), 4.51-4.41 (m, 1H), 1.72-1.58 (m, 2H), 1.50-1.39 (m, 2H), 0.91 (t, J = 7.3 Hz, 3H) |

TABLE 1-continued

| Example Number | R¹ | LCMS Ion [MH]⁺ | Analytical Data |
|---|---|---|---|
| 13 | cyclohexylmethyl | 379.4 | ¹H NMR (500 MHz, DMSO-d₆) δ 8.60-8.54 (m, 1H), 8.48-8.37 (m, 2H), 7.82-7.76 (m, 1H), 7.56-7.42 (m, 1H), 7.32-7.15 (m, 3H), 5.48 (d, J = 6.7 Hz, 1H), 4.92 (d, J = 7.3 Hz, 1H), 2.37 (d, J = 6.7 Hz, 2H), 1.86-1.74 (m, 2H), 1.73-1.58 (m, 3H), 1.56-1.46 (m, 1H), 1.29-1.17 (m, 2H), 1.15-0.99 (m, 3H) |
| 14 | cyclobutyl(hydroxy)methyl | 367.2[c] | ¹H NMR (500 MHz, DMSO-d₆) δ 8.61 (br. s., 1H), 8.53-8.42 (m, 2H), 7.83 (s, 1H), 7.54-7.43 (m, 1H), 7.34-7.16 (m, 3H), 5.63-5.38 (m, 2H), 4.95 (d, J = 6.7 Hz, 1H), 4.41 (d, J = 6.7 Hz, 1H), 2.61-2.53 (m, 1H), 2.02-1.71 (m, 6H) |
| 15 | 1-hydroxybutyl | 355.2[a,d] | ¹H NMR (500 MHz, DMSO-d₆) δ 8.61 (s, 1H), 8.50-8.43 (m, 2H), 7.84 (br. s., 1H), 7.53-7.45 (m, 1H), 7.32-7.24 (m, 2H), 7.22 (d, J = 7.6 Hz, 1H), 5.56-5.46 (m, 2H), 4.95 (d, J = 6.7 Hz, 1H), 4.53-4.45 (m, 1H), 1.66 (quin, J = 6.9 Hz, 2H), 1.52-1.41 (m, 2H), 0.93 (t, J = 7.3 Hz, 3H) |
| 16 | 2-hydroxy-2-methylbutyl | 355.3[c] | ¹H NMR (500 MHz, DMSO-d₆) δ 8.58 (br. s., 1H), 8.50-8.41 (m, 2H), 7.83 (br. s., 1H), 7.54-7.40 (m, 1H), 7.32-7.12 (m, 3H), 5.53-5.45 (m, 2H), 4.94 (d, J = 6.7 Hz, 1H), 1.72-1.59 (m, 2H), 1.43 (s, 3H), 1.00 (t, J = 7.3 Hz, 3H) |
| 17 | 2-methoxyethyl | 341.2 | ¹H NMR (500 MHz, DMSO-d₆) δ 8.60 (s, 1H), 8.54-8.42 (m, 2H), 7.83 (br. s., 1H), 7.56-7.46 (m, 1H), 7.33-7.18 (m, 3H), 5.50 (d, J = 6.7 Hz, 1H), 4.94 (d, J = 6.7 Hz, 1H), 3.55 (t, J = 6.6 Hz, 2H), 3.31 (s, 3H), 2.77-2.69 (m, 2H) |
| 18 | 4-hydroxybutyl | 355.2 | ¹H NMR (500 MHz, DMSO-d₆) δ 8.61 (br. s., 1H), 8.49-8.37 (m, 2H), 7.85-7.75 (m, 1H), 7.49 (d, J = 6.1 Hz, 1H), 7.34-7.14 (m, 3H), 5.49 (d, J = 7.0 Hz, 1H), 4.93 (d, J = 6.1 Hz, 1H), 4.49 (br. s., 1H), 2.50-2.41 (m, 2H), 1.58 (br. s., 4H)[b] |
| 19 | 2-hydroxybutyl | 355.3[a,d] | ¹H NMR (500 MHz, DMSO-d₆) δ 8.60 (s, 1H), 8.54-8.42 (m, 2H), 7.83 (br. s., 1H), 7.56-7.46 (m, 1H), 7.33-7.18 (m, 3H), 5.50 (d, J = 6.7 Hz, 1H), 4.94 (d, J = 6.7 Hz, 1H), 3.55 (t, J = 6.6 Hz, 2H), 3.31 (s, 3H), 2.77-2.69 (m, 2H)[b] |

TABLE 1-continued

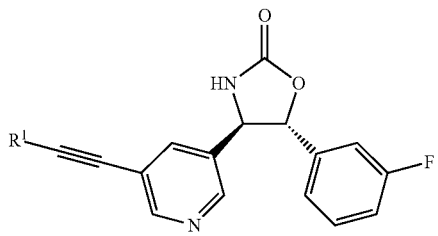

| Example Number | R[1] | LCMS Ion [MH]+ | Analytical Data |
|---|---|---|---|
| 20 | ethyl-CH(OH)-CH2- | 355.3[a,d] | $^1$H NMR (500 MHz, DMSO-d6) δ 8.59 (s, 1H), 8.49-8.38 (m, 2H), 7.83 (s, 1H), 7.55-7.44 (m, 1H), 7.34-7.16 (m, 3H), 5.49 (d, J = 7.0 Hz, 1H), 4.93 (d, J = 7.0 Hz, 1H), 4.89-4.84 (m, 1H), 3.66-3.54 (m, 1H), 2.55 (d, J = 5.8 Hz, 2H), 1.66-1.52 (m, 1H), 1.45 (dt, J = 14.0, 7.3 Hz, 1H), 0.91 (t, J = 7.3 Hz, 3H) |
| 21 | ethyl-CH(OH)-CH2- | 355.3[c] | $^1$H NMR (500 MHz, DMSO-d6) δ 8.60 (br. s., 1H), 8.45 (br. s., 2H), 7.83 (s, 1H), 7.54-7.44 (m, 1H), 7.33-7.18 (m, 3H), 5.48 (d, J = 6.7 Hz, 1H), 4.96-4.84 (m, 2H), 3.60 (br. s., 1H), 2.55 (d, J = 4.6 Hz, 2H), 1.67-1.54 (m, 1H), 1.51-1.38 (m, 1H), 0.91 (t, J = 7.3 Hz, 3H) |
| 22 | propyl-CH(OH)-CH2- | 355.2[a,d] | $^1$H NMR (500 MHz, DMSO-d6) δ 8.61 (s, 1H), 8.51-8.42 (m, 2H), 7.84 (br. s., 1H), 7.55-7.43 (m, 1H), 7.32-7.19 (m, 3H), 5.56-5.47 (m, 2H), 4.95 (d, J = 6.4 Hz, 1H), 4.49 (d, J = 6.4 Hz, 1H), 1.66 (quin, J = 6.9 Hz, 2H), 1.51-1.41 (m, 2H), 0.93 (t, J = 7.2 Hz, 3H) |
| 23 | sec-pentyl | 353.3[c] | $^1$H NMR (500 MHz, DMSO-d6) δ 8.57 (br. s., 1H), 8.48-8.38 (m, 2H), 7.81 (s, 1H), 7.54-7.45 (m, 1H), 7.31-7.17 (m, 3H), 5.49 (d, J = 7.0 Hz, 1H), 4.93 (d, J = 7.0 Hz, 1H), 2.79-2.67 (m, 1H), 1.57-1.38 (m, 4H), 1.22 (d, J = 6.7 Hz, 3H), 0.92 (t, J = 7.0 Hz, 3H) |
| 24 | PhO-CH2- | 389.3 | $^1$H NMR (500 MHz, DMSO-d6) δ 8.64 (d, J = 1.5 Hz, 1H), 8.51-8.42 (m, 2H), 7.87 (s, 1H), 7.48 (q, J = 7.3 Hz, 1H), 7.33 (t, J = 7.9 Hz, 2H), 7.28-7.23 (m, 2H), 7.20 (d, J = 7.6 Hz, 1H), 7.05 (d, J = 7.6 Hz, 2H), 7.00 (t, J = 7.3 Hz, 1H), 5.47 (d, J = 7.0 Hz, 1H), 5.08 (s, 2H), 4.93 (d, J = 7.0 Hz, 1H) |
| 25 | isobutyl-CH(OH)-CH2- | 369.4[c] | $^1$H NMR (500 MHz, DMSO-d6) δ 8.60 (s, 1H), 8.49-8.43 (m, 2H), 7.83 (s, 1H), 7.54-7.43 (m, 1H), 7.35-7.19 (m, 3H), 5.63-5.53 (m, 1H), 5.49 (d, J = 7.0 Hz, 1H), 4.95 (d, J = 7.0 Hz, 1H), 4.51 (br. s., 1H), 1.83 (dt, J = 13.5, 6.8 Hz, 1H), 1.67-1.57 (m, 1H), 1.56-1.46 (m, 1H), 0.95-0.87 (m, 6H) |
| 26 | 3-methylpyrazol-1-yl-CH2- | 377.3 | $^1$H NMR (500 MHz, DMSO-d6) δ 8.67 (d, J = 1.8 Hz, 1H), 8.54-8.44 (m, 2H), 7.93 (s, 1H), 7.79-7.71 (m, 1H), 7.53-7.47 (m, 1H), 7.33-7.10 (m, 3H), 6.09 (d, J = 1.8 Hz, 1H), 5.51 (d, J = 6.7 Hz, 1H), 5.26 (s, 2H), 4.95 (d, J = 7.0 Hz, 1H), 2.19 (s, 3H) |

TABLE 1-continued

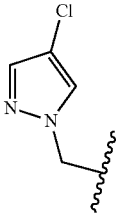

| Example Number | R[1] | LCMS Ion [MH]+ | Analytical Data |
|---|---|---|---|
| 27 | 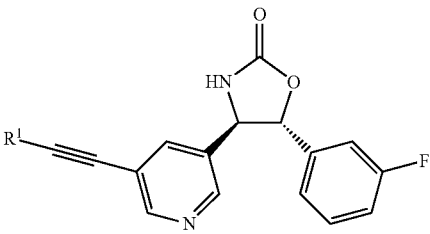 | 397.2 | $^1$H NMR (500 MHz, DMSO-d6) δ 8.69 (d, J = 1.8 Hz, 1H), 8.53 (d, J = 1.8 Hz, 1H), 8.46 (br. s., 1H), 8.17 (s, 1H), 7.95 (s, 1H), 7.65 (s, 1H), 7.55-7.42 (m, 1H), 7.34-7.17 (m, 3H), 5.51 (d, J = 6.7 Hz, 1H), 5.36 (s, 2H), 4.96 (d, J = 7.0 Hz, 1H) |
| 28 | 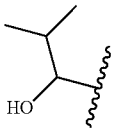 [SMILES: *C(O)C(C)C] | 355.4[c] | $^1$H NMR (500 MHz, DMSO-d6) δ 8.63 (br. s., 1H), 8.55-8.40 (m, 2H), 7.85 (s, 1H), 7.55-7.40 (m, 1H), 7.35-7.12 (m, 3H), 5.55 (br. s., 1H), 5.50 (d, J = 7.0 Hz, 1H), 4.95 (d, J = 6.7 Hz, 1H), 4.31-4.22 (m, 1H), 1.84 (dd, J = 12.8, 6.7 Hz, 1H), 0.99 (dd, J = 11.0, 6.7 Hz, 6H) |
| 29 | 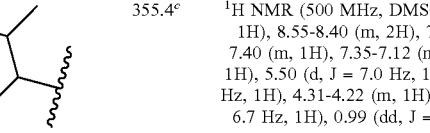 | 373.3[c] | $^1$H NMR (500 MHz, DMSO-d6) δ 8.61 (br. s., 1H), 8.52-8.39 (m, 2H), 7.86-7.80 (m, 1H), 7.54-7.41 (m, 1H), 7.35-7.11 (m, 3H), 5.50 (d, J = 7.0 Hz, 1H), 4.94 (d, J = 6.4 Hz, 1H), 2.75-2.67 (m, 2H), 2.11-1.95 (m, 1H), 1.74-1.59 (m, 1H), 1.44-1.29 (m, 1H) |
| 30 | 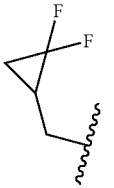 [SMILES: *CC1CC1(F)F] | 395.3[c] | $^1$H NMR (500 MHz, DMSO-d6) δ 8.64-8.57 (m, 1H), 8.50-8.42 (m, 2H), 7.85-7.77 (m, 1H), 7.55-7.44 (m, 1H), 7.34-7.12 (m, 3H), 5.50 (d, J = 6.4 Hz, 2H), 4.95 (d, J = 6.4 Hz, 1H), 4.30-4.14 (m, 1H), 1.86 (d, J = 11.6 Hz, 2H), 1.73 (d, J = 10.1 Hz, 2H), 1.66-1.57 (m, 1H), 1.54-1.45 (m, 1H), 1.28-1.02 (m, 5H) |
| 31 | 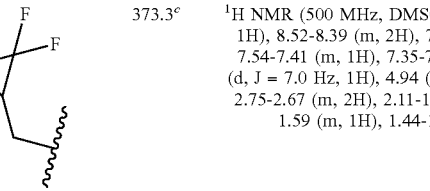 | 377.3 | $^1$H NMR (500 MHz, DMSO-d6) δ 8.65 (d, J = 1.8 Hz, 1H), 8.52-8.48 (m, 2H), 7.96 (s, 1H), 7.54-7.44 (m, 1H), 7.35 (s, 1H), 7.31-7.19 (m, 3H), 6.13-6.04 (m, 1H), 5.50 (d, J = 7.0 Hz, 1H), 5.28 (s, 2H), 4.94 (d, J = 7.0 Hz, 1H), 2.38 (s, 3H) |
| 32 | 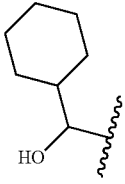 [SMILES: *C(O)C1CCCCC1] | 341.4[c] | $^1$H NMR (500 MHz, DMSO-d6) δ 8.63-8.57 (m, 1H), 8.50-8.43 (m, 2H), 7.85 (s, 1H), 7.50 (d, J = 6.1 Hz, 1H), 7.33-7.19 (m, 3H), 5.56 (br. s., 1H), 5.50 (d, J = 6.7 Hz, 1H), 4.95 (d, J = 6.7 Hz, 1H), 4.48-4.36 (m, 1H), 1.74-1.62 (m, 2H), 0.98 (t, J = 7.3 Hz, 3H) |
| 33 | 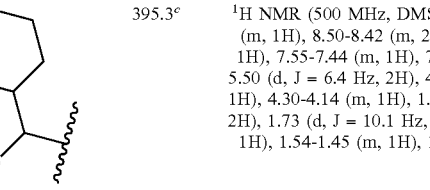 | 363.2[d] | $^1$H NMR (500 MHz, DMSO-d6) δ 8.68 (s, 1H), 8.50 (s, 1H), 8.45 (s, 1H), 7.95 (br. s., 1H), 7.79 (s, 1H), 7.55-7.46 (m, 1H), 7.35-7.24 (m, 3H), 7.22-7.16 (m, 1H), 6.96 (s, 1H), 5.49 (d, J = 6.7 Hz, 1H), 5.24 (s, 2H), 4.94 (d, J = 7.0 Hz, 1H) |

TABLE 1-continued

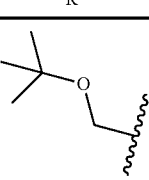

| Example Number | R¹ | LCMS Ion [MH]⁺ | Analytical Data |
|---|---|---|---|
| 34 | 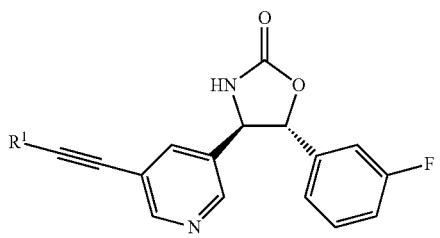 | 369.3 | ¹H NMR (500 MHz, DMSO-d₆) δ 8.63 (br. s., 1H), 8.54-8.42 (m, 2H), 7.87 (br. s., 1H), 7.49 (d, J = 5.8 Hz, 1H), 7.34-7.12 (m, 3H), 5.50 (d, J = 6.4 Hz, 1H), 4.94 (d, J = 7.0 Hz, 1H), 4.33 (s, 2H), 1.20 (s, 9H) |
| 35 | 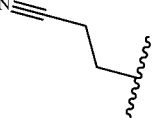 | 336.3 | ¹H NMR (500 MHz, DMSO-d₆) δ 8.64-8.59 (m, 1H), 8.53-8.43 (m, 2H), 7.88-7.82 (m, 1H), 7.55-7.44 (m, 1H), 7.33-7.24 (m, 2H), 7.22 (d, J = 7.6 Hz, 1H), 5.50 (d, J = 7.0 Hz, 1H), 4.95 (d, J = 7.0 Hz, 1H), 2.84 (s, 4H) |
| 36 | 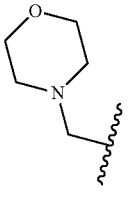 [SMILES: *CN1CCOCC1] | 382.1 | ¹H NMR (500 MHz, DMSO-d₆) δ 8.64 (s, 1H), 8.51-8.36 (m, 2H), 7.91-7.86 (m, 1H), 7.53-7.40 (m, 1H), 7.34-7.12 (m, 3H), 5.51 (d, J = 7.0 Hz, 1H), 4.94 (d, J = 7.0 Hz, 1H), 3.62 (br. s., 4H), 3.57 (s, 4H), 2.53 (s, 2H) |
| 37 | 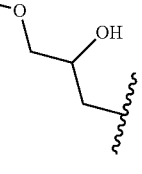 | 371.2ᶜ | ¹H NMR (500 MHz, DMSO-d₆) δ 8.59 (s, 1H), 8.48-8.38 (m, 2H), 7.83 (s, 1H), 7.54-7.46 (m, 1H), 7.32-7.14 (m, 3H), 5.49 (d, J = 7.0 Hz, 1H), 5.15 (br. s., 1H), 4.93 (d, J = 6.7 Hz, 1H), 3.87-3.78 (m, 1H), 3.37 (d, J = 5.2 Hz, 2H), 3.29 (s, 3H), 2.63-2.58 (m, 1H), 2.56-2.53 (m, 1H) |
| 38 | 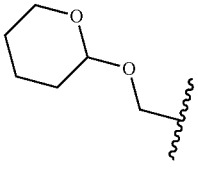 [SMILES: *COC1CCCCO1] | 397.4ᶜ | ¹H NMR (500 MHz, DMSO-d₆) δ 8.67 (br. s., 1H), 8.55-8.43 (m, 2H), 7.90 (s, 1H), 7.57-7.42 (m, 1H), 7.35-7.14 (m, 3H), 5.49 (d, J = 7.0 Hz, 1H), 4.94 (d, J = 7.0 Hz, 1H), 4.82 (br. s., 1H), 4.57-4.47 (m, 1H), 4.47-4.41 (m, 1H), 3.75 (t, J = 8.5 Hz, 2H), 1.79-1.62 (m, 2H), 1.51 (d, J = 8.5 Hz, 4H) |
| 39 | 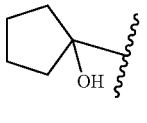 | 367.3 | ¹H NMR (500 MHz, DMSO-d₆) δ 8.59 (s, 1H), 8.50-8.41 (m, 2H), 7.83 (br. s., 1H), 7.54-7.43 (m, 1H), 7.33-7.12 (m, 3H), 5.52-5.43 (m, 2H), 4.94 (d, J = 6.4 Hz, 1H), 1.98-1.84 (m, 4H), 1.81-1.60 (m, 4H) |
| 40 | 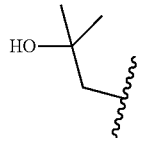 | 355.2 | ¹H NMR (500 MHz, DMSO-d₆) δ 8.61 (br. s., 1H), 8.49-8.40 (m, 2H), 7.84 (s, 1H), 7.53-7.40 (m, 1H), 7.35-7.18 (m, 3H), 5.49 (d, J = 6.4 Hz, 1H), 4.93 (d, J = 6.4 Hz, 1H), 4.69 (br. s., 1H), 2.55 (s, 2H), 1.25 (s, 6H) |
| 41 | 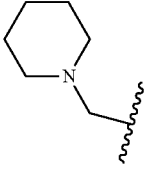 [SMILES: *CN1CCCCC1] | 380.4 | ¹H NMR (500 MHz, DMSO-d₆) δ 8.63 (br. s., 1H), 8.50-8.41 (m, 2H), 7.90-7.82 (m, 1H), 7.56-7.43 (m, 1H), 7.34-7.12 (m, 3H), 5.50 (d, J = 5.8 Hz, 1H), 4.94 (d, J = 6.4 Hz, 1H), 3.52 (s, 2H), 2.50-2.43 (m, 4H), 1.58-1.47 (m, 4H), 1.43-1.32 (m, 2H) |

TABLE 1-continued

| Example Number | R¹ | LCMS Ion [MH]⁺ | Analytical Data |
|---|---|---|---|
| 42 | (CH(OH)CH₃)CH₂– | 341.3ᶜ | ¹H NMR (500 MHz, DMSO-d₆) δ 8.59 (s, 1H), 8.48-8.39 (m, 2H), 7.83 (s, 1H), 7.52-7.44 (m, 1H), 7.31-7.16 (m, 3H), 5.48 (d, J = 6.7 Hz, 1H), 4.99-4.85 (m, 2H), 3.86 (br. s., 1H), 2.57-2.54 (m, 2H), 1.20 (d, J = 6.1 Hz, 3H) |
| 43 | benzyl | 373.3 | LCMS RT (min): 3.85 using Analytical HPLC Method 2 |
| 44 | (CH₃)₂NCH₂CH₂– | 354.2ᵈ | ¹H NMR (500 MHz, DMSO-d₆) δ 8.58 (s, 1H), 8.47-8.39 (m, 2H), 7.81 (s, 1H), 7.54-7.45 (m, 1H), 7.35-7.14 (m, 3H), 5.49 (d, J = 6.7 Hz, 1H), 4.93 (d, J = 6.4 Hz, 1H), 3.17 (s, 2H), 2.64-2.57 (m, 2H), 2.19 (s, 6H) |
| 45 | CH₃C(O)NHCH₂– | 354.1ᵈ | ¹H NMR (500 MHz, DMSO-d₆) δ 8.62 (s, 1H), 8.49 (s, 1H), 8.47-8.36 (m, 2H), 7.85 (s, 1H), 7.55-7.45 (m, 1H), 7.34-7.16 (m, 3H), 5.50 (d, J = 6.7 Hz, 1H), 4.94 (d, J = 6.7 Hz, 1H), 4.15 (d, J = 5.5 Hz, 2H), 1.86 (s, 3H) |
| 46 | 1-hydroxycyclobutyl-CH₂– | 367.5ᵈ | ¹H NMR (500 MHz, DMSO-d₆) δ 8.59 (br. s., 1H), 8.48-8.38 (m, 2H), 7.82 (s, 1H), 7.55-7.43 (m, 1H), 7.34-7.18 (m, 3H), 5.48 (d, J = 5.5 Hz, 1H), 5.30 (br. s., 1H), 4.93 (d, J = 6.4 Hz, 1H), 2.68 (s, 2H), 2.13-1.95 (m, 4H), 1.75-1.61 (m, 1H), 1.59-1.47 (m, 1H) |
| 47 | (2-oxopyrrolidin-1-yl)CH₂– | 380.2ᵉ | ¹H NMR (500 MHz, DMSO-d₆) δ 8.65 (br. s., 1H), 8.53-8.38 (m, 2H), 7.92 (s, 1H), 7.53-7.42 (m, 1H), 7.33-7.12 (m, 3H), 5.50 (d, J = 6.7 Hz, 1H), 4.93 (d, J = 6.4 Hz, 1H), 4.32 (br. s., 2H), 3.51-3.43 (m, 2H), 2.34-2.18 (m, 2H), 2.06-1.91 (m, 2H) |
| 48 | F₃CC(O)NHCH₂– | 408.2ᵈ | ¹H NMR (500 MHz, DMSO-d₆) δ 10.13 (br. s., 1H), 8.65 (s, 1H), 8.55-8.50 (m, 1H), 8.46 (s, 1H), 7.89 (s, 1H), 7.56-7.41 (m, 1H), 7.32-7.16 (m, 3H), 5.50 (d, J = 6.7 Hz, 1H), 4.95 (d, J = 6.7 Hz, 1H), 4.34 (s, 2H) |

TABLE 1-continued

| Example Number | R¹ | LCMS Ion [MH]⁺ | Analytical Data |
|---|---|---|---|
| 49 | indazol-1-ylmethyl | 413.3 | ¹H NMR (500 MHz, DMSO-d₆) δ 8.63 (d, J = 1.5 Hz, 1H), 8.49 (d, J = 1.8 Hz, 1H), 8.43 (br. s., 1H), 8.17 (s, 1H), 7.87 (s, 1H), 7.83 (d, J = 8.5 Hz, 2H), 7.48 (t, J = 7.5 Hz, 2H), 7.31-7.12 (m, 4H), 5.69 (s, 2H), 5.48 (d, J = 6.7 Hz, 1H), 4.93 (d, J = 6.7 Hz, 1H) |
| 50 | isobutyl | 325.2 | ¹H NMR (500 MHz, DMSO-d₆) δ 8.60 (br. s., 1H), 8.47-8.43 (m, 1H), 7.80 (s, 1H), 7.55-7.44 (m, 1H), 7.30-7.17 (m, 4H), 5.47 (d, J = 6.7 Hz, 1H), 4.92 (d, J = 7.0 Hz, 1H), 2.84 (dt, J = 13.7, 6.8 Hz, 1H), 1.22 (d, J = 6.7 Hz, 6H) |
| 51 | n-pentyl | 353.3ᶠ | ¹H NMR (500 MHz, DMSO-d₆) δ 8.58 (br. s., 1H), 8.47-8.39 (m, 2H), 7.80 (br. s., 1H), 7.53-7.45 (m, 1H), 7.31-7.19 (m, 3H), 5.49 (d, J = 5.8 Hz, 1H), 4.93 (d, J = 6.4 Hz, 1H), 2.48 (d, J = 6.7 Hz, 2H), 1.61-1.51 (m, 2H), 1.44-1.28 (m, 4H), 0.93-0.83 (m, 3H) |
| 52 | F₃C-CH₂-O-CH₂- | 395.1ᵍ | ¹H NMR (500 MHz, DMSO-d₆) δ 8.70 (s, 1H), 8.53 (s, 1H), 8.47 (br. s., 1H), 7.96 (br. s., 1H), 7.53-7.44 (m, 1H), 7.32-7.19 (m, 3H), 5.51 (d, J = 7.0 Hz, 1H), 4.95 (d, J = 7.0 Hz, 1H), 4.64 (s, 2H), 4.25-4.15 (m, 2H) |
| 53 | EtO-CH₂- | 341.3ᶠ | ¹H NMR (500 MHz, DMSO-d₆) δ 8.66 (s, 1H), 8.52-8.42 (m, 2H), 7.91 (s, 1H), 7.54-7.42 (m, 1H), 7.33-7.17 (m, 3H), 5.50 (d, J = 7.0 Hz, 1H), 4.94 (d, J = 7.0 Hz, 1H), 4.40 (s, 2H), 3.57 (q, J = 6.9 Hz, 2H), 1.16 (t, J = 7.0 Hz, 3H) |
| 54 | (4-methylpyrazol-1-yl)methyl | 377.3 | ¹H NMR (500 MHz, DMSO-d₆) δ 8.67 (d, J = 1.8 Hz, 1H), 8.52 (d, J = 1.8 Hz, 1H), 8.46 (s, 1H), 7.92 (s, 1H), 7.65 (s, 1H), 7.56-7.46 (m, 1H), 7.36-7.18 (m, 4H), 5.51 (d, J = 7.0 Hz, 1H), 5.27 (s, 2H), 4.95 (d, J = 7.0 Hz, 1H), 2.04 (s, 3H) |
| 55 | EtO-CH₂CH₂- | 355.3ᶠ | ¹H NMR (500 MHz, DMSO-d₆) δ 8.58 (s, 1H), 8.48-8.41 (m, 2H), 7.81 (s, 1H), 7.53-7.45 (m, 1H), 7.33-7.14 (m, 3H), 5.48 (d, J = 7.0 Hz, 1H), 4.93 (d, J = 6.7 Hz, 1H), 3.57 (t, J = 6.6 Hz, 2H), 3.52-3.48 (m, 2H), 2.71 (t, J = 6.6 Hz, 2H), 1.12 (t, J = 7.0 Hz, 3H) |

TABLE 1-continued

| Example Number | R¹ | LCMS Ion [MH]⁺ | Analytical Data |
|---|---|---|---|
| 56 | (1-hydroxypentyl) | 369.3[a,h] | ¹H NMR (500 MHz, DMSO-d₆) δ 8.62 (br. s., 1H), 8.46 (br. s., 2H), 7.82 (br. s., 1H), 7.55-7.41 (m, 1H), 7.33-7.17 (m, 3H), 5.60 (d, J = 5.8 Hz, 1H), 5.48 (d, J = 6.7 Hz, 1H), 4.94 (d, J = 6.7 Hz, 1H), 4.51-4.38 (m, 1H), 1.65 (d, J = 6.7 Hz, 2H), 1.46-1.26 (m, 4H), 0.88 (t, J = 7.0 Hz, 3H) |
| 57 | (cyclopropyl-hydroxymethyl) | 353.2[a,f] | ¹H NMR (500 MHz, DMSO-d₆) δ 8.61 (s, 1H), 8.52-8.36 (m, 2H), 7.85 (br. s., 1H), 7.56-7.43 (m, 1H), 7.32-7.17 (m, 3H), 5.63 (br. s., 1H), 5.50 (d, J = 6.7 Hz, 1H), 4.95 (d, J = 7.0 Hz, 1H), 4.20 (d, J = 6.4 Hz, 1H), 1.27-1.14 (m, 1H), 0.53-0.44 (m, 2H), 0.44-0.34 (m, 2H) |
| 58 | (cyclopropyl-hydroxymethyl) | 353.2[c,f] | ¹H NMR (500 MHz, DMSO-d₆) δ 8.62 (br. s., 1H), 8.54-8.42 (m, 2H), 7.83 (s, 1H), 7.57-7.43 (m, 1H), 7.30-7.18 (m, 3H), 5.69 (d, J = 5.8 Hz, 1H), 5.48 (d, J = 7.0 Hz, 1H), 4.94 (d, J = 7.0 Hz, 1H), 4.19 (t, J = 6.3 Hz, 1H), 1.24-1.13 (m, 1H), 0.53-0.45 (m, 2H), 0.43-0.35 (m, 2H) |
| 59 | (cyclopropyl-hydroxymethyl) | 353.2[a,f] | ¹H NMR (500 MHz, DMSO-d₆) δ 8.60 (s, 1H), 8.52-8.39 (m, 2H), 7.84 (br. s., 1H), 7.61-7.39 (m, 1H), 7.33-7.14 (m, 3H), 5.65 (br. s., 1H), 5.49 (d, J = 6.7 Hz, 1H), 4.94 (d, J = 6.7 Hz, 1H), 4.22-4.12 (m, 1H), 1.25-1.13 (m, 1H), 0.55-0.44 (m, 2H), 0.44-0.32 (m, 2H) |
| 60 | (methoxymethyl) | 327.2[f] | ¹H NMR (500 MHz, DMSO-d₆) δ 8.65 (s, 1H), 8.53-8.40 (m, 2H), 7.90 (s, 1H), 7.55-7.43 (m, 1H), 7.31-7.15 (m, 3H), 5.49 (d, J = 7.0 Hz, 1H), 4.94 (d, J = 7.0 Hz, 1H), 4.36 (s, 2H), 3.34 (s, 3H) |
| 61 | (tert-butyl) | 339.3[f] | ¹H NMR (500 MHz, DMSO-d₆) δ 8.54 (br. s., 1H), 8.46-8.36 (m, 2H), 7.80 (br. s., 1H), 7.52-7.45 (m, 1H), 7.31-7.17 (m, 3H), 5.48 (d, J = 6.4 Hz, 1H), 4.92 (d, J = 7.0 Hz, 1H), 1.31 (s, 9H) |
| 62 | (pyrazol-1-ylmethyl) | 363.5 | ¹H NMR (500 MHz, DMSO-d₆) δ 8.65 (s, 1H), 8.47 (d, J = 18.3 Hz, 2H), 7.89 (d, J = 15.0 Hz, 2H), 7.56-7.45 (m, 2H), 7.33-7.15 (m, 3H), 6.32 (s, 1H), 5.48 (d, J = 6.7 Hz, 1H), 5.34 (s, 2H), 4.93 (d, J = 7.0 Hz, 1H) |

[a]Single diastereomer. Diastereomers were separated using chiral preparative HPLC; [b]Signals hidden behind solvent and residual water peaks; [c]Diastereomeric mixture; [d]Reaction heated for 4 h; [e]Reaction heated for 2 h; [f]Reaction heated to 85° C. for 20 h; [g]Reaction heated to 85° C. for 4 days; [h]Reaction heated to 85° C. for 3 days.

Example 63

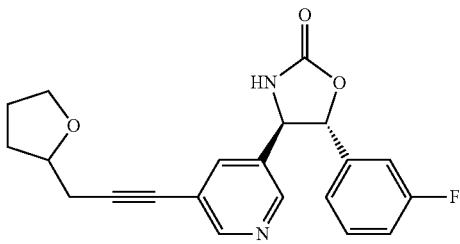 [SMILES: O=C1N[C@H](c2cncc(C#CCC3CCCO3)c2)[C@@H](c2cccc(F)c2)O1]

((4R,5R)-5-(3-Fluorophenyl)-4-(5-(3-(tetrahydro-furan-2-yl)prop-1-yn-1-yl)pyridin-3-yl)oxazolidin-2-one Following the synthetic procedure for (4R,5R)-4-(5-(3-cyclobutylprop-1-yn-1-yl)pyridin-3-yl)-5-(3-fluorophenyl) oxazolidin-2-one, (±)-2-(prop-2-yn-1-yl)tetrahydrofuran (22.2 mg, 0.202 mmol) and (4R,5R)-4-(5-bromopyridin-3-yl)-5-(3-fluorophenyl)oxazolidin-2-one (WO2012064603, 40.0 mg, 0.119 mmol) were coupled to afford a diastereomeric mixture of ((4R,5R)-5-(3-fluorophenyl)-4-(5-(3-(tetrahydrofuran-2-yl)prop-1-yn-1-yl)pyridin-3-yl)oxazolidin-2-one (7.70 mg, 18% yield). $^1$H NMR (500 MHz, DMSO-d$_6$) δ 8.59 (s, 1H), 8.48-8.36 (m, 2H), 7.82 (s, 1H), 7.55-7.42 (m, 1H), 7.33-7.14 (m, 3H), 5.50 (d, J=6.7 Hz, 1H), 4.94 (d, J=7.0 Hz, 1H), 4.07-3.96 (m, 1H), 3.87-3.76 (m, 1H), 3.72-3.59 (m, 1H), 2.67 (d, J=5.5 Hz, 2H), 2.10-1.98 (m, 1H), 1.97-1.77 (m, 2H), 1.75-1.59 (m, 1H). MS (LC/MS) [MH]$^+$=367.3.

The compounds in Table 2 were synthesized by the method used to prepare ((4R,5R)-5-(3-fluorophenyl)-4-(5-(3-(tetrahydrofuran-2-yl)prop-1-yn-1-yl)pyridin-3-yl)oxazolidin-2-one, using the appropriate known terminal alkyne.

TABLE 2

| Example Number | R$^1$ | LCMS Ion [MH]$^+$ | Analytical Data |
|---|---|---|---|
| 64 | | 367.2$^a$ | $^1$H NMR (500 MHz, DMSO-d6) δ 8.59 (br. s., 1H), 8.47-8.35 (m, 2H), 7.84 (s, 1H), 7.54-7.42 (m, 1H), 7.34-7.13 (m, 3H), 5.49 (d, J = 5.8 Hz, 1H), 4.92 (d, J = 6.4 Hz, 1H), 3.85-3.65 (m, 4H), 2.59-2.53 (m, 2H), 2.47-2.40 (m, 1H), 2.11-1.99 (m, 1H), 1.74-1.60 (m, 1H) |
| 65 | | 367.3$^b$ | $^1$H NMR (500 MHz, DMSO-d6) δ 8.60 (d, J = 1.5 Hz, 1H), 8.45 (s, 2H), 7.85 (s, 1H), 7.54-7.42 (m, 1H), 7.33-7.17 (m, 3H), 5.50 (d, J = 6.7 Hz, 1H), 4.93 (d, J = 7.0 Hz, 1H), 3.86-3.73 (m, 2H), 3.68 (q, J = 7.8 Hz, 1H), 3.46 (dd, J = 8.2, 6.1 Hz, 1H), 2.60-2.54 (m, 2H), 2.48-2.41 (m, 1H), 2.13-1.91 (m, 1H), 1.74-1.56 (m, 1H) |
| 66 | | 367.3$^b$ | $^1$H NMR (500 MHz, DMSO-d6) δ 8.60 (d, J = 1.5 Hz, 1H), 8.45 (s, 2H), 7.85 (s, 1H), 7.58-7.41 (m, 1H), 7.33-7.15 (m, 3H), 5.50 (d, J = 6.7 Hz, 1H), 4.93 (d, J = 7.0 Hz, 1H), 3.86-3.72 (m, 2H), 3.68 (q, J = 7.8 Hz, 1H), 3.46 (dd, J = 8.2, 6.1 Hz, 1H), 2.62-2.54 (m, 2H), 2.48-2.40 (m, 1H), 2.12-1.98 (m, 1H), 1.68 (dq, J = 13.0, 6.7 Hz, 1H) |
| 67 | F$_3$C | 409.1 | $^1$H NMR (500 MHz, DMSO-d6) δ 8.60 (s, 1H), 8.55-8.50 (m, 1H), 8.49-8.44 (m, 1H), 7.83 (s, 1H), 7.54-7.47 (m, 1H), 7.33-7.18 (m, 3H), 5.50 (d, J = 6.7 Hz, 1H), 4.95 (d, J = 7.0 Hz, 1H), 4.16 (q, J = 9.5 Hz, 2H), 3.81 (t, J = 6.6 Hz, 2H), 2.80 (t, J = 6.4 Hz, 2H) |

TABLE 2-continued

| Example Number | R¹ | LCMS Ion [MH]⁺ | Analytical Data |
|---|---|---|---|
| 68 | (oxetan-3-ylmethyl group) | 353.3[c] | LCMS RT (min): 3.14 using Analytical HPLC Method 2 |
| 69 | (oxetan-2-ylmethyl group) | 353.2[a] | ¹H NMR (500 MHz, DMSO-d6) δ 8.62 (br. s., 1H), 8.50-8.36 (m, 2H), 7.84 (br. s., 1H), 7.49 (br. s., 1H), 7.33-7.17 (m, 3H), 5.49 (br. s., 1H), 4.98-4.83 (m, 2H), 4.59-4.42 (m, 2H), 2.91-2.81 (m, 2H), 1.86 (d, J = 4.9 Hz, 2H) |

[a]Diastereomeric mixture; [b]Single diastereomer. Diastereomers were separated using chiral preparatory HPLC. [c]Reaction heated for 2 h.

Example 70

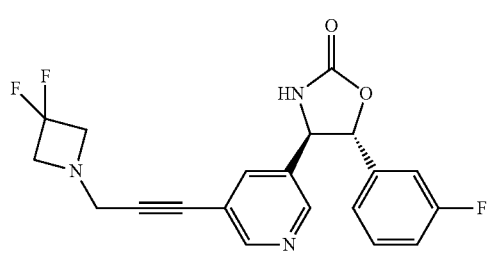 [SMILES: O=C1N[C@H](c2cncc(C#CCN3CC(F)(F)C3)c2)[C@@H](c2cccc(F)c2)O1]

(4R,5R)-4-(5-(3-(3,3-Difluoroazetidin-1-yl)prop-1-yn-1-yl)pyridin-3-yl)-5-(3-fluorophenyl)oxazolidin-2-one Following the synthetic procedure for (4R,5R)-4-(5-(3-cyclobutylprop-1-yn-1-yl)pyridin-3-yl)-5-(3-fluorophenyl)oxazolidin-2-one, 3,3-difluoro-1-(prop-2-yn-1-yl)azetidine (26.4 mg, 0.202 mmol) and (4R,5R)-4-(5-bromopyridin-3-yl)-5-(3-fluorophenyl)oxazolidin-2-one (WO2012064603, 40.0 mg, 0.119 mmol) were coupled to afford (4R,5R)-4-(5-(3-(3,3-difluoroazetidin-1-yl)prop-1-yn-1-yl)pyridin-3-yl)-5-(3-fluorophenyl)oxazolidin-2-one (2.80 mg, 6% yield). ¹H NMR (500 MHz, DMSO-d6) δ 8.67 (s, 1H), 8.53-8.44 (m, 2H), 7.94-7.87 (m, 1H), 7.54-7.46 (m, 1H), 7.33-7.11 (m, 3H), 5.50 (d, J=6.7 Hz, 1H), 4.95 (d, J=6.7 Hz, 1H), 3.78-3.68 (m, 6H). MS (LC/MS) [MH]⁺=388.3.

Example 71

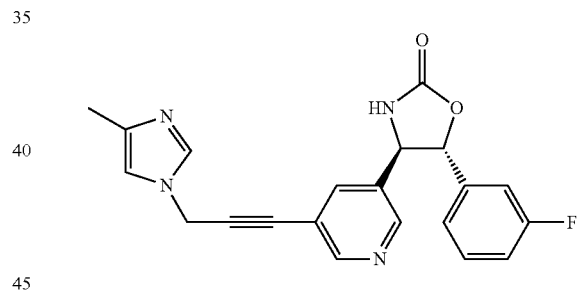

(4R,5R)-5-(3-Fluorophenyl)-4-(5-(3-(4-methyl-M-imidazol-1-yl)prop-1-yn-1-yl)pyridin-3-yl)oxazolidin-2-one Following the synthetic procedure for (4R,5R)-4-(5-(3-cyclobutylprop-1-yn-1-yl)pyridin-3-yl)-5-(3-fluorophenyl)oxazolidin-2-one, 4-methyl-1-(prop-2-yn-1-yl)-1H-imidazole (30.3 mg, 0.252 mmol) and (4R,5R)-4-(5-bromopyridin-3-yl)-5-(3-fluorophenyl)oxazolidin-2-one (WO2012064603, 50.0 mg, 0.148 mmol) were coupled to afford (4R,5R)-5-(3-fluorophenyl)-4-(5-(3-(4-methyl-1H-imidazol-1-yl)prop-1-yn-1-yl)pyridin-3-yl)oxazolidin-2-one (3.20 mg, 6% yield). ¹H NMR (500 MHz, DMSO-d6) δ 8.69 (d, J=1.8 Hz, 1H), 8.52 (d, J=1.8 Hz, 1H), 8.46 (br. s., 1H), 7.96 (s, 1H), 7.64 (s, 1H), 7.53-7.45 (m, 1H), 7.36-7.15 (m, 3H), 7.01 (s, 1H), 5.51 (d, J=7.0 Hz, 1H), 5.17 (s, 2H), 4.95 (d, J=7.0 Hz, 1H), 2.11 (s, 3H). MS (LC/MS) [MH]⁺=377.2.

Example 72

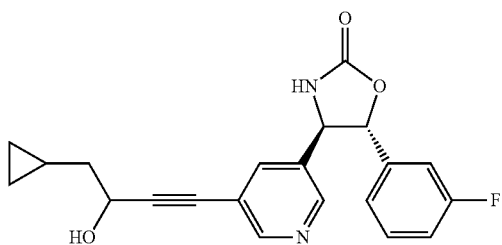 [SMILES: O=C1N[C@H](c2cncc(C#CC(O)CC3CC3)c2)[C@@H](c2cccc(F)c2)O1]

(4R,5R)-4-(5-(4-Cyclopropyl-3-hydroxybut-1-yn-1-yl)pyridin-3-yl)-5-(3-fluorophenyl)oxazolidin-2-one Following the synthetic procedure for (4R,5R)-4-(5-(3-cyclobutylprop-1-yn-1-yl)pyridin-3-yl)-5-(3-fluorophenyl)oxazolidin-2-one, 1-cyclopropylbut-3-yn-2-ol (45.6 mg, 0.414 mmol) and (4R,5R)-4-(5-bromopyridin-3-yl)-5-(3-fluorophenyl)oxazolidin-2-one (WO2012064603, 140 mg, 0.414 mmol) were coupled at 85° C. for 20 h to afford a diastereomeric mixture of (4R,5R)-4-(5-(4-cyclopropyl-3-hydroxybut-1-yn-1-yl)pyridin-3-yl)-5-(3-fluorophenyl)oxazolidin-2-one (27.5 mg, 18% yield). $^1$H NMR (500 MHz, DMSO-d6) δ 8.60 (br. s., 1H), 8.50-8.42 (m, 2H), 7.83 (br. s., 1H), 7.53-7.43 (m, 1H), 7.32-7.16 (m, 3H), 5.66-5.58 (m, 1H), 5.49 (d, J=6.7 Hz, 1H), 4.94 (d, J=6.1 Hz, 1H), 4.55-4.45 (m, 1H), 1.67-1.48 (m, 2H), 0.94-0.80 (m, 1H), 0.49-0.38 (m, 2H), 0.18-0.06 (m, 2H). MS (LC/MS) [MH]$^+$= 367.3.

The compounds in Table 3 were synthesized using the method used to prepare (4R,5R)-4-(5-(4-cyclopropyl-3-hydroxybut-1-yn-1-yl)pyridin-3-yl)-5-(3-fluorophenyl)oxazolidin-2-one, using the appropriate known terminal alkyne.

TABLE 3

| Example Number | R$^1$ | LCMS Ion [MH]$^+$ | $^1$H NMR |
|---|---|---|---|
| 73 | (cyclopropyl-CH$_2$-CH(OH)-) | 367.2[a] | $^1$H NMR (500 MHz, DMSO-d6) δ 8.60 (s, 1H), 8.52-8.43 (m, 2H), 7.83 (br. s., 1H), 7.55-7.42 (m, 1H), 7.35-7.08 (m, 3H), 5.49 (d, J = 6.4 Hz, 1H), 4.94 (d, J = 6.7 Hz, 1H), 4.50 (t, J = 6.6 Hz, 1H), 1.67-1.48 (m, 2H), 0.93-0.78 (m, 1H), 0.51-0.36 (m, 2H), 0.22-0.06 (m, 2H)[b] |
| 74 | (cyclopropyl-CH$_2$-CH(OH)-) | 367.3[a] | $^1$H NMR (500 MHz, DMSO-d$_6$) δ 8.61 (s, 1H), 8.51-8.43 (m, 2H), 7.84 (br. s., 1H), 7.54-7.45 (m, 1H), 7.34-7.14 (m, 3H), 5.65 (br. s, 1H), 5.50 (d, J = 6.7 Hz, 1H), 4.95 (d, J = 7.0 Hz, 1H), 4.51 (t, J = 6.9 Hz, 1H), 1.68-1.48 (m, 2H), 0.95-0.80 (m, 1H), 0.50-0.35 (m, 2H), 0.22-0.05 (m, 2H) |
| 75 | (cyclopropyl-CH(OH)-CH(CH$_3$)-) | 367.4[c] | $^1$H NMR (500 MHz, DMSO-d6) δ 8.61 (br. s., 1H), 8.52-8.37 (m, 2H), 7.84 (br. s., 1H), 7.56-7.44 (m, 1H), 7.39-7.14 (m, 3H), 5.58 (br. s., 1H), 5.50 (d, J = 6.7 Hz, 1H), 4.95 (d, J = 6.4 Hz, 1H), 4.30-4.12 (m, 1H), 1.03 (d, J = 2.7 Hz, 3H), 0.96-0.88 (m, 1H), 0.87-0.75 (m, 1H), 0.60-0.50 (m, 1H), 0.32-0.16 (m, 1H) |
| 76 | (2,2-difluorocyclopropyl-CH(OH)-) | 389.3[c] | $^1$H NMR (500 MHz, DMSO-d6) δ 8.64 (br. s., 1H), 8.55-8.39 (m, 2H), 7.89 (br. s., 1H), 7.58-7.42 (m, 1H), 7.33-7.16 (m, 3H), 5.51 (d, J = 6.4 Hz, 1H), 4.96 (d, J = 6.4 Hz, 1H), 4.36 (d, J = 8.5 Hz, 1H), 2.18 (br. s., 1H), 1.79-1.63 (m, 1H), 1.53 (br. s., 1H)[b] |

TABLE 3-continued

| Example Number | R¹ | LCMS Ion [MH]⁺ | ¹H NMR |
|---|---|---|---|
| 77 | (HO-cyclopropyl-CH) | 381.4[a] | ¹H NMR (500 MHz, DMSO-d6) δ 8.60 (br. s., 1H), 8.54-8.43 (m, 2H), 7.82 (br. s., 1H), 7.55-7.41 (m, 1H), 7.35-7.19 (m, 3H), 5.49 (br. s., 1H), 4.95 (br. s., 1H), 4.06 (d, J = 9.5 Hz, 1H), 1.17-1.09 (m, 3H), 1.08-1.00 (m, 3H)[b] |
| 78 | (HO-cyclopropyl-CH) | 381.4[a] | ¹H NMR (500 MHz, DMSO-d6) δ 8.59 (br. s., 1H), 8.54-8.43 (m, 2H), 7.82 (br. s., 1H), 7.55-7.45 (m, 1H), 7.32-7.16 (m, 3H), 5.50 (d, J = 6.1 Hz, 1H), 4.95 (d, J = 5.2 Hz, 1H), 4.06 (d, J = 9.5 Hz, 1H), 1.18-1.10 (m, 3H), 1.08-1.00 (m, 3H)[b] |

[a]Single diastereomer. Diastereomers were separated using chiral preparatory HPLC; [b]Signals hidden behind solvent and residual water peaks; [c]Diastereomeric mixture.

Example 79

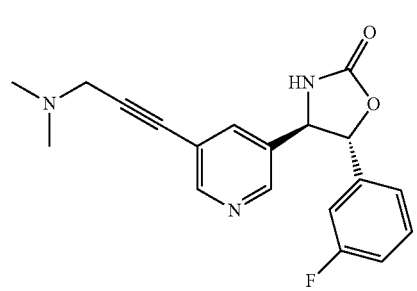 [SMILES: CN(C)CC#Cc1cncc([C@H]2NC(=O)O[C@@H]2c2cccc(F)c2)c1]

(4R,5R)-4-(5-(3-(Dimethylamino)prop-1-yn-1-yl) pyridin-3-yl)-5-(3-fluorophenyl)oxazolidin-2-one A suspension of (4R,5R)-4-(5-bromopyridin-3-yl)-5-(3-fluorophenyl)oxazolidin-2-one (WO2012064603) (50 mg, 0.148 mmol) and N,N-dimethylprop-2-yn-1-amine (12.3 mg, 0.148 mmol) in triethylamine (3 mL) was purged with nitrogen for 20 min. Triphenylphosphine (11.7 mg, 0.044 mmol), copper(I) iodide (0.57 mg, 3.0 μmol), and bis(triphenylphosphine)palladium chloride (2.1 mg, 3.0 μmol) was then added. The tube was capped and the suspension heated at 90° C. for 5 h. The reaction was cooled to room temperature, diluted with ethyl acetate, washed with water then brine, dried over magnesium sulfate, filtered, and concentrated. The residue was purified by Prep HPLC (Xterra C18 column, 10%→100% MeOH/H2O, 0.1% TFA) to give 58 mg (69%) as a TFA salt. ¹H NMR (CD₃OD) δ: 8.72 (d, J=1.8 Hz, 1H), 8.52 (d, J=2.0 Hz, 1H), 8.04 (t, J=2.0 Hz, 1H), 7.39-7.51 (m, 1H), 7.10-7.22 (m, 3H), 5.42 (d, J=7.3 Hz, 1H), 4.94 (d, J=7.1 Hz, 1H), 4.36 (s, 2H), 3.02 (s, 6H). Mass spec.: 340.18 (MH)⁺.

Example 80

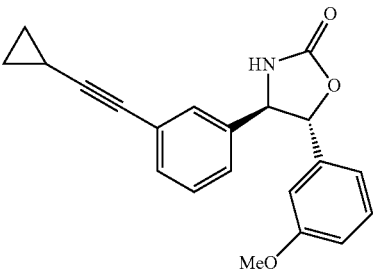 [SMILES: COc1cccc([C@H]2OC(=O)N[C@@H]2c2cccc(C#CC3CC3)c2)c1]

(4R,5R)-4-(3-(Cyclopropylethynyl)phenyl)-5-(3-methoxyphenyl)oxazolidin-2-one

Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(3-bromophenyl)-5-(3-methoxyphenyl)oxazolidin-2-one (WO2012064603) and ethynylcyclopropane. ¹H NMR (CDCl₃) δ: 7.38-7.44 (m, 2H), 7.33 (td, J=7.9, 3.2 Hz, 2H), 7.20 (d, J=7.6 Hz, 1H), 6.91-6.97 (m, 1H), 6.82-6.88 (m, 2H), 5.62 (s, 1H), 5.28 (d, J=7.3 Hz, 1H), 4.71 (d, J=7.3 Hz, 1H), 3.83 (s, 3H), 1.47 (tt, J=8.2, 5.0 Hz, 1H), 0.80-0.96 (m, 4H). Mass spec.: 334.0 (MH)⁺.

Example 81

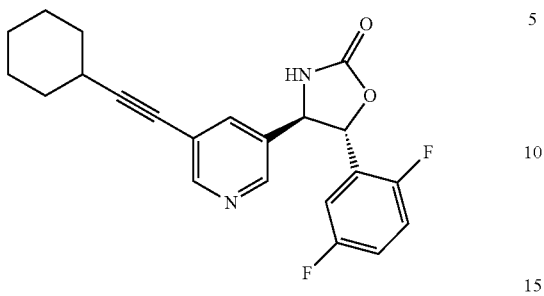

(4R,5R)-4-(5-(Cyclohexylethynyl)pyridin-3-yl)-5-(2,5-difluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(2,5-difluorophenyl)oxazolidin-2-one (WO2012064603) and ethynylcyclohexane. $^1$H NMR (DMSO-$d_6$) δ: 8.58 (d, J=1.5 Hz, 1H), 8.51 (bs, 1H), 8.47 (s, 1H), 7.86 (s, 1H), 7.18-7.50 (m, 3H), 5.63 (d, J=6.7 Hz, 1H), 4.99 (d, J=6.4 Hz, 1H), 2.62-2.80 (m, 1H), 1.77-1.94 (m, 2H), 1.61-1.76 (m, 2H), 1.50 (d, J=9.5 Hz, 3H), 1.24-1.42 (m, 3H). Mass spec.: 383.3 (MH)$^+$.

Example 82

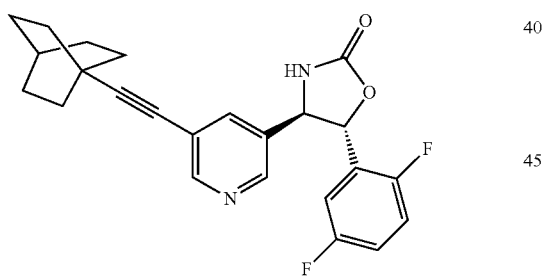

(4R,5R)-4-(5-(Bicyclo[2.2.2]octan-1-ylethynyl)pyridin-3-yl)-5-(2,5-difluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(2,5-difluorophenyl)oxazolidin-2-one (WO2012064603) and 1-ethynylbicyclo[2.2.2]octane. The material was purified by Preparative HPLC Method 7 and concentrated to give the title compound as the TFA salt. $^1$H NMR (CDCl$_3$) δ: 11.80 (br. s., 1H), 8.72 (br. s., 1H), 8.14 (br. s., 1H), 6.88-7.27 (m, 4H), 5.55 (br. s., 1H), 4.95 (br. s., 1H), 1.74-1.96 (m, 6H), 1.66 (d, J=6.3 Hz, 7H). Mass spec.: 409.3 (MH)$^+$.

Example 83

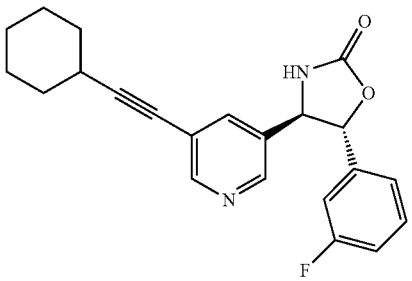 [SMILES: O=C1N[C@H](c2cncc(C#CC3CCCCC3)c2)[C@@H](c2cccc(F)c2)O1]

(4R,5R)-4-(5-(Cyclohexylethynyl)pyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and ethynylcyclohexane. $^1$H NMR (DMSO-$d_6$) δ: 8.58 (d, J=1.5 Hz, 1H), 8.39-8.48 (m, 2H), 7.83 (t, J=2.0 Hz, 1H), 7.46-7.55 (m, 1H), 7.25-7.33 (m, 2H), 7.23 (d, J=7.6 Hz, 1H), 5.51 (d, J=6.7 Hz, 1H), 4.94 (d, J=7.0 Hz, 1H), 2.67-2.74 (m, 1H), 1.85 (br. s., 2H), 1.63-1.75 (m, 2H), 1.51 (d, J=9.5 Hz, 3H), 1.28-1.43 (m, 3H). Mass spec.: 365.0 (MH)$^+$.

Example 84

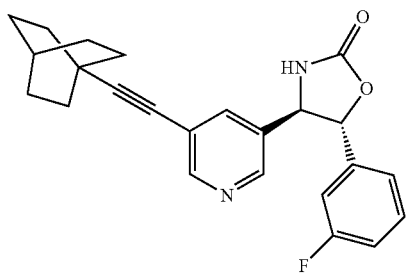 [SMILES: O=C1N[C@H](c2cncc(C#CC34CCC(CC3)CC4)c2)[C@@H](c2cccc(F)c2)O1]

(4R,5R)-4-(5-(Bicyclo[2.2.2]octan-1-ylethynyl)pyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and 1-ethynylbicyclo[2.2.2]octane. Material was purified by Preparative HPLC Method 8 to give the title compound as a TFA salt. $^1$H NMR (CD$_3$OD) δ: 7.96 (br. s., 1H), 7.53-7.72 (m, 1H), 7.44-7.53 (m, 1H), 7.14-7.23 (m, 3H), 5.45 (d, J=6.8 Hz, 1H), 4.97 (d, J=6.5 Hz, 1H), 1.80-1.94 (m, 6H), 1.59-1.73 (m, 7H). Mass spec.: 391.3 (MH)$^+$.

Example 85

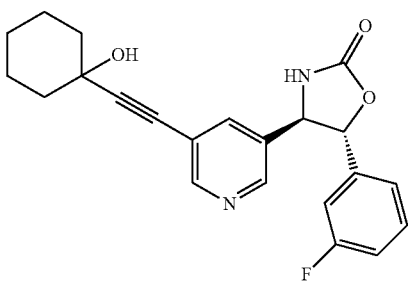 [SMILES: O=C1N[C@H](c2cncc(C#CC3(O)CCCCC3)c2)[C@@H](c2cccc(F)c2)O1]

(4R,5R)-5-(3-Fluorophenyl)-4-(5-((1-hydroxycyclo-hexyl)ethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and 1-ethynylcyclohexanol. $^1$H NMR (DMSO-$d_6$) δ: 8.61 (d, J=2.1 Hz, 1H), 8.47 (m, 2H), 7.86 (t, J=2.0 Hz, 1H), 7.47-7.55 (m, 1H), 7.25-7.33 (m, 2H), 7.23 (d, J=7.6 Hz, 1H), 5.56 (s, 1H), 5.52 (d, J=7.0 Hz, 1H), 4.96 (d, J=6.7 Hz, 1H), 1.87 (m, 2H), 1.62-1.73 (m, 2H), 1.44-1.62 (m, 5H), 1.26 (m, 1H). Mass spec.: 381.0 (MH)$^+$.

Example 86

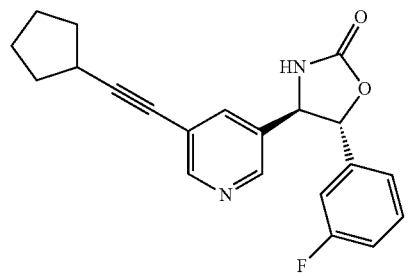 [SMILES: O=C1N[C@H](c2cncc(C#CC3CCCC3)c2)[C@@H](c2cccc(F)c2)O1]

(4R,5R)-4-(5-(Cyclopentylethynyl)pyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and ethynylcyclopentane. $^1$H NMR (DMSO-$d_6$) δ: 8.58 (br. s., 1H), 8.45 (s, 2H), 7.83 (s, 1H), 7.46-7.56 (m, 1H), 7.25-7.33 (m, 2H), 7.22 (d, J=7.9 Hz, 1H), 5.50 (d, J=6.7 Hz, 1H), 4.93 (d, J=7.0 Hz, 1H), 2.88-2.98 (m, 1H), 1.96-2.07 (m, 2H), 1.56-1.80 (m, 6H). Mass spec.: 351.2 (MH)$^+$.

Example 87

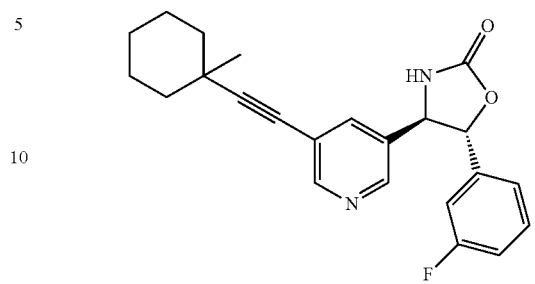

(4R,5R)-5-(3-Fluorophenyl)-4-(5-((1-methylcyclo-hexyl)ethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and 1-ethynyl-1-methylcyclohexane. $^1$H NMR (DMSO-$d_6$) δ: 8.59 (d, J=1.8 Hz, 1H), 8.45 (s, 1H), 8.43 (d, J=2.1 Hz, 1H), 7.85 (s, 1H), 7.48-7.54 (m, 1H), 7.25-7.33 (m, 2H), 7.23 (d, J=7.9 Hz, 1H), 5.52 (d, J=7.0 Hz, 1H), 4.95 (d, J=6.7 Hz, 1H), 1.78 (d, J=12.5 Hz, 2H), 1.57-1.70 (m, 5H), 1.30-1.36 (m, 2H), 1.29 (s, 3H), 1.18 (d, J=7.3 Hz, 1H). Mass spec.: 379.2 (MH)$^+$.

Example 88

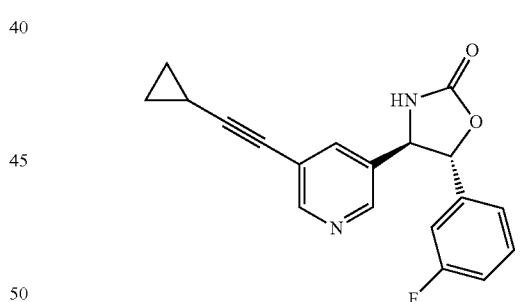

(4R,5R)-4-(5-(Cyclopropylethynyl)pyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and ethynylcyclopropane. $^1$H NMR (DMSO-$d_6$) δ: 8.59 (br. s., 1H), 8.44 (s, 2H), 7.81 (s, 1H), 7.47-7.54 (m, 1H), 7.24-7.32 (m, 2H), 7.22 (d, J=7.6 Hz, 1H), 5.49 (d, J=6.7 Hz, 1H), 4.92 (d, J=7.0 Hz, 1H), 1.56-1.67 (m, 1H), 0.90-0.99 (m, 2H), 0.76-0.83 (m, 2H). Mass spec.: 323.2 (MH)$^+$.

Example 89

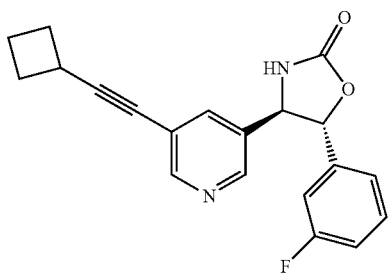 [SMILES: O=C1N[C@H](c2cncc(C#CC3CCC3)c2)[C@@H](c2cccc(F)c2)O1]

(4R,5R)-4-(5-(Cyclobutylethynyl)pyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and ethynylcyclobutane. $^1$H NMR (DMSO-d$_6$) δ: 8.59 (d, J=1.8 Hz, 1H), 8.45 (d, J=1.8 Hz, 2H), 7.85 (s, 1H), 7.46-7.55 (m, 1H), 7.25-7.33 (m, 2H), 7.22 (d, J=7.6 Hz, 1H), 5.51 (d, J=7.0 Hz, 1H), 4.93 (d, J=7.0 Hz, 1H), 3.34 (m, 1H, obscured by DMSO-d$_6$ peak), 2.34 (dtd, J=11.7, 8.6, 3.5 Hz, 2H), 2.17 (dq, J=11.4, 9.0 Hz, 2H), 1.83-2.04 (m, 2H). Mass spec.: 337.2 (MH)$^+$.

Example 90

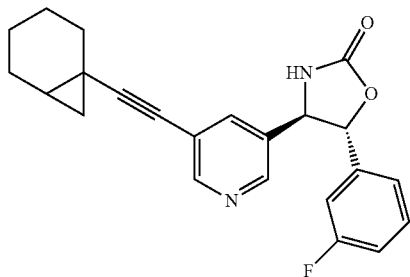 [SMILES: O=C1N[C@H](c2cncc(C#CC34CCCCC3C4)c2)[C@@H](c2cccc(F)c2)O1]

(4R,5R)-4-(5-(Bicyclo[4.1.0]heptan-1-ylethynyl)pyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and (±)-1-ethynylbicyclo[4.1.0]heptane. $^1$H NMR (CDCl$_3$) δ: 8.68 (s, 1H), 8.59 (br. s., 1H), 8.03 (s, 1H), 7.38-7.50 (m, 1H), 7.12-7.21 (m, 1H), 7.07 (t, J=8.4 Hz, 2H), 6.51 (br. s., 1H), 5.29 (d, J=7.0 Hz, 1H), 4.90 (d, J=6.8 Hz, 1H), 1.90-2.18 (m, 3H), 1.62-1.75 (m, 1H), 1.13-1.54 (m, 6H), 0.77 (dd, J=6.5, 4.8 Hz, 1H). Mass spec.: 377.3 (MH)$^+$.

Example 91

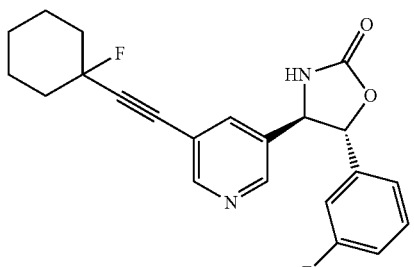

(4R,5R)-4-(5-((1-Fluorocyclohexyl)ethynyl)pyridin-3-yl)-5-(3-fluorophenyl)oxazolidin-2-one A 1 dram vial was charged with (4R,5R)-5-(3-fluorophenyl)-4-(5-((1-hydroxycyclohexyl)ethynyl)pyridin-3-yl)oxazolidin-2-one (26 mg, 0.068 mmol) and dichloromethane (228 µL). The resulting solution was cooled to −78° C. and treated with DAST (55.1 mg, 0.342 mmol). The mixture was allowed to gradually warm to 0° C. and held at 0° C. for 1 h. The reaction was diluted with ether and poured onto water. The organics were further diluted with ethyl acetate and the layers separated. The organics were washed with brine, dried over magnesium sulfate, filtered, and concentrated. The material was purified using Preparative HPLC Method 1 to afford 5.7 mg (22%). $^1$H NMR (DMSO-d$_6$) δ: 8.70 (d, J=1.8 Hz, 1H), 8.53 (d, J=2.1 Hz, 1H), 8.46 (s, 1H), 8.00 (s, 1H), 7.47-7.55 (m, 1H), 7.25-7.34 (m, 2H), 7.23 (d, J=7.6 Hz, 1H), 5.53 (d, J=7.0 Hz, 1H), 4.96 (d, J=7.0 Hz, 1H), 1.88-2.15 (m, 4H), 1.70 (br. s., 2H), 1.33-1.65 (m, 4H). Mass spec.: 383.2 (MH)$^+$.

Example 92

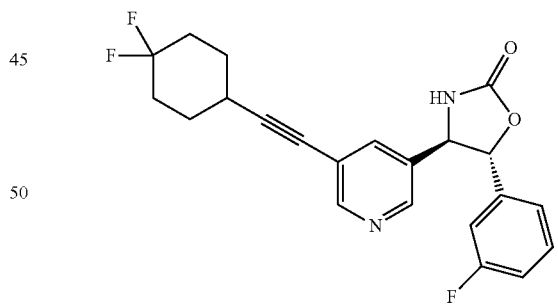

(4R,5R)-4-(5-((4,4-Difluorocyclohexyl)ethynyl)pyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and 4-ethynyl-1,1-difluorocyclohexane. $^1$H NMR (DMSO-d$_6$) δ: 8.62 (br. s., 1H), 8.45 (s, 2H), 7.89 (t, J=1.8 Hz, 1H), 7.46-7.55 (m, 1H), 7.25-7.34 (m, 2H), 7.22 (d, J=7.9 Hz, 1H), 5.51 (d, J=7.0 Hz, 1H), 4.94 (d, J=7.0 Hz, 1H), 1.88-2.17 (m, 7H), 1.68-1.81 (m, 2H). Mass spec.: 401.1 (MH)⁺.

Example 93

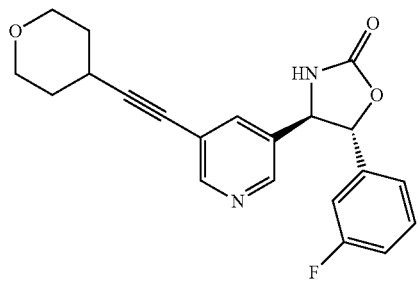 [SMILES: O=C1N[C@H](c2cncc(C#CC3CCOCC3)c2)[C@@H](c2cccc(F)c2)O1]

(4R,5R)-5-(3-Fluorophenyl)-4-(5-((tetrahydro-2H-pyran-4-yl)ethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and 4-ethynyltetrahydro-2H-pyran. ¹H NMR (DMSO-d₆) δ: 8.61 (d, J=2.1 Hz, 1H), 8.46 (d, J=1.5 Hz, 2H), 7.88 (t, J=2.0 Hz, 1H), 7.47-7.55 (m, 1H), 7.25-7.34 (m, 2H), 7.23 (d, J=7.9 Hz, 1H), 5.51 (d, J=7.0 Hz, 1H), 4.94 (d, J=6.7 Hz, 1H), 3.83 (dt, J=11.7, 4.2 Hz, 2H), 3.43-3.51 (m, 2H), 2.97 (dt, J=8.8, 4.6 Hz, 1H), 1.82-1.92 (m, 2H), 1.58-1.70 (m, 2H). Mass spec.: 367.3 (MH)⁺.

Example 94

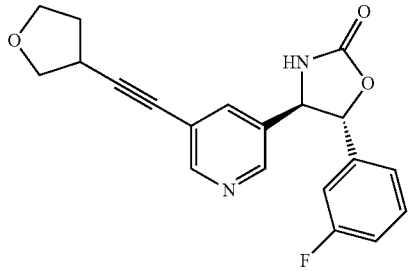 [SMILES: O=C1N[C@H](c2cncc(C#CC3CCOC3)c2)[C@@H](c2cccc(F)c2)O1]

(4R,5R)-5-(3-Fluorophenyl)-4-(5-((tetrahydrofuran-3-yl)ethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and (±)-3-ethynyltetrahydrofuran. (DMSO-d₆) δ: 8.61 (d, J=1.8 Hz, 1H), 8.43-8.48 (m, 2H), 7.87 (t, J=2.0 Hz, 1H), 7.46-7.54 (m, 1H), 7.25-7.33 (m, 2H), 7.22 (d, J=7.9 Hz, 1H), 5.50 (d, J=7.0 Hz, 1H), 4.94 (d, J=7.0 Hz, 1H), 3.99 (t, J=7.8 Hz, 1H), 3.86 (td, J=8.1, 5.8 Hz, 1H), 3.74-3.80 (m, 1H), 3.65 (dd, J=7.9, 6.7 Hz, 1H), 3.29-3.34 (m, 1H), 2.25-2.34 (m, 1H), 1.93-2.05 (m, 1H). Mass spec.: 353.2 (MH)⁺.

Example 95

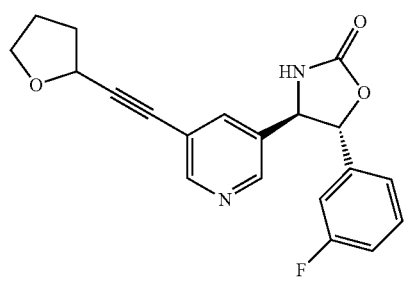 [SMILES: O=C1N[C@H](c2cncc(C#CC3CCCO3)c2)[C@@H](c2cccc(F)c2)O1]

(4R,5R)-5-(3-Fluorophenyl)-4-(5-((tetrahydrofuran-2-yl)ethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and (±)-2-ethynyltetrahydrofuran. LC/MS (Analytical HPLC Method 1; t=2.30 min): Mass spec.: 353.4 (MH)⁺.

Example 96

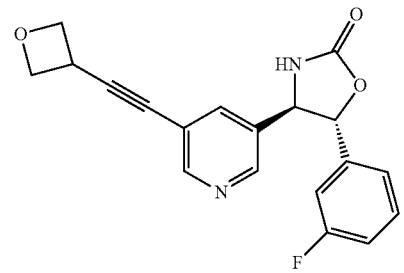 [SMILES: O=C1N[C@H](c2cncc(C#CC3COC3)c2)[C@@H](c2cccc(F)c2)O1]

(4R,5R)-5-(3-Fluorophenyl)-4-(5-(oxetan-3-ylethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and 3-ethynyloxetane. ¹H NMR (CDCl₃) δ: 8.70 (d, J=1.8 Hz, 1H), 8.41 (d, J=2.0 Hz, 1H), 7.80 (t, J=2.0 Hz, 1H), 7.41 (td, J=8.1, 5.6 Hz, 1H), 7.13 (ddt, J=8.9, 7.8, 1.2 Hz, 1H), 7.02-7.09 (m, 2H), 5.97 (s, 1H), 5.28 (d, J=7.0 Hz, 1H), 4.92 (dd, J=8.5, 5.5 Hz, 2H), 4.83 (dd, J=7.2, 5.6 Hz, 2H), 4.77 (d, J=7.3 Hz, 1H), 4.06-4.16 (m, 1H). Mass spec.: 339.3 (MH)⁺.

Example 97

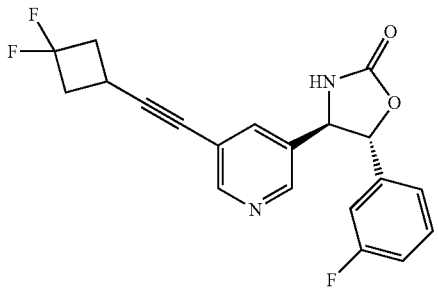 [SMILES: O=C1N[C@H](c2cncc(C#CC3CC(F)(F)C3)c2)[C@@H](c2cccc(F)c2)O1]

(4R,5R)-4-(5-((3,3-Difluorocyclobutyl)ethynyl)pyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and 3-ethynyl-1,1-difluorocyclobutane. $^1$H NMR (CDCl$_3$) δ: 8.68 (d, J=1.9 Hz, 1H), 8.41 (d, J=2.2 Hz, 1H), 7.79 (t, J=2.0 Hz, 1H), 7.38-7.47 (m, 1H), 7.14 (tdd, J=8.4, 2.5, 0.7 Hz, 1H), 7.03-7.10 (m, 2H), 6.19 (s, 1H), 5.29 (d, J=7.3 Hz, 1H), 4.79 (d, J=7.3 Hz, 1H), 3.12-3.23 (m, 1H), 2.96-3.10 (m, 2H), 2.74-2.89 (m, 2H). Mass spec.: 373.3 (MH)$^+$.

Example 98 and Example 99

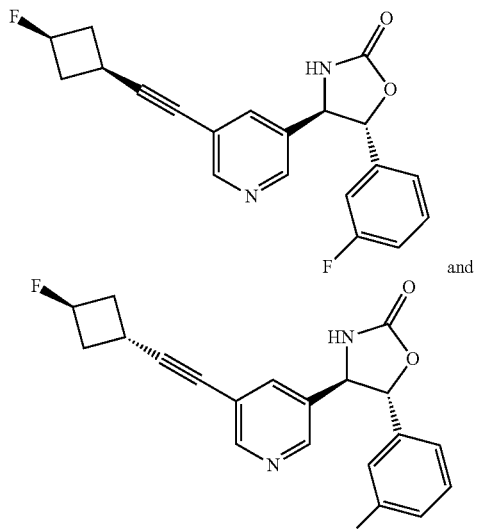

(4R,5R)-4-(5-(((1s,3S)-3-Fluorocyclobutyl)ethynyl) pyridin-3-yl)-5-(3-fluorophenyl)oxazolidin-2-one and (4R,5R)-4-(5-(((1r,3R)-3-Fluorocyclobutyl) ethynyl)pyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and a mixture of cis- and trans-1-ethynyl-3-fluorocyclobutane. The crude material was purified via Preparative HPLC Method 2 to give the product as a mixture of epimers. The material was further purified via Preparative HPLC Method 3 to give the two individual epimers. Example 98 (first eluting): $^1$H NMR (DMSO-d$_6$) δ: 8.60 (s, 1H), 8.45 (s, 2H), 7.87 (s, 1H), 7.45-7.54 (m, 1H), 7.23-7.32 (m, 2H), 7.21 (d, J=7.6 Hz, 1H), 5.49 (d, J=6.7 Hz, 1H), 4.84-5.13 (m, 2H), 2.75-2.92 (m, 3H), 2.22-2.39 (m, 2H). Mass spec.: 355.2 (MH)$^+$. Example 99 (second eluting): $^1$H NMR (DMSO-d$_6$) δ: 8.60 (s, 1H), 8.45 (s, 2H), 7.86 (s, 1H), 7.45-7.54 (m, 1H), 7.23-7.32 (m, 2H), 7.21 (d, J=7.3 Hz, 1H), 5.49 (d, J=7.0 Hz, 1H), 5.22-5.43 (m, 1H), 4.93 (d, J=6.7 Hz, 1H), 2.46-2.66 (m, 5H, obscured by DMSO-d$_6$). Mass spec.: 355.1 (MH)$^+$.

Example 100

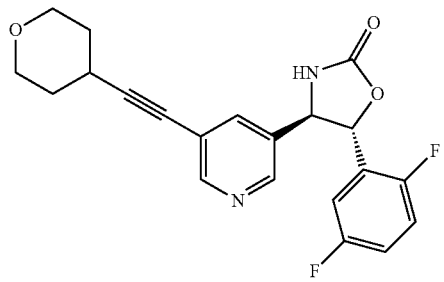 [SMILES: O=C1N[C@H](c2cncc(C#CC3CCOCC3)c2)[C@@H](c2cc(F)ccc2F)O1]

(4R,5R)-5-(2,5-Difluorophenyl)-4-(5-((tetrahydro-2H-pyran-4-yl)ethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(2,5-difluorophenyl)oxazolidin-2-one (WO2012064603) and 4-ethynyltetrahydro-2H-pyran. $^1$H NMR (DMSO-d$_6$) δ: 8.62 (br. s., 1H), 8.42-8.56 (m, 2H), 7.90 (s, 1H), 7.30-7.44 (m, 3H), 5.63 (d, J=6.7 Hz, 1H), 4.99 (d, J=6.7 Hz, 1H), 3.82 (dt, J=11.6, 4.3 Hz, 2H), 3.43-3.49 (m, 2H), 2.96 (dt, J=8.8, 4.6 Hz, 1H), 1.81-1.93 (m, 2H), 1.63 (d, J=9.5 Hz, 2H). Mass spec.: 385.3 (MH)$^+$.

Example 101

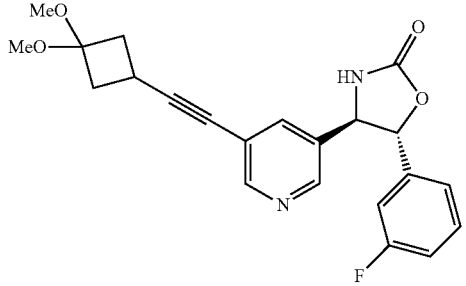 [SMILES: COC1(OC)CC(C#Cc2cncc([C@H]3NC(=O)O[C@@H]3c3cccc(F)c3)c2)C1]

(4R,5R)-4-(5-((3,3-Dimethoxycyclobutyl)ethynyl)pyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-fluorophenyl)oxazolidin-2-one (WO2012064603) and 3-ethynyl-1,1-dimethoxycyclobutane. $^1$H NMR (CDCl$_3$) δ: 8.67 (d, J=1.8 Hz, 1H), 8.37 (d, J=2.3 Hz, 1H), 7.78 (t, J=2.0 Hz, 1H), 7.41 (td, J=7.9, 5.8 Hz, 1H), 6.99-7.17 (m, 3H), 5.53 (s, 1H), 5.29 (d, J=7.3 Hz, 1H), 4.75 (d, J=7.3 Hz, 1H), 3.20 (s, 6H), 3.06 (quin, J=8.5 Hz, 1H), 2.59-2.71 (m, 2H), 2.26-2.42 (m, 2H). Mass spec.: 397.4 (MH)$^+$.

Example 102

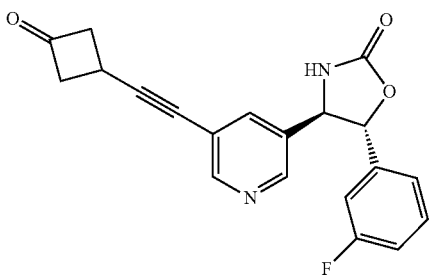 [SMILES: O=C1CC(C#Cc2cncc([C@H]3NC(=O)O[C@@H]3c3cccc(F)c3)c2)C1]

(4R,5R)-5-(3-Fluorophenyl)-4-(5-((3-oxocyclobutyl)ethynyl)pyridin-3-yl)oxazolidin-2-one A flask was charged with (4R,5R)-4-(5-((3,3-dimethoxycyclobutyl)ethynyl)pyridin-3-yl)-5-(3-fluorophenyl)oxazolidin-2-one (175 mg, 0.441 mmol). To this was added trifluoroacetic acid (1 mL). After 30 min, the reaction was concentrated, suspended in ether, washed with saturated sodium bicarbonate, dried over magnesium sulfate, filtered, and concentrated. Column chromatography (50% EtOAc/Hex) gave 140 mg (86%) as a white solid. $^1$H NMR (CDCl$_3$) δ: 8.68 (d, J=1.7 Hz, 1H), 8.41 (d, J=2.2 Hz, 1H), 7.79 (s, 1H), 7.37-7.45 (m, 1H), 7.13 (ddd, J=9.1, 7.6, 2.0 Hz, 1H), 7.02-7.09 (m, 2H), 6.60 (s, 1H), 5.27 (d, J=7.3 Hz, 1H), 4.79 (d, J=7.3 Hz, 1H), 3.50-3.60 (m, 2H), 3.42-3.50 (m, 1H), 3.33-3.42 (m, 2H). Mass spec.: 351.3 (MH)$^+$.

Example 103

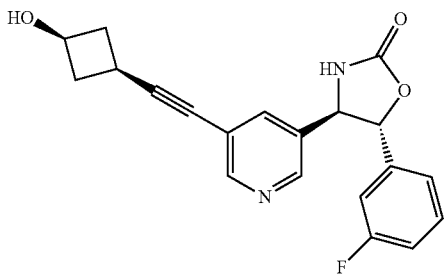 [SMILES: O=C1N[C@H](c2cncc(C#C[C@H]3C[C@@H](O)C3)c2)[C@@H](c2cccc(F)c2)O1]

(4R,5R)-5-(3-Fluorophenyl)-4-(5-(((1s, 3S)-3-hydroxycyclobutyl)ethynyl)pyridin-3-yl)oxazolidin-2-one To a solution of (4R,5R)-5-(3-fluorophenyl)-4-(5-((3-oxocyclobutyl)ethynyl)pyridin-3-yl)oxazolidin-2-one (15 mg, 0.043 mmol) in ethanol (1 mL) was added sodium borohydride (2.4 mg, 0.064 mmol). After 10 min, the reaction was quenched by addition of saturated ammonium chloride (~0.3 mL) and concentrated under a stream of nitrogen. The resulting residue was suspended in dichloromethane/water and diluted with ethyl acetate. After separation of the layers, the organics were washed with brine, dried over magnesium sulfate, filtered, and concentrated. Flash chromatography (50% EtOAc/Hex 100% EtOAc) gave 11.1 mg (70%). $^1$H NMR (CDCl$_3$) δ: 8.65 (d, J=1.9 Hz, 1H), 8.37 (d, J=2.2 Hz, 1H), 7.78 (t, J=2.0 Hz, 1H), 7.41 (td, J=7.9, 5.8 Hz, 1H), 7.10-7.16 (m, 1H), 7.02-7.10 (m, 2H), 6.31 (s, 1H), 5.28 (d, J=7.3 Hz, 1H), 4.77 (d, J=7.3 Hz, 1H), 4.19-4.30 (m, 1H), 2.68-2.85 (m, 3H), 2.41 (d, J=6.3 Hz, 1H), 2.13-2.25 (m, 2H). Mass spec.: 353.3 (MH)$^+$.

Example 104

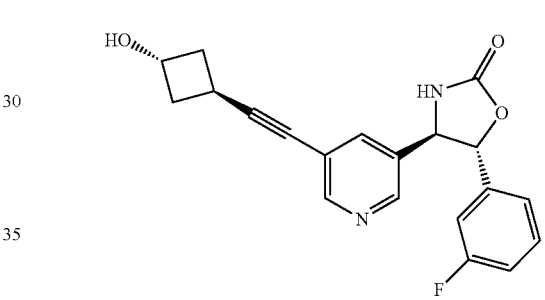

(4R,5R)-5-(3-Fluorophenyl)-4-(5-(((1r,3R)-3-hydroxycyclobutyl)ethynyl)pyridin-3-yl)oxazolidin-2-one A vial was charged with (4R,5R)-5-(3-fluorophenyl)-4-(5-(((1s,3S)-3-hydroxycyclobutyl)ethynyl)pyridin-3-yl)oxazolidin-2-one (9 mg, 0.026 mmol), 4-nitrobenzoic acid (8.54 mg, 0.051 mmol), triphenylphosphine (14.07 mg, 0.054 mmol), and tetrahydrofuran (0.4 mL) and cooled to 0° C. To this was added diethylazodicarboxylate (40% in toluene) (0.024 mL, 0.054 mmol). After 30 min, the ice bath was removed and stirring continued overnight. The reaction was concentrated, purified by prep HPLC (Preparative HPLC Method 5). The fractions containing product were concentrated. This material was dissolved in tetrahydrofuran (0.4 mL) and methanol (0.4 mL). To this was added lithium hydroxide monohydrate (1.223 mg, 0.051 mmol) in water (0.4 mL). After stirring at room temperature for 1 h, the reaction was quenched by addition of 1 drop of trifluoroacetic acid, and concentrated to remove most solvent. The resulting residue was suspended in ethyl acetate, washed with saturated sodium bicarbonate (2×), then brine, dried over magnesium sulfate, filtered, and concentrated. The resulting residue was purified by Preparative HPLC Method 6. $^1$H NMR (DMSO-d$_6$) δ: 8.57 (br. s., 1H), 8.45 (br. s., 1H), 8.42 (br. s., 1H), 7.83 (m, 1H), 7.49 (m, 1H), 7.17-7.33 (m, 3H), 5.48 (d, J=6.1 Hz, 1H), 5.36 (br. s., 1H), 4.91 (d, J=6.7

Hz, 1H), 4.40 (m, 1H), 3.19 (m, 1H), 2.33 (m, 1H), 2.22 (m, 1H), 1.90 (s, 2H). Mass spec.: 353.3 (MH)+.

Example 105 and Example 106

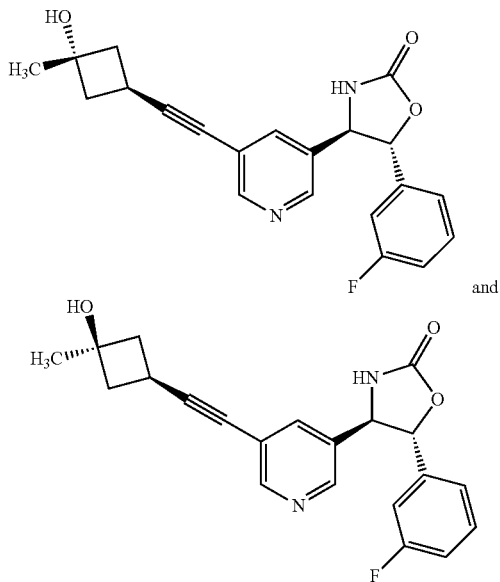

(4R,5R)-5-(3-Fluorophenyl)-4-(5-(((1r,3R)-3-hydroxy-3-methylcyclobutyl)ethynyl)pyridin-3-yl)oxazolidin-2-one and (4R,5R)-5-(3-fluorophenyl)-4-(5-(((1s,3S)-3-hydroxy-3-methylcyclobutyl)ethynyl)pyridin-3-yl)oxazolidin-2-one (4R,5R)-5-(3-Fluorophenyl)-4-(5-((3-oxocyclobutyl)ethynyl)pyridin-3-yl)oxazolidin-2-one (20 mg, 0.057 mmol) was dissolved in tetrahydrofuran (0.5 mL). The reaction was placed in a 0° C. bath and treated with methylmagnesium bromide (3M in ether, 0.076 mL, 0.228 mmol) drop wise. After addition was complete, the reaction was stirred at 0° C. for 10 min, and quenched by the cautious addition of saturated ammonium chloride. The mixture was extracted with ethyl acetate. The organics were washed with brine, dried over magnesium sulfate, filtered, and concentrated. Column chromatography (50%-75% EtOAc/Hex) gave the product as a mixture of epimers. The material was re-purified by Preparative HPLC Method 4 to give the two individual stereoisomers. The first to elute was (4R,5R)-5-(3-Fluorophenyl)-4-(5-(((1r,3R)-3-hydroxy-3-methylcyclobutyl)ethynyl)pyridin-3-yl)oxazolidin-2-one (Example 105, minor epimer): $^1$H NMR (CDCl$_3$) δ: 8.71 (s, 1H), 8.44 (br. s., 1H), 7.91 (s, 1H), 7.44 (td, J=7.9, 5.8 Hz, 1H), 7.12-7.19 (m, 1H), 7.04-7.12 (m, 2H), 5.76 (s, 1H), 5.31 (d, J=7.3 Hz, 1H), 4.82 (d, J=7.3 Hz, 1H), 3.35 (tt, J=9.5, 5.9 Hz, 1H), 2.53-2.61 (m, 2H), 2.48 (bs, 2H), 2.28-2.35 (m, 2H), 1.58 (s, 3H). 19F NMR (CDCl$_3$) d: −75.91 (s, 3F), −110.58--110.39 (m, 1F). Mass spec.: 367.2 (MH)+. The second to elute was (4R,5R)-5-(3-fluorophenyl)-4-(5-(((1s,3S)-3-hydroxy-3-methylcyclobutyl)ethynyl)pyridin-3-yl)oxazolidin-2-one (Example 106, major epimer): $^1$H NMR (CDCl$_3$) δ: 8.70 (br. s., 1H), 8.53 (br. s., 1H), 7.98 (s, 1H), 7.44 (td, J=7.9, 5.8 Hz, 1H), 7.16 (td, J=8.4, 1.9 Hz, 1H), 7.03-7.12 (m, 2H), 6.51 (br. s., 1H), 5.30 (d, J=7.1 Hz, 1H), 4.87 (d, J=7.1 Hz, 1H), 4.18 (br. s., 2H), 2.84 (quin, J=8.7 Hz, 1H), 2.49-2.61 (m, 2H), 2.30-2.44 (m, 2H), 1.43 (s, 3H). 19F NMR (CDCl$_3$) d: −76.27--75.51 (m, 3F), −110.43 (d, J=4.4 Hz, 1F). Mass spec.: 367.2 (MH)+.

Example 107

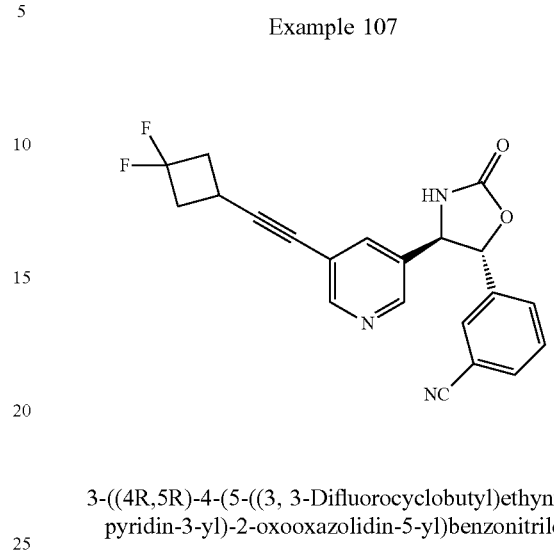

3-((4R,5R)-4-(5-((3, 3-Difluorocyclobutyl)ethynyl)pyridin-3-yl)-2-oxooxazolidin-5-yl)benzonitrile Prepared according to the same procedure as (4R,5R)-4-(5-(3-(dimethylamino)prop-1-yn-1-yl)pyridin-3-yl)-5-(3-fluorophenyl)oxazolidin-2-one, starting with 3-((4R,5R)-4-(5-bromopyridin-3-yl)-2-oxooxazolidin-5-yl)benzonitrile and 3-ethynyl-1,1-difluorocyclobutane. $^1$H NMR (DMSO-d$_6$) δ: 8.62 (br. s., 1H), 8.48 (d, J=16.8 Hz, 2H), 7.90 (d, J=13.7 Hz, 3H), 7.62-7.76 (m, 2H), 5.54 (d, J=5.8 Hz, 1H), 4.96 (d, J=6.1 Hz, 1H), 3.07 (d, J=10.4 Hz, 3H), 2.74 (d, J=8.2 Hz, 2H). Mass spec.: 380.2 (MH)+.

Example 108

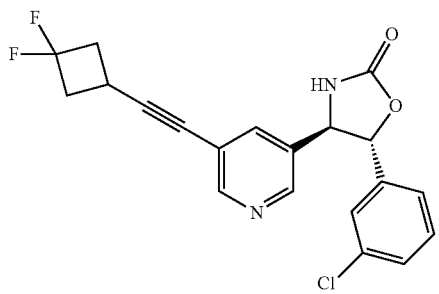 [SMILES: O=C1N[C@H](c2cncc(C#CC3CC(F)(F)C3)c2)[C@@H](c2cccc(Cl)c2)O1]

(4R,5R)-5-(3-Chlorophenyl)-4-(5-((3,3-difluorocyclobutyl)ethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-chlorophenyl)oxazolidin-2-one (WO2012064603) and 3-ethynyl-1,1-difluorocyclobutane. $^1$H NMR (DMSO-d$_6$) δ: 8.62 (br. s., 1H), 8.47 (br. s., 2H), 7.87 (br. s., 1H), 7.49 (br. s., 3H), 7.34 (br. s., 1H), 5.48 (d, J=6.7 Hz, 1H), 4.94 (d, J=6.4 Hz, 1H), 2.99-3.13 (m, 3H), 2.76 (dd, J=13.6, 6.9 Hz, 2H). Mass spec.: 389.2 (MH)+.

Example 109

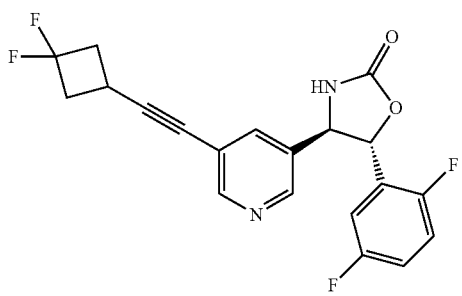 [SMILES: O=C1N[C@H](c2cncc(C#CC3CC(F)(F)C3)c2)[C@@H](c2cc(F)ccc2F)O1]

(4R,5R)-4-(5-((3,3-Difluorocyclobutyl)ethynyl)pyridin-3-yl)-5-(2,5-difluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(2,5-difluorophenyl)oxazolidin-2-one (WO2012064603) and 3-ethynyl-1,1-difluorocyclobutane. $^1$H NMR (DMSO-d$_6$) δ: 8.63 (br. s., 1H), 8.52 (br. s., 2H), 7.92 (br. s., 1H), 7.36 (m, 3H), 5.62 (d, J=6.4 Hz, 1H), 4.99 (d, J=6.4 Hz, 1H), 3.06 (m, 3H), 2.76 (m, 2H). Mass spec.: 391.3 (MH)$^+$.

Example 110

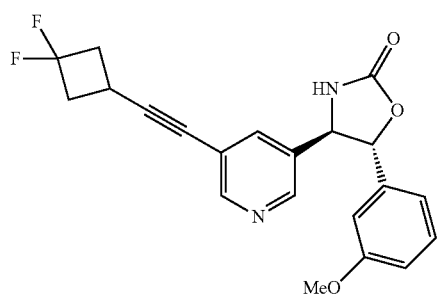

(4R,5R)-4-(5-((3,3-Difluorocyclobutyl)ethynyl)pyridin-3-yl)-5-(3-methoxyphenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3-methoxyphenyl)oxazolidin-2-one (WO2012064603) and 3-ethynyl-1,1-difluorocyclobutane. $^1$H NMR (DMSO-d$_6$) δ: 8.62 (br. s., 1H), 8.46 (br. s., 1H), 8.39 (br. s., 1H), 7.87 (br. s., 1H), 7.35 (m, 1H), 6.87-7.03 (m, 3H), 5.41 (d, J=7.0 Hz, 1H), 4.92 (d, J=6.4 Hz, 1H), 3.77 (br. s., 3H), 3.06 (m, 3H), 2.77 (m, 2H). Mass spec.: 385.3 (MH)$^+$.

Example 111

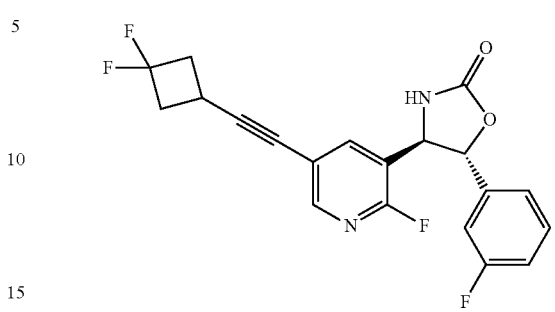

(4R,5R)-4-(5-((3,3-Difluorocyclobutyl)ethynyl)-2-fluoropyridin-3-yl)-5-(3-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromo-2-fluoropyridin-3-yl)-5-(3-fluorophenyl)oxazolidin-2-one (WO2012064603) and 3-ethynyl-1,1-difluorocyclobutane. $^1$H NMR (DMSO-d$_6$) δ: 8.44 (br. s., 1H), 8.33 (br. s., 1H), 8.09 (d, J=8.2 Hz, 1H), 7.51 (d, J=6.4 Hz, 1H), 7.19-7.34 (m, 3H), 5.57 (d, J=5.2 Hz, 1H), 4.99 (d, J=5.2 Hz, 1H), 3.08 (d, J=9.5 Hz, 3H), 2.78 (br. s., 2H). Mass spec.: 391.3 (MH)$^+$.

Example 112

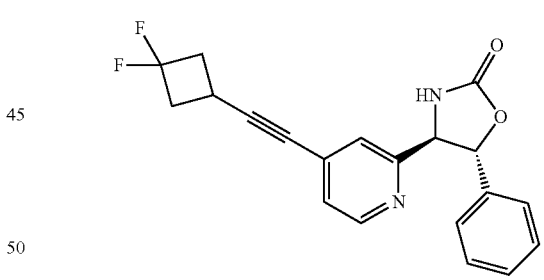

(4R,5R)-4-(4-((3,3-Difluorocyclobutyl)ethynyl)pyridin-2-yl)-5-phenyloxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(4-bromopyridin-2-yl)-5-phenyloxazolidin-2-one (WO2012064603) and 3-ethynyl-1,1-difluorocyclobutane. $^1$H NMR (DMSO-d$_6$) δ: 8.61 (br. s., 1H), 8.42 (br. s., 1H), 7.31-7.56 (m, 7H), 5.54 (br. s., 1H), 4.85 (br. s., 1H), 3.07 (br. s., 3H), 2.76 (br. s., 2H). Mass spec.: 355.3 (MH)$^+$.

Example 113

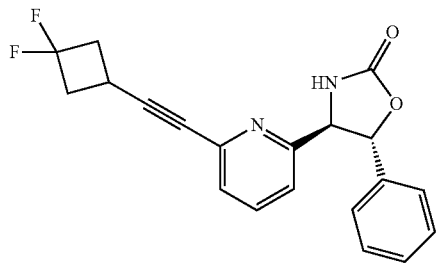 [SMILES: O=C1N[C@H](c2cccc(C#CC3CC(F)(F)C3)n2)[C@@H](c2ccccc2)O1]

(4R,5R)-4-(6-((3,3-Difluorocyclobutyl)ethynyl)pyridin-2-yl)-5-phenyloxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(6-bromopyridin-2-yl)-5-phenyloxazolidin-2-one (WO2012064603) and 3-ethynyl-1,1-difluorocyclobutane. $^1$H NMR (DMSO-d$_6$) δ: 8.46 (br. s., 1H), 7.84-7.92 (m, 1H), 7.51 (d, J=7.6 Hz, 1H), 7.37-7.48 (m, 6H), 5.51 (d, J=4.9 Hz, 1H), 4.84 (d, J=5.5 Hz, 1H), 2.97-3.14 (m, 3H), 2.78 (dd, J=14.3, 7.0 Hz, 2H). Mass spec.: 355.3 (MH)$^+$.

Example 114

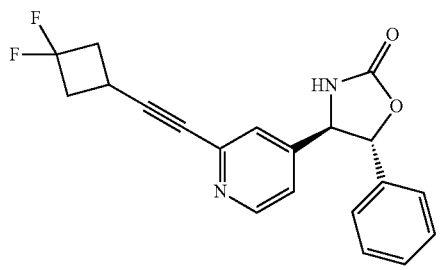 [SMILES: O=C1N[C@H](c2ccnc(C#CC3CC(F)(F)C3)c2)[C@@H](c2ccccc2)O1]

(4R,5R)-4-(2-((3,3-Difluorocyclobutyl)ethynyl)pyridin-4-yl)-5-phenyloxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(2-bromopyridin-4-yl)-5-phenyloxazolidin-2-one (WO2012064603) and 3-ethynyl-1,1-difluorocyclobutane. $^1$H NMR (CDCl$_3$) δ: 8.60 (d, J=5.0 Hz, 1H), 7.42-7.49 (m, 3H), 7.39 (d, J=0.8 Hz, 1H), 7.30-7.35 (m, 2H), 7.14 (dd, J=5.1, 1.6 Hz, 1H), 6.01 (s, 1H), 5.23 (d, J=7.0 Hz, 1H), 4.77 (d, J=7.3 Hz, 1H), 3.10-3.22 (m, 1H), 2.93-3.07 (m, 2H), 2.76-2.92 (m, 2H). Mass spec.: 355.3 (MH)$^+$.

Example 115

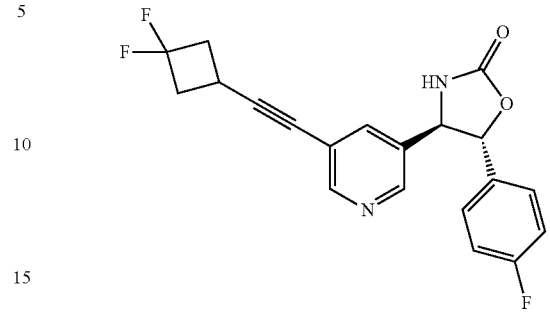

(4R,5R)-4-(5-((3,3-Difluorocyclobutyl)ethynyl)pyridin-3-yl)-5-(4-fluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(4-fluorophenyl)oxazolidin-2-one (WO2012064603) and 3-ethynyl-1,1-difluorocyclobutane. $^1$H NMR (CDCl$_3$) δ: 8.65 (d, J=1.5 Hz, 1H), 8.36 (d, J=1.8 Hz, 1H), 7.76 (t, J=2.0 Hz, 1H), 7.24-7.35 (m, 2H), 7.08-7.19 (m, 2H), 6.37-6.48 (m, 1H), 5.24 (d, J=7.5 Hz, 1H), 4.78 (d, J=7.5 Hz, 1H), 3.10-3.24 (m, 1H), 2.94-3.09 (m, 2H), 2.71-2.88 (m, 2H). Mass spec.: 373.3 (MH)$^+$.

Example 116

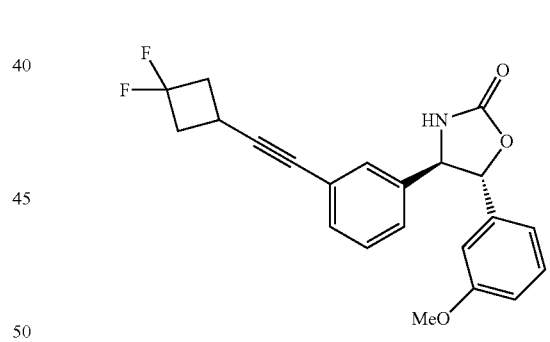

(4R,5R)-4-(3-((3,3-Difluorocyclobutyl)ethynyl)phenyl)-5-(3-methoxyphenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(3-bromophenyl)-5-(3-methoxyphenyl)oxazolidin-2-one (WO2012064603) and 3-ethynyl-1,1-difluorocyclobutane. $^1$H NMR (DMSO-d$_6$) δ: 8.37 (br. s., 1H), 7.25-7.46 (m, 5H), 6.86-7.03 (m, 3H), 5.27 (d, J=7.3 Hz, 1H), 4.83 (d, J=6.4 Hz, 1H), 3.77 (s, 3H), 2.96-3.19 (m, 3H), 2.64-2.81 (m, 2H). Mass spec.: 384.3 (MH)$^+$.

Example 117

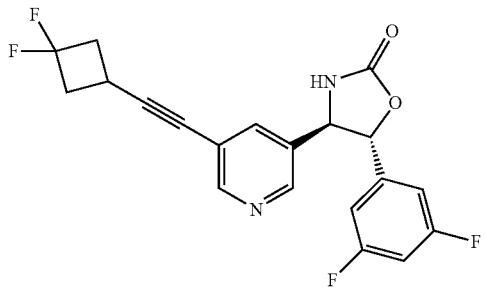 [SMILES: O=C1N[C@H](c2cncc(C#CC3CC(F)(F)C3)c2)[C@@H](c2cc(F)cc(F)c2)O1]

(4R,5R)-4-(5-((3,3-Difluorocyclobutyl)ethynyl)pyridin-3-yl)-5-(3,5-difluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3,5-difluorophenyl)oxazolidin-2-one (WO2012064603) and 3-ethynyl-1,1-difluorocyclobutane. $^1$H NMR (DMSO-$d_6$) δ: 8.63 (br. s., 1H), 8.49 (br. s., 2H), 7.90 (br. s., 1H), 7.32 (br. s., 1H), 7.17 (d, J=5.8 Hz, 2H), 5.50 (d, J=6.1 Hz, 1H), 4.94 (d, J=6.1 Hz, 1H), 3.00-3.21 (m, 3H), 2.76 (dd, J=13.7, 6.1 Hz, 2H). Mass spec.: 391.3 (MH)$^+$.

Example 118

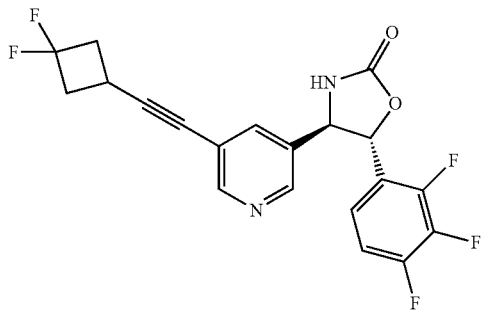 [SMILES: O=C1N[C@H](c2cncc(C#CC3CC(F)(F)C3)c2)[C@@H](c2ccc(F)c(F)c2F)O1]

(4R,5R)-4-(5-((3,3-Difluorocyclobutyl)ethynyl)pyridin-3-yl)-5-(2,3,4-trifluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(2,3,4-trifluorophenyl)oxazolidin-2-one (WO2012064603) and 3-ethynyl-1,1-difluorocyclobutane. $^1$H NMR (DMSO-$d_6$) δ: 8.63 (br. s., 1H), 8.54 (d, J=17.4 Hz, 2H), 7.91 (br. s., 1H), 7.32-7.48 (m, 2H), 5.64 (d, J=6.4 Hz, 1H), 5.04 (d, J=6.4 Hz, 1H), 3.14-3.25 (m, 1H, obscured by DMSO-$d_6$), 3.07 (t, J=9.2 Hz, 2H), 2.70-2.84 (m, 2H). Mass spec.: 409.2 (MH)$^+$.

Example 119

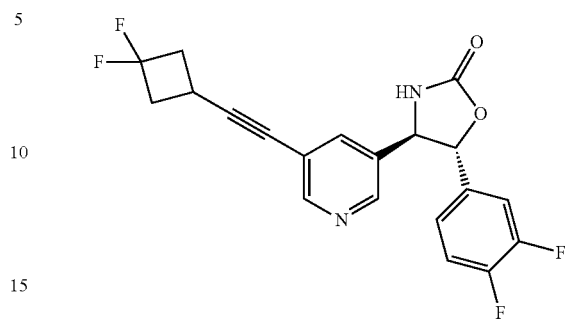

(4R,5R)-4-(5-((3,3-Difluorocyclobutyl)ethynyl)pyridin-3-yl)-5-(3,4-difluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(3,4-difluorophenyl)oxazolidin-2-one (WO2012064603) and 3-ethynyl-1,1-difluorocyclobutane. $^1$H NMR (CDCl$_3$) δ: 8.67 (br. s., 1H), 8.39 (br. s., 1H), 7.76 (s, 1H), 7.15-7.27 (m, 2H), 6.95-7.07 (m, 1H), 6.31 (s, 1H), 5.23 (d, J=7.3 Hz, 1H), 4.75 (d, J=7.3 Hz, 1H), 3.11-3.25 (m, 1H), 2.93-3.09 (m, 2H), 2.70-2.89 (m, 2H). Mass spec.: 391.2 (MH)$^+$.

Example 120

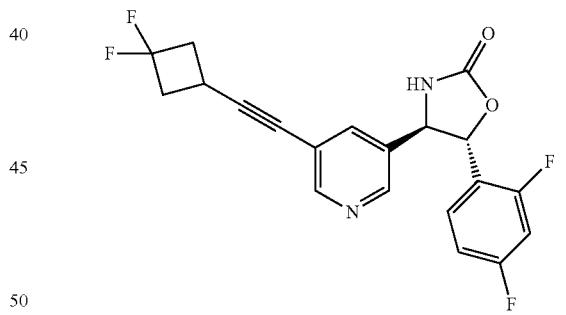

(4R,5R)-4-(5-((3,3-Difluorocyclobutyl)ethynyl)pyridin-3-yl)-5-(2,4-difluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(2,4-difluorophenyl)oxazolidin-2-one (WO2012064603) and 3-ethynyl-1,1-difluorocyclobutane. $^1$H NMR (DMSO-$d_6$) δ: 8.62 (s, 1H), 8.49 (s, 2H), 7.90 (br. s., 1H), 7.58 (q, J=7.9 Hz, 1H), 7.33-7.41 (m, 1H), 7.19 (t, J=8.1 Hz, 1H), 5.59 (d, J=6.4 Hz, 1H), 4.98 (d, J=6.7 Hz, 1H), 3.28-3.32 (m, 1H, obscured by DMSO-$d_6$), 3.00-3.13 (m, 2H), 2.71-2.84 (m, 2H). Mass spec.: 391.5 (MH)$^+$.

Example 121

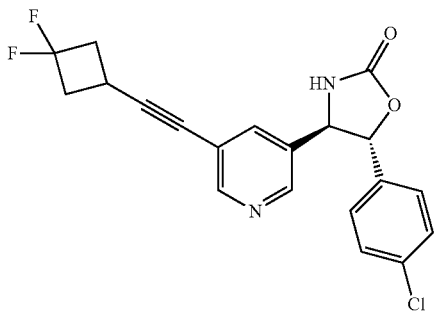 [SMILES: O=C1N[C@H](c2cncc(C#CC3CC(F)(F)C3)c2)[C@@H](c2ccc(Cl)cc2)O1]

(4R,5R)-5-(4-Chlorophenyl)-4-(5-((3,3-difluorocyclobutyl)ethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(4-chlorophenyl)oxazolidin-2-one (WO2012064603) and 3-ethynyl-1,1-difluorocyclobutane. $^1$H NMR (DMSO-d$_6$) δ: 8.62 (br. s., 1H), 8.45 (d, J=14.6 Hz, 2H), 7.88 (br. s., 1H), 7.48-7.55 (m, 2H), 7.43 (d, J=8.2 Hz, 2H), 5.48 (d, J=7.0 Hz, 1H), 4.90 (d, J=6.7 Hz, 1H), 3.00-3.13 (m, 3H), 2.76 (dd, J=13.0, 5.0 Hz, 2H). Mass spec.: 389.5 (MH)$^+$.

Example 122

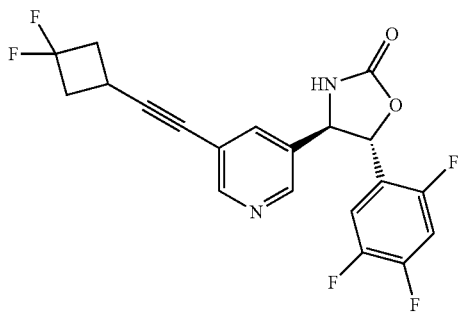 [SMILES: O=C1N[C@H](c2cncc(C#CC3CC(F)(F)C3)c2)[C@@H](c2cc(F)c(F)cc2F)O1]

(4R,5R)-4-(5-((3,3-Difluorocyclobutyl)ethynyl)pyridin-3-yl)-5-(2,4,5-trifluorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(2,4,5-trifluorophenyl)oxazolidin-2-one and 3-ethynyl-1,1-difluorocyclobutane. $^1$H NMR (DMSO-d$_6$) δ: 8.62 (s, 1H), 8.50 (br. s., 2H), 7.92 (br. s., 1H), 7.70 (dd, J=16.2, 6.1 Hz, 2H), 5.58 (d, J=7.0 Hz, 1H), 5.00 (d, J=6.7 Hz, 1H), 3.27-3.30 (m, 1H, obscured by DMSO-d$_6$), 3.00-3.14 (m, 2H), 2.72-2.84 (m, 2H). Mass spec.: 409.5 (MH)$^+$.

Example 123

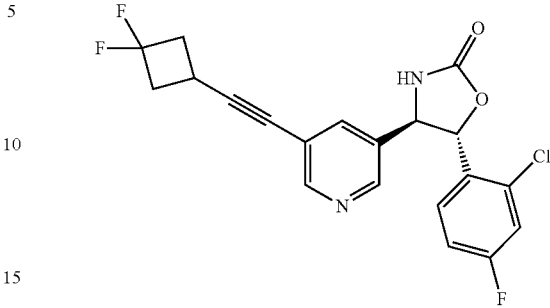

(4R,5R)-5-(2-Chloro-4-fluorophenyl)-4-(5-((3,3-difluorocyclobutyl)ethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(2-chloro-4-fluorophenyl)oxazolidin-2-one and 3-ethynyl-1,1-difluorocyclobutane. $^1$H NMR (DMSO-d$_6$) δ: 8.62 (s, 1H), 8.54 (br. s., 2H), 7.92 (br. s., 1H), 7.59-7.64 (m, 1H), 7.56 (d, J=8.5 Hz, 1H), 7.38 (t, J=7.8 Hz, 1H), 5.71 (d, J=5.8 Hz, 1H), 4.90 (d, J=5.8 Hz, 1H), 3.29-3.31 (m, 1H, obscured by DMSO-d$_6$), 3.00-3.13 (m, 2H), 2.70-2.86 (m, 2H). Mass spec.: 407.5 (MH)$^+$.

Example 124

(4R,5R)-5-(2,3-Dichlorophenyl)-4-(5-((3,3-difluorocyclobutyl)ethynyl)pyridin-3-yl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(2,3-dichlorophenyl)oxazolidin-2-one (WO2012064603) and 3-ethynyl-1,1-difluorocyclobutane. $^1$H NMR (CDCl$_3$) δ: 8.70 (br. s., 1H), 8.56 (br. s., 1H), 7.86 (t, J=2.0 Hz, 1H), 7.56 (dd, J=8.0, 1.5 Hz, 1H), 7.50 (dq, J=7.9, 0.7 Hz, 1H), 7.35-7.41 (m, 1H), 5.75 (d, J=4.0 Hz, 1H), 5.56 (s, 1H), 4.69 (d, J=3.8 Hz, 1H), 3.13-3.25 (m, 1H), 2.96-3.11 (m, 2H), 2.76-2.92 (m, 2H). Mass spec.: 423.2 (MH)$^+$.

Example 125

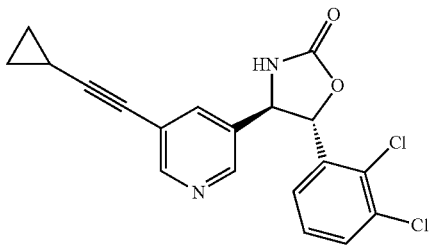 [SMILES: O=C1N[C@H](c2cncc(C#CC3CC3)c2)[C@@H](c2cccc(Cl)c2Cl)O1]

(4R,5R)-4-(5-(Cyclopropylethynyl)pyridin-3-yl)-5-(2,3-dichlorophenyl)oxazolidin-2-one Prepared according to the same procedure as (4R,5R)-4-(5-(3-(dimethylamino)prop-1-yn-1-yl)pyridin-3-yl)-5-(3-fluorophenyl)oxazolidin-2-one, starting with (4R,5R)-4-(5-bromopyridin-3-yl)-5-(2,3-dichlorophenyl)oxazolidin-2-one (WO2012064603) and ethynylcyclopropane. $^1$H NMR (DMSO-$d_6$) δ: 8.50-8.60 (m, 3H), 7.84 (s, 1H), 7.70-7.77 (m, 1H), 7.47-7.56 (m, 2H), 5.79 (d, J=4.9 Hz, 1H), 4.87 (d, J=4.9 Hz, 1H), 1.53-1.70 (m, 1H), 0.94 (dd, J=8.1, 2.6 Hz, 2H), 0.80 (dd, J=4.7, 2.3 Hz, 2H). Mass spec.: 373.2 (MH)$^+$.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

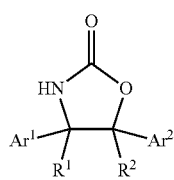

(I)

where:
$R^1$ is hydrogen or alkyl;
$R^2$ is hydrogen or alkyl;
$R^3$ is

;

$R^4$ is cyano, alkyl, haloalkyl, cycloalkyl, hydroxy, alkoxy, haloalkoxy, or thioalkyl, where alkyl, haloalkyl, and cycloalkyl are substituted with 0-3 substituents selected from halo, alkyl, haloalkyl, hydroxy, and alkoxy;
or $R^4$ is a bridged [1-4.1-4.0-3]bicycloalkyl;
or $R^4$ is alkylcarbonylamino, haloalkylcarbonylamino, cycloalkanonyl, valerolactamyl, oxetanyl, tetrahydrofuranyl, tetrahydropyranyl, or tetrahydropyranyloxy;
or $R^4$ is amino, alkylamino, dialkylamino, azetidinyl, pyrrolidinyl, piperidinyl, piperazinyl, morpholinyl, homopiperidinyl, homopiperazinyl, or homomorpholinyl;
L is a bond, alkylene, or hydroxyalkylene;
$Ar^1$ is phenyl, pyridinyl, pyrazinyl, pyrimidinyl, or pyridazinyl, and is substituted with 1 $R^3$ substituent and with 0-3 substituents selected from cyano, halo, alkyl, haloalkyl, alkoxy, and haloalkoxy; and
$Ar^2$ is phenyl, pyridinyl, pyrazinyl, pyrimidinyl, pyridazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, tetrazolyl, or benzimidazolyl, and is substituted with 0-3 substituents selected from cyano, halo, alkyl, haloalkyl, hydroxy, alkoxy, haloalkoxy, and phenyl;
or a pharmaceutically acceptable salt thereof.

2. The compound of claim 1 where
$R^1$ is hydrogen;
$R^2$ is hydrogen;
$R^3$ is

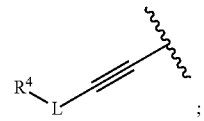

;

$R^4$ is cyano, alkyl, haloalkyl, cycloalkyl, hydroxy, alkoxy, haloalkoxy, or thioalkyl, where alkyl, haloalkyl, and cycloalkyl are substituted with 0-3 substituents selected from halo, alkyl, haloalkyl, hydroxy, and alkoxy;
or $R^4$ is a bridged [1-4.1-4.0-3]bicycloalkyl;
or $R^4$ is alkylcarbonylamino, haloalkylcarbonylamino, cycloalkanonyl, valerolactamyl, oxetanyl, tetrahydrofuranyl, tetrahydropyranyl, or tetrahydropyranyloxy;
or $R^4$ is amino, alkylamino, dialkylamino, azetidinyl, pyrrolidinyl, piperidinyl, piperazinyl, morpholinyl, homopiperidinyl, homopiperazinyl, or homomorpholinyl;
L is a bond, alkylene, or hydroxyalkylene;
$Ar^1$ is phenyl, pyridinyl, pyrazinyl, pyrimidinyl, or pyridazinyl, and is substituted with 1 $R^3$ substituent and with 0-3 substituents selected from cyano, halo, alkyl, haloalkyl, alkoxy, and haloalkoxy; and
$Ar^2$ is phenyl, pyridinyl, pyrazinyl, pyrimidinyl, pyridazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, tetrazolyl, or benzimidazolyl, and is substituted with 0-3 substituents selected from cyano, halo, alkyl, haloalkyl, hydroxy, alkoxy, haloalkoxy, and phenyl;
or a pharmaceutically acceptable salt thereof.

3. The compound of claim 2 where $R^1$ is hydrogen; $R^2$ is hydrogen; $R^3$ is

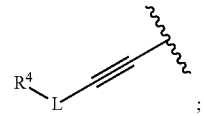

;

R⁴ is cyano, alkyl, haloalkyl, cycloalkyl, hydroxy, alkoxy, haloalkoxy, or thioalkyl, where alkyl, haloalkyl, and cycloalkyl are substituted with 0-3 substituents selected from halo, alkyl, haloalkyl, hydroxy, and alkoxy; or R⁴ is a bridged [1-4.1-4.0-3]bicycloalkyl; or R⁴ is alkylcarbonylamino, haloalkylcarbonylamino, cycloalkanonyl, valerolactamyl, oxetanyl, tetrahydrofuranyl, tetrahydropyranyl, or tetrahydropyranyloxyy; or R⁴ is amino, alkylamino, dialkylamino, azetidinyl, pyrrolidinyl, piperidinyl, piperazinyl, morpholinyl, homopiperidinyl, homopiperazinyl, or homomorpholinyl; L is a bond, alkylene, or hydroxyalkylene; Ar¹ is pyridinyl substituted with 1 R³ substituent and with 0-3 substituents selected from cyano, halo, alkyl, haloalkyl, alkoxy, and haloalkoxy; and Ar² is phenyl substituted with 0-3 substituents selected from cyano, halo, alkyl, haloalkyl, hydroxy, alkoxy, haloalkoxy, and phenyl; or a pharmaceutically acceptable salt thereof.

4. The compound of claim 1 where R¹ and R² are hydrogen.

5. The compound of claim 1 where R⁴ is cyano, alkyl, haloalkyl, cycloalkyl, hydroxy, alkoxy, haloalkoxy, or thioalkyl, where alkyl, haloalkyl, and cycloalkyl are substituted with 0-3 substituents selected from halo, alkyl, haloalkyl, hydroxy, and alkoxy.

6. The compound of claim 1 where R⁴ is amino, alkylamino, dialkylamino, azetidinyl, pyrrolidinyl, piperidinyl, piperazinyl, morpholinyl, homopiperidinyl, homopiperazinyl, or homomorpholinyl.

7. The compound of claim 1 where L is a bond, methylene, or hydroxymethylene.

8. The compound of claim 1 where Ar¹ is pyridinyl substituted with 1 R³ substituent and with 0-3 substituents selected from cyano, halo, alkyl, haloalkyl, alkoxy, and haloalkoxy.

9. The compound of claim 1 where Ar² is phenyl substituted with 0-3 substituents selected from cyano, halo, alkyl, haloalkyl, hydroxy, alkoxy, haloalkoxy, and phenyl.

10. The compound of claim 1 with the indicated stereochemistry

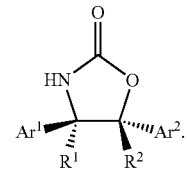

11. A pharmaceutical composition comprising a compound of claim 1, or a pharmaceutically acceptable salt thereof, and a pharmaceutically acceptable carrier.

12. A method for the treatment of schizophrenia which comprises administering to a patient a therapeutically affective amount of a compound of claim 1.

* * * * *

UNITED STATES PATENT AND TRADEMARK OFFICE
CERTIFICATE OF CORRECTION

PATENT NO. : 9,688,669 B2
APPLICATION NO. : 15/026759
DATED : June 27, 2017
INVENTOR(S) : Degnan et al.

It is certified that error appears in the above-identified patent and that said Letters Patent is hereby corrected as shown below:

In the Claims

Claim 3, Column 85, Line 8:
Delete "tetrahydropyranyloxyy;" and insert -- tetrahydropyranyloxy; --.

Signed and Sealed this
Eighteenth Day of September, 2018

Andrei Iancu
*Director of the United States Patent and Trademark Office*